United States Patent
Kessler et al.

(10) Patent No.: US 11,965,041 B2
(45) Date of Patent: Apr. 23, 2024

(54) N-METHYLATED CYCLIC PEPTIDES AND THEIR PRODRUGS

(71) Applicant: TECHNISCHE UNIVERSITAET MUENCHEN, Munich (DE)

(72) Inventors: Horst Otto Kessler, Schwalbach a. T. (DE); Chaim Gilon, Jerusalem (IL); Amnon Hoffman, Jerusalem (IL); Michael Weinmuller, Basel (CH); Florian Rechenmacher, Munich (DE); Joseph Fanous, Bat Yam (IL); Adi Klinger, Rishon Lezion (IL)

(73) Assignee: TECHNISCHE UNIVERSITAET MUENCHEN, Munich (DE)

( * ) Notice: Subject to any disclaimer, the term of this patent is extended or adjusted under 35 U.S.C. 154(b) by 545 days.

(21) Appl. No.: 16/648,272

(22) PCT Filed: Sep. 17, 2018

(86) PCT No.: PCT/IL2018/051050
§ 371 (c)(1),
(2) Date: Mar. 18, 2020

(87) PCT Pub. No.: WO2019/058374
PCT Pub. Date: Mar. 28, 2019

(65) Prior Publication Data
US 2020/0283483 A1    Sep. 10, 2020

Related U.S. Application Data

(60) Provisional application No. 62/560,217, filed on Sep. 19, 2017.

(51) Int. Cl.
C07K 7/64       (2006.01)
A61K 9/00       (2006.01)
A61K 38/00      (2006.01)

(52) U.S. Cl.
CPC .............. *C07K 7/64* (2013.01); *A61K 9/0053* (2013.01); *A61K 38/00* (2013.01)

(58) Field of Classification Search
CPC ......... C07K 7/64; A61K 9/0053; A61K 38/00
See application file for complete search history.

(56) References Cited

U.S. PATENT DOCUMENTS 5,866,540 A * 2/1999 Jonczyk ................. A61P 29/00
                                                                514/19.3
2003/0008814 A1   1/2003 Chen
2004/0152769 A1   8/2004 Ekwuribe

FOREIGN PATENT DOCUMENTS

| CN | 102264756 A | 11/2011 |
| CN | 102917589 A | 2/2013 |
| CN | 103025164 A | 4/2013 |
| WO | 9712904 A1 | 4/1997 |
| WO | 2010140886 A1 | 12/2010 |
| WO | 2011079015 A1 | 6/2011 |
| WO | 2014130949 A1 | 8/2014 |
| WO | 2015071841 A1 | 5/2015 |
| WO | 2019058367 A1 | 3/2019 |

OTHER PUBLICATIONS

Martin Pfaff, Selective recognition of cyclic RGD peptides of NMR defined conformation by alpha IIb beta 3, alpha V beta 3, and alpha 5 beta 1 integrins, vol. 269, Issue 32, Aug. 12, 1994, pp. 20233-20238.*
Yaniv Linde, Structure-Activity Relationship and Metabolic Stability Studies of Backbone Cyclization and N-Methylation of Melanocortin Peptides, Biopolymers. 2008 ; 90(5): 671-682. doi: 10.1002/bip.21057.*
Burger's Medicinal Chemistry and Drug Discovery. Volume 1, Principles and Practice, Fifth Edition, ManfredE. Wolff, Editor. Wiley: New York. NY, 1995.*
Naibo Yin, Enhancing the Oral Bioavailability of Peptide Drugs by using Chemical Modification and Other Approaches, Med chem 2014, 4:12.*
Jayanta Chatterjee, Synthesis of N-methylated cyclic peptides, 432-444, vol. 7 No. 3 | 2012 | nature protocols.*
Martin Pfaff, Selective Recognition of Cyclic RGD Peptides of NRIR Defined Conformation by allbp3, aVP3, and a5pl Integrins, JBC, vol. 269, No. 32, Issue of Aug. 12, pp. 20233-20238, 1994.*
Hans Maag, Prodrugs of Carboxylic Acids, Chapter 3.1, pp. 1-27, 2007.*
Gurrath et al., (1992) Conformation/activity studies of rationally designed potent anti-adhesive RGD peptides. Eur J Biochem 210(3): 911-921.
Afargan et al., (2001) Novel long-acting somatostatin analog with endocrine selectivity: potent suppression of growth hormone but not of insulin. Endocrinology 142(1): 477-486.
Artursson (1990) Epithelial transport of drugs in cell culture. I: A model for studying the passive diffusion of drugs over intestinal absorptive (Caco-2) cells. J Pharm Sci 79(6): 476-482.
Artursson and Karlsson (1991) Correlation between oral drug absorption in humans and apparent drug permeability coefficients in human intestinal epithelial (Caco-2) cells. Biochem Biophys Res Commun 175(3): 880-885.
Aumailley et al., (1991) Arg-Gly-Asp constrained within cyclic pentapeptides. Strong and selective inhibitors of cell adhesion to vitronectin and laminin fragment P1. FEBS Lett 291(1): 50-54.

(Continued)

Primary Examiner — Julie Ha
Assistant Examiner — Erinne R Dabkowski
(74) Attorney, Agent, or Firm — RAPHAEL BELLUM PLLC

(57) ABSTRACT

The present invention provides N-methylated cyclic hexapeptides comprising RGD and at least one alanine residue. The present invention further provides prodrugs comprising the cyclic hexapeptides. Pharmaceutical compositions comprising said cyclic hexapeptides are also disclosed as well as methods of their production and use in treating integrin related conditions and diseases.

12 Claims, 22 Drawing Sheets

Specification includes a Sequence Listing.

(56) References Cited

OTHER PUBLICATIONS

Bauer et al., (1982) SMS 201-995: a very potent and selective octapeptide analogue of somatostatin with prolonged action. Life Sci 31(11): 1133-1140.

Beck et al., (2012) Intestinal permeability of cyclic peptides: common key backbone motifs identified. J Am Chem Soc 134(29): 12125-12133 with Supporting Information.

Becker et al., (2015) Metabolism and disposition of the av-integrin β3/β5 receptor antagonist cilengitide, a cyclic polypeptide, in humans. J Clin Pharmacol 55(7): 815-824.

Bernkop-Schnürch and Schmitz (2007) Presystemic metabolism of orally administered peptide drugs and strategies to overcome it. Curr Drug Metab 8(5): 509-517.

Biron et al., (2008) Improving oral bioavailability of peptides by multiple N-methylation: somatostatin analogues. Angew Chem Int Ed Engl 47(14): 2595-2599 with Supporting Information.

Bochen et al., (2013) Biselectivity of isoDGR peptides for fibronectin binding integrin subtypes α5β1 and αvβ6: conformational control through flanking amino acids. J Med Chem 56(4): 1509-1519 with Supporting Information.

Bock et al., (2013) Getting in shape: controlling peptide bioactivity and bioavailability using conformational constraints. ACS Chem Biol 8(3): 488-499.

Bousquet et al., (2001) Antiproliferative Effect of Somatostatin and Analogs. Chemotherapy 47(suppl 2): 30-39.

Chatterjee et al., (2008) N-methylation of peptides: a new perspective in medicinal chemistry. Acc Chem Res 41(10): 1331-1342.

Cherniakov et al., (2015) Self-nano-emulsifying drug delivery systems: an update of the biopharmaceutical aspects. Expert Opin Drug Deliv 12(7): 1121-1133.

Cherniakov et al., (2017) The effect of Pro NanoLipospheres (PNL) formulation containing natural absorption enhancers on the oral bioavailability of delta-9-tetrahydrocannabinol (THC) and cannabidiol (CBD) in a rat model. Eur J Pharm Sci 109: 21-30.

Craik et al., (2013) The future of peptide-based drugs. Chem Biol Drug Des 81(1): 136-147.

Dechantsreiter et al., (1999) N-Methylated cyclic RGD peptides as highly active and selective alpha(V)beta(3) integrin antagonists. J Med Chem 42(16): 3033-3040 with Supporting Information.

Desgrosellier and Cheresh (2010) Integrins in cancer: biological implications and therapeutic opportunities. Nat Rev Cancer 10(1): 9-22.

Dong et al., (2017) Force interacts with macromolecular structure in activation of TGF-β. Nature 542(7639): 55-69.

Douillard et al., (2000) Irinotecan combined with fluorouracil compared with fluorouracil alone as first-line treatment for metastatic colorectal cancer: a multicentre randomised trial. Lancet 355(9209): 1041-1047.

Eisert et al., (2010) Dabigatran: an oral novel potent reversible nonpeptide inhibitor of thrombin. Arterioscler Thromb Vasc Biol 30(10): 1885-1889.

Falb et al., (2001) A bicyclic and hsst2 selective somatostatin analogue: design, synthesis, conformational analysis and binding. Bioorg Med Chem 9(12): 3255-3264.

Frank et al., (2010) Conformational control of integrin-subtype selectivity in isoDGR peptide motifs: a biological switch. Angew Chem Int Ed Engl 49(48): 9278-9281.

Friedler et al., (1998) Backbone cyclic peptide, which mimics the nuclear localization signal of human immunodeficiency virus type 1 matrix protein, inhibits nuclear import and virus production in nondividing cells. Biochemistry 37(16): 5616-5622.

Friesner et al., (2004) Glide: a new approach for rapid, accurate docking and scoring. 1. Method and assessment of docking accuracy. J Med Chem 47(7): 1739-1749.

Gilon et al., (1991) Backbone cyclization: A new method for conferring conformational constraint on peptides. Biopolymers 31(6): 745-750.

Gilon et al., (1998) A backbone-cyclic, receptor 5-selective somatostatin analogue: synthesis, bioactivity, and nuclear magnetic resonance conformational analysis. J Med Chem 41(6): 919-929.

Greenwood et al., (2010) Towards the comprehensive, rapid, and accurate prediction of the favorable tautomeric states of drug-like molecules in aqueous solution. J Comput Aided Mol Des 24(6-7): 591-604.

Grozinsky-Glasberg et al., (2008) Somatostatin analogues in the control of neuroendocrine tumours: efficacy and mechanisms. Endocr Relat Cancer 15(3): 701-720.

Halgren et al., (2004) Glide: a new approach for rapid, accurate docking and scoring. 2. Enrichment factors in database screening. J Med Chem 47(7): 1750-1759.

Hamman et al., (2005) Oral delivery of peptide drugs: barriers and developments. BioDrugs 19(3): 165-177.

Han and Amidon (2000) Targeted prodrug design to optimize drug delivery. AAPS PharmSci 2(1): E6; 11 pages.

Harder et al., (2016) OPLS3: A Force Field Providing Broad Coverage of Drug-like Small Molecules and Proteins. J Chem Theory Comput 12(1): 281-296.

Haubner et al., (1997) Stereoisomeric Peptide Libraries and Peptidomimetics for Designing Selective Inhibitors of the αvβ3 Integrin for a New Cancer Therapy. Angewandte Chemie International Edition in English 36(13-14): 1374-1389.

Hayashi et al., (1998) GPIIb/IIIa integrin antagonists with the new conformational restriction unit, trisubstituted beta-amino acid derivatives, and a substituted benzamidine structure. J Med Chem 41(13): 2345-2360 with Supporting Information.

Heron et al., (1993) Pharmacokinetics and efficacy of a long-acting formulation of the new somatostatin analog BIM 23014 in patients with acromegaly. J Clin Endocrinol Metab 76(3): 721-727.

Hoole and West (2016) Bivalirudin in the treatment of acute coronary syndrome. BMJ 352: 186; 2 pages.

Hruby and Balse (2000) Conformational and topographical considerations in designing agonist peptidomimetics from peptide leads. Curr Med Chem 7(9): 945-970.

Hubatsch et al., (2007) Determination of drug permeability and prediction of drug absorption in Caco-2 monolayers. Nat Protoc 2(9): 2111-2119.

Hunter et al., (1993) Drug absorption limited by P-glycoprotein-mediated secretory drug transport in human intestinal epithelial Caco-2 cell layers. Pharm Res 10(5): 743-749.

International Union of Pure and Applied Chemistry (IUPAC) and International Union of Biochemistry (IUB), Joint Commission on Biochemical Nomenclature (JCBN); (1984) Nomenclature and symbolism for amino acids and peptides (Recommendations 1983). Pure & Appl Chem 56(5): 595-624.

Jornada et al., (2015) The Prodrug Approach: A Successful Tool for Improving Drug Solubility. Molecules 21(1): 42; 31 pages.

Ju et al., (2008) Stereoretentive synthesis and chemoselective amide-forming ligations of C-terminal peptide alpha-ketoacids. J Am Chem Soc 130(13): 4253-4255.

Kansy et al., (1998) Physicochemical High Throughput Screening: Parallel Artificial Membrane Permeation Assay in the Description of Passive Absorption Processes. J Med Chem 41(7): 1007-1010 with Supporting Information.

Kansy et al., (2004) Advances in screening for membrane permeability: high-resolution PAMPA for medicinal chemists. Drug Discovery Today: Technologies 1(4): 349-355.

Kapp et al., (2013) Integrin modulators: a patent review. Expert Opin Ther Pat 23(10): 1273-1295.

Kapp et al., (2016) Small Cause, Great Impact: Modification of the Guanidine Group in the RGD Motif Controls Integrin Subtype Selectivity. Angew Chem Int Ed Engl 55(4): 1540-1543 with Supporting Information.

Kapp et al., (2017) A Comprehensive Evaluation of the Activity and Selectivity Profile of Ligands for RGD-binding Integrins. Sci Rep 7: 39805; 13 pages.

Kessler H (2017); Design of an orally available peptide with biological activity. Presented at 38th Max-Bergmann-Conferencem Achalm (Reutlingen), Germany; Sep. 24-27, 2017. 52 pages.

Kumar et al., (1999) Subtype-selective expression of the five somatostatin receptors (hSSTR1-5) in human pancreatic islet cells: a quantitative double-label immunohistochemical analysis. Diabetes 48(1): 77-85.

(56) References Cited

OTHER PUBLICATIONS

Kumar et al., (2010) Caco-2 cell lines in drug discovery—an updated perspective. J Basic Clin Pharm 1(2): 63-69.
Lahlou et al., (2004) Molecular Signaling of Somatostatin Receptors. Annals of the New York Academy of SciencesVolume 1014(1): 121-131.
Lamberts et al., (1996) Octreotide. N Engl J Med 334(4): 246-254.
Ley et al., (2016) Integrin-based therapeutics: biological basis, clinical use and new drugs. Nat Rev Drug Discov 15(3): 173-183.
Linde et al., (2008) Structure-activity relationship and metabolic stability studies of backbone cyclization and N-methylation of melanocortin peptides. Biopolymers 90(5): 671-682.
Lipinski et al., (2001) Experimental and computational approaches to estimate solubility and permeability in drug discovery and development settings. Adv Drug Deliv Rev 46(1-3): 3-26.
Luhn et al., (2012) Dissolution Profile of Novel Composite Pellet Cores Based on Different Ratios of Microcrystalline Cellulose and Isomalt. Journal of Pharmaceutical Sciences 101(8): 2675-2680.
Marelli et al., (2015) cis-Peptide Bonds: A Key for Intestinal Permeability of Peptides? Chemistry 21(43): 15148-15152 with Supporting Information.
Marelli et al., (2015) Enantiomeric cyclic peptides with different Caco-2 permeability suggest carrier-mediated transport. Chemistry 21(22): 8023-8027 with Supporting Information.
Mas-Moruno et al., (2010) Cilengitide: the first anti-angiogenic small molecule drug candidate design, synthesis and clinical evaluation. Anticancer Agents Med Chem 10(10): 753-768.
Mezey et al., (1998) Cell specific expression of the sst2A and sst5 somatostatin receptors in the rat anterior pituitary. Endocrinology 139(1): 414-419.
Mitra et al., (1999) Colocalization of somatostatin receptor sst5 and insulin in rat pancreatic beta-cells. Endocrinology 140(8): 3790-3796.
Muñoz-Félix et al., (2017); Low doses of a new orally administered cyclic RGD peptide prodrug 29P increases and angiogenesis and is a powerful tool for vascular promotion cancer therapy. Presented at the 1st Crick Meeting in London, Sep. 24-26, 2017. 1 page.
Nabors et al., (2015) Two cilengitide regimens in combination with standard treatment for patients with newly diagnosed glioblastoma and unmethylated MGMT gene promoter: results of the open-label, controlled, randomized phase II Core study. Neuro Oncol 17(5): 708-717.
Oberg (2004) Future aspects of somatostatin-receptor-mediated therapy. Neuroendocrinology 80 Suppl 1: 57-61.
Ovadia et al., (2010) Improvement of drug-like properties of peptides: the somatostatin paradigm. Expert Opin Drug Discov 5(7): 655-671.
Ovadia et al., (2010) The effect of backbone cyclization on PK/PD properties of bioactive peptide-peptoid hybrids: the melanocortin agonist paradigm. Bioorg Med Chem 18(2): 580-589.
Ovadia et al., (2011) The effect of multiple N-methylation on intestinal permeability of cyclic hexapeptides. Mol Pharm 8(2): 479-487.
Patel et al., (1990) Mechanism of action of somatostatin: An overview of receptor function and studies of the molecular characterization and purification of somatostatin receptor proteins. Metabolism 39(9, Suppl 2): 63-69.
Phillips and Arena (2003) MultiScreen® Caco-2 Assay System. Optimization of Caco-2 cell growth and differentiation for drug transport assay studies using a 96-well assay system. Lit. No. PC1060EN00; Rev.—Aug. 2003; 12 pages.
Picariello et al., (2016) Use of brush border membrane vesicles to simulate the human intestinal digestion. Food Research International 88(Part B): 327-335.
Pollak and Schally (1998) Mechanisms of antineoplastic action of somatostatin analogs. Proc Soc Exp Biol Med 217(2): 143-152.
Powell (1993) Chapter 30. Peptide Stability in Drug Development: in vitro Peptide Degradation in Plasma and Serum. Annual Reports in Medicinal Chemistry 28: 285-294.
Räder et al., (2018) Orally Active Peptides: Is There a Magic Bullet? Angew Chem Int Ed Engl 57(44): 14414-14438.
Reardon et al., (2011) Cilengitide: an RGD pentapeptide aαvβ3 and αvβ5 integrin inhibitor in development for glioblastoma and other malignancies. Future Oncol 7(3): 339-354.
Reichlin (1983) Somatostatin. N Engl J Med 309(24): 1495-501.
Renukuntla et al., (2013) Approaches for enhancing oral bioavailability of peptides and proteins. Int J Pharm 447(1-2): 75-93.
Reynolds et al., (2009) Stimulation of tumor growth and angiogenesis by low concentrations of RGD-mimetic integrin inhibitors. Nat Med 15(4): 392-400.
Saltz (1999) Weekly irinotecan, leucovorin, and fluorouracil is superior to daily X5 leucovorin/5-fluorouracil in patients with previously untreated metastatic colorectal cancer. Proc ASCO 18: 233a; abstract #898.
Sastry et al., (2013) Protein and ligand preparation: parameters, protocols, and influence on virtual screening enrichments. J Comput Aided Mol Des 27(3): 221-234.
Scarpignato and Pelosini (2001) Somatostatin Analogs for Cancer Treatment and Diagnosis: An Overview. Chemotherapy 47(suppl 2): 1-29.
Schally (1988) Oncological applications of somatostatin analogues. Cancer Res 48(24 Pt 1): 6977-6985.
Schumacher-Klinger et al., (2018) Enhancing Oral Bioavailability of Cyclic RGD Hexa-peptides by the Lipophilic Prodrug Charge Masking Approach: Redirection of Peptide Intestinal Permeability from a Paracellular to Transcellular Pathway. Mol Pharm 15(8): 3468-3477.
Shan et al., (1997) Prodrug strategies based on intramolecular cyclization reactions. J Pharm Sci 86(7): 765-767.
Shelley et al., (2007) Epik: a software program for pK(a) prediction and protonation state generation for drug-like molecules. J Comput Aided Mol Des 21(12): 681-691.
Simplício et al., (2008) Prodrugs for amines. Molecules 13(3): 519-547.
Springer et al., (2008) Structural basis for distinctive recognition of fibrinogen γC peptide by the platelet integrin αIIbβ3. J Cell Biol 182(4): 791-800.
Srinivasan et al., (2015) TEER Measurement Techniques for In Vitro Barrier Model Systems. J Lab Autom 20(2): 107-126.
Takagi et al., (2003) Structure of integrin alpha5beta1 in complex with fibronectin. The EMBO Journal 22(18): 4607-4615.
Tsomaia (2015) Peptide therapeutics: targeting the undruggable space. Eur J Med Chem 94: 459-470.
Van Ryn et al., (2013) The discovery of dabigatran etexilate. Front Pharmacol 4: 12; 8 pages.
Veber et al., (1981) A potent cyclic hexapeptide analogue of somatostatin. Nature 292(5818): 55-58.
Vilaça et al., (2014) New cyclic RGD peptides: synthesis, characterization, and theoretical activity towards αvβ3 integrin. Tetrahedron 70(35): 5420-5427.
Wang and Craik (2016) Cyclic peptide oral bioavailability: Lessons from the past. Biopolymers 106(6): 901-909.
Weide T., Modlinger A., Kessler H. (2006) Spatial Screening for the Identification of the Bioactive Conformation of Integrin Ligands. In: Peters T. (eds) Bioactive Conformation I. Topics in Current Chemistry, vol. 272. Springer, Berlin, Heidelberg; pp. 1-50.
Weinmüller et al., (2017) Overcoming the Lack of Oral Availability of Cyclic Hexapeptides: Design of a Selective and Orally Available Ligand for the Integrin αvβ3. Angew Chem Int Ed Engl 56(51): 16405-16409 with Supporting Information.
Wong et al., (2015) Dual-action combination therapy enhances angiogenesis while reducing tumor growth and spread. Cancer Cell 27(1): 123-137 with Supporting Information.
Wong et al., (2016) Exploring Novel Methods for Modulating Tumor Blood Vessels in Cancer Treatment. Curr Biol 26(21): R1161-R1166.
Xiong et al., (2002) Crystal structure of the extracellular segment of integrin alpha Vbeta3 in complex with an Arg-Gly-Asp ligand. Science 296(5565): 151-155.
Xiong et al., (2009) Crystal structure of the complete integrin alphaVbeta3 ectodomain plus an alpha/beta transmembrane fragment. J Cell Biol 186(4): 589-600.

(56) References Cited

OTHER PUBLICATIONS

Zablocki et al., (1995) Potent in vitro and in vivo inhibitors of platelet aggregation based upon the Arg-Gly-Asp sequence of fibrinogen. (Aminobenzamidino)succinyl (ABAS) series of orally active fibrinogen receptor antagonists. J Med Chem 38(13): 2378-2394 with Supporting Information.

Zimmer et al., (1993) "Head-to-Tail" Cyclization of Hexapeptides Using Different Coupling Reagents. Liebigs Annalen der Chemie 1993(5): 497-501.

Chen Xiaoping (1994) Peptide and protein drugs [oral administration]. International Journal of Pharmaceutical Research 2(2): 108-114. Machine translated abstract.

Jiang Bo et al., (2011) Progress in Chemical Modification of Peptide. Chemistry World 52(4): 251-255. Abstract.

Kahns and Bundgaard (1991) N-Acyl derivatives as prodrug forms for amides: Chemical stability and enzymatic hydrolysis of various N-acyl and N-alkoxycarbonyl amide derivatives. International Journal of Pharmaceutics 71(1-2): 31-43. Abstract.

Li Anliang et al., (2000) Medicinal chemistry and bioavailability manipulations. West China Journal of Pharmaceutical Sciences 15(2): 364-366. Abstract.

Luo Zhigang et al., (2005) Research on synthesis of RGD sequences mimetics. Pharmaceutical Journal of Chinese People's Liberation Army 21(2): 129-132. Machine translated abstract.

Ma Jianbiao editor-in-chief (2000) Functional Polymer Materials. Jul. 31, 2000. Chemical Industry Press, Beijing China. p. 161. Machine translation.

Nofsinger and Borchardt (2012) Factors that Restrict the Cell Permeation of Cyclic Prodrugs of an Opioid Peptide, Part 4: Characterization of the Biopharmaceutical and Physicochemical Properties of Two New Cyclic Prodrugs Designed to be Stable to Oxidative Metabolism by Cytochrome P-450 Enzymes in the Intestinal Mucosa. Journal of Pharmaceutical Sciences 101(9): 3500-3510.

Wang Shilong et al., (2012) Protein Chemistry. Aug. 31, 2012. Tongji University Press pp. 123, 126-127. Machine translation.

Yin Yongjia editor-in-chief (1985) University Chemistry Handbook. Feb. 28, 1985. Shandong Science and Technology Press. p. 567. Machine translation.

\* cited by examiner

SEQUENCE LISTING

```
<160> NUMBER OF SEQ ID NOS: 24

<210> SEQ ID NO 1
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N-methylated
<220> FEATURE:
<221> NAME/KEY: MISC_FEATURE
<222> LOCATION: (5)..(5)
<223> OTHER INFORMATION: N-methylated

<400> SEQUENCE: 1

Arg Gly Asp Ala Ala Ala
1               5

<210> SEQ ID NO 2
<211> LENGTH: 6
<212> TYPE: PRT
<213> ORGANISM: Artificial Sequence
<220> FEATURE:
<223> OTHER INFORMATION: cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (6)..(6)
<223> OTHER INFORMATION: N methylated

<400> SEQUENCE: 2

Ala Arg Gly Asp Ala Ala
```

```
1               5

<210> SEQ ID NO 3
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (3)..(3)
<223> OTHER INFORMATION: N methylated
<220> FEATURE:
<221> NAME/KEY: MISC_FEATURE
<222> LOCATION: (5)..(5)
<223> OTHER INFORMATION: N methylated

<400> SEQUENCE: 3

Arg Gly Asp Ala Ala Ala
1               5

<210> SEQ ID NO 4
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (5)..(5)
<223> OTHER INFORMATION: N methylated
<220> FEATURE:
<221> NAME/KEY: MISC_FEATURE
<222> LOCATION: (6)..(6)
<223> OTHER INFORMATION: N methylated

<400> SEQUENCE: 4

Arg Gly Asp Ala Ala Ala
1               5

<210> SEQ ID NO 5
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (6)..(6)
<223> OTHER INFORMATION: N methylated

<400> SEQUENCE: 5

Val Arg Gly Asp Ala Ala
1               5

<210> SEQ ID NO 6
```

```
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (6)..(6)
<223> OTHER INFORMATION: N methylated

<400> SEQUENCE: 6

Phe Arg Gly Asp Ala Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (5)..(5)
<223> OTHER INFORMATION: N methylated

<400> SEQUENCE: 7

Arg Gly Asp Ala Ala Val
1               5

<210> SEQ ID NO 8
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (5)..(5)
<223> OTHER INFORMATION: N methylated

<400> SEQUENCE: 8

Arg Gly Asp Ala Ala Phe
1               5

<210> SEQ ID NO 9
<211> LENGTH: 6
<212> TYPE: PRT
<213> ORGANISM: Artificial Sequence
<220> FEATURE:
```

<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (2)..(2)
<223> OTHER INFORMATION: Two hexyloxycarbonyl (Hoc) moieties
<220> FEATURE:
<221> NAME/KEY: MISC_FEATURE
<222> LOCATION: (4)..(4)
<223> OTHER INFORMATION: Methyl ester (OMe) moiety
<220> FEATURE:
<221> NAME/KEY: MISC_FEATURE
<222> LOCATION: (6)..(6)
<223> OTHER INFORMATION: N methylated

<400> SEQUENCE: 9

Val Arg Gly Asp Ala Ala
1               5

<210> SEQ ID NO 10
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (2)..(2)
<223> OTHER INFORMATION: Two hexyloxycarbonyl (Hoc) moieties
<220> FEATURE:
<221> NAME/KEY: MISC_FEATURE
<222> LOCATION: (4)..(4)
<223> OTHER INFORMATION: Methyl ester (OMe) moiety
<220> FEATURE:
<221> NAME/KEY: MISC_FEATURE
<222> LOCATION: (6)..(6)
<223> OTHER INFORMATION: N methylated

<400> SEQUENCE: 10

Ala Arg Gly Asp Ala Ala
1               5

<210> SEQ ID NO 11
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (1)..(1)
<223> OTHER INFORMATION: Two hexyloxycarbonyl (Hoc) moieties

```
<220> FEATURE:
<221> NAME/KEY: MISC_FEATURE
<222> LOCATION: (3)..(3)
<223> OTHER INFORMATION: Methyl ester (OMe) moiety
<220> FEATURE:
<221> NAME/KEY: MISC_FEATURE
<222> LOCATION: (5)..(5)
<223> OTHER INFORMATION: N methylated

<400> SEQUENCE: 11

Arg Gly Asp Ala Ala Ala
1               5

<210> SEQ ID NO 12
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Two hexyloxycarbonyl (Hoc) moieties
<220> FEATURE:
<221> NAME/KEY: MISC_FEATURE
<222> LOCATION: (3)..(3)
<223> OTHER INFORMATION: Methyl ester (OMe) moiety
<220> FEATURE:
<221> NAME/KEY: MISC_FEATURE
<222> LOCATION: (5)..(5)
<223> OTHER INFORMATION: N methylated
<220> FEATURE:
<221> NAME/KEY: MISC_FEATURE
<222> LOCATION: (6)..(6)
<223> OTHER INFORMATION: N methylated

<400> SEQUENCE: 12

Arg Gly Asp Ala Ala Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: Two hexyloxycarbonyl (Hoc) moieties
<220> FEATURE:
<221> NAME/KEY: MISC_FEATURE
<222> LOCATION: (3)..(3)
<223> OTHER INFORMATION: N methylated
<220> FEATURE:
<221> NAME/KEY: MISC_FEATURE
<222> LOCATION: (3)..(3)
<223> OTHER INFORMATION: Methyl ester (OMe) moiety
<220> FEATURE:
<221> NAME/KEY: MISC_FEATURE
<222> LOCATION: (5)..(5)
<223> OTHER INFORMATION: N metylated

<400> SEQUENCE: 13

Arg Gly Asp Ala Ala Ala
1               5
```

```
<210> SEQ ID NO 14
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (2)..(2)
<223> OTHER INFORMATION: Two hexyloxycarbonyl (Hoc) moieties
<220> FEATURE:
<221> NAME/KEY: MISC_FEATURE
<222> LOCATION: (4)..(4)
<223> OTHER INFORMATION: Methyl ester (OMe) moiety
<220> FEATURE:
<221> NAME/KEY: MISC_FEATURE
<222> LOCATION: (6)..(6)
<223> OTHER INFORMATION: N methylated

<400> SEQUENCE: 14

Phe Arg Gly Asp Ala Ala
1               5

<210> SEQ ID NO 15
<211> LENGTH: 9
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (5)..(5)
<223> OTHER INFORMATION: Two hexyloxycarbonyl (Hoc) moieties

<400> SEQUENCE: 15

Leu Pro Pro Phe Arg Gly Asp Leu Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (6)..(6)
<223> OTHER INFORMATION: Two hexyloxycarbonyl (Hoc) moieties

<400> SEQUENCE: 16

Leu Pro Pro Gly Leu Arg Gly Asp
1               5

<210> SEQ ID NO 17
<211> LENGTH: 9
<212> TYPE: PRT
<213> ORGANISM: Artificial Sequence
<220> FEATURE:
<223> OTHER INFORMATION: Cyclic peptide

<400> SEQUENCE: 17

Leu Pro Pro Phe Arg Gly Asp Leu Ala
```

```
1               5

<210> SEQ ID NO 18
<211> LENGTH: 8
<212> TYPE: PRT
<213> ORGANISM: Artificial Sequence
<220> FEATURE:
<223> OTHER INFORMATION: Cyclic peptide

<400> SEQUENCE: 18

Leu Pro Pro Gly Leu Arg Gly Asp
1               5

<210> SEQ ID NO 19
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid

<400> SEQUENCE: 19

Ala Ala Ala Ala Ala Ala
1               5

<210> SEQ ID NO 20
<211> LENGTH: 5
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: N methylated

<400> SEQUENCE: 20

Phe Val Arg Gly Asp
1               5

<210> SEQ ID NO 21
<211> LENGTH: 6
<212> TYPE: PRT
<213> ORGANISM: Artificial Sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (1)..(1)
<223> OTHER INFORMATION: N methylated
<220> FEATURE:
<221> NAME/KEY: MISC_FEATURE
<222> LOCATION: (2)..(2)
<223> OTHER INFORMATION: Hexyloxycarbonyl (Hoc) moiety
<220> FEATURE:
<221> NAME/KEY: MISC_FEATURE
<222> LOCATION: (4)..(4)
<223> OTHER INFORMATION: Methyl ester (OMe) moiety
<220> FEATURE:
<221> NAME/KEY: MISC_FEATURE
<222> LOCATION: (6)..(6)
```

```
<223> OTHER INFORMATION: N methylated

<400> SEQUENCE: 21

Val Arg Gly Asp Ala Ala
1               5

<210> SEQ ID NO 22
<211> LENGTH: 6
<212> TYPE: PRT
<213> ORGANISM: Artificial sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: N methylayed
<220> FEATURE:
<221> NAME/KEY: MISC_FEATURE
<222> LOCATION: (3)..(3)
<223> OTHER INFORMATION: Two hexyloxycarbonyl (Hoc) moieties

<400> SEQUENCE: 22

Ala Ala Ala Ala Ala Ala
1               5

<210> SEQ ID NO 23
<211> LENGTH: 5
<212> TYPE: PRT
<213> ORGANISM: Artificial sequence
<220> FEATURE:
<223> OTHER INFORMATION: Cyclic peptide
<220> FEATURE:
<221> NAME/KEY: MISC_FEATURE
<222> LOCATION: (1)..(1)
<223> OTHER INFORMATION: D-amino acid
<220> FEATURE:
<221> NAME/KEY: MISC_FEATURE
<222> LOCATION: (2)..(2)
<223> OTHER INFORMATION: N methylated
<220> FEATURE:
<221> NAME/KEY: MISC_FEATURE
<222> LOCATION: (3)..(3)
<223> OTHER INFORMATION: Two hexyloxycarbonyl (Hoc) moieties

<400> SEQUENCE: 23

Phe Val Arg Gly Asp
1               5

<210> SEQ ID NO 24
<211> LENGTH: 9
<212> TYPE: PRT
<213> ORGANISM: Artificial sequence
<220> FEATURE:
<223> OTHER INFORMATION: Peptide

<400> SEQUENCE: 24

Arg Thr Asp Leu Asp Ser Leu Arg Thr
1               5
```

N-METHYLATED CYCLIC PEPTIDES AND THEIR PRODRUGS

FIELD OF THE INVENTION

The present invention relates to N-methylated cyclic hexapeptides having high metabolic stability and high affinity to integrin αvβ3. In particular, the present invention relates to cyclic N-methylated hexapeptides comprising the amino acids Arg, Gly, Asp, and Ala. The peptides are selective ligands to the integrin αvβ3 and suitable for oral administration when formulated as a prodrug.

BACKGROUND OF THE INVENTION

The integrin family of cell adhesion receptors regulates a diverse array of cellular functions crucial to the initiation, progression and metastasis of solid tumors. The importance of integrins in several cell types that affect tumor progression has made them an appealing target for cancer therapy. Integrin antagonists, including the αvβ3 and αvβ5 inhibitor cilengitide, have shown encouraging activity in clinical trials [1].

The tripeptide sequence Arg-Gly-Asp is a binding epitope on extracellular matrix proteins for integrins [2]. It was shown that peptide cyclization to rigidify the RGD sequence and the introduction of one D-amino acid in a distinct position for conformational control result in peptides with high affinity and high receptor selectivity among the members of the RGD recognizing subfamily of integrins. Later, an approach of a "spatial screening" allowed for the identification of a highly active ligand for integrin αvβ3 with strong reduction in the binding to the platelet integrin αIIbβ3 [3]. The original parent peptide, a cyclic pentapeptide, cyclo(RGDfV) was later optimized via mono N-methyl scan resulting in the drug cilengitide (cyclo(RGDf-(NMe)V)) [4,5]. This peptide has subnanomolar affinity to αvβ3 (IC$_{50}$ 0.6 nM), some affinity to αvβ5 [5], and in addition also to α5β1 [6]. Cilengitide was tested in clinical phase III for treatment of glioblastoma by parenteral administration. It is not metabolized and totally stable in vivo with a half live of 4 h in man [7]. However, it is orally not available like most polar biologically active peptides [8, 9].

Development of orally available peptides, either by improving their intestinal transport and/or by enhancing their stability to enzymatic degradation, has become a primary challenge for research groups in the past decade. One of the strategies suggested to improve intestinal permeability is N-methylation. Ovadia et al. describe N-methylated cyclic hexapeptides consisting of alanine residues that have a high permeability rate similar to the permeability of testosterone, a passive transcellular permeability marker [10].

In light of recent discoveries that implicate integrins in various new indications, and to overcome the inherent lack of bioavailability of charged peptides (especially Arg containing peptides) it is essential to develop new highly potent RGD containing peptide(s) with drug like properties (DLP).

SUMMARY OF THE INVENTION

The present invention provides N-methylated cyclic peptides having high metabolic stability and high affinity to integrin αvβ3. The cyclic peptides according to the invention comprising at least one N-methylated residue and the amino acids Arg, Gly, Asp, and Ala. The peptides are selective ligands for the integrin αvβ3 and highly suitable for oral administration when formulated as a prodrug. The peptides, pharmaceutical compositions comprising them, methods of their production and uses are provided. The present invention further provides in some embodiments cyclic hexapeptides comprising the amino acids Arg, Gly, Asp, and at least one Ala, said hexapeptides comprising a plurality of N-methylations. The present invention further provides in some embodiments peptides for use in treating integrin-related conditions and diseases.

The present invention is based in part on the unexpected discovery that N-methylated cyclic hexapeptides comprising Arg, Gly, Asp, and at least one Ala residue exhibit improved specific properties such as high affinity, high selectivity and metabolic stability. Pharmacokinetic studies showed that the peptides are highly stable and suitable for oral administration when formulated as a prodrug.

The teachings of the present invention are advantageous over previously known methods for using N-methylated cyclic hexapeptides having high stability and affinity to integrin for treating integrin-related conditions and diseases such as cancer.

According to a first aspect, the present invention provides an N-methylated cyclic hexapeptide or an analog thereof, comprising the sequence RGD and at least one alanine residue, wherein R is arginine residue (Arg) or a modified arginine residue, G is glycine residue (Gly) or a modified glycine residue, and D is aspartic acid (Asp) or a modified aspartic acid residue.

According to some embodiments, the N-methylated cyclic hexapeptide comprising the sequence RGD, wherein R is arginine residue (Arg), G is glycine residue (Gly), and D is aspartic acid (Asp).

According to some embodiments, the N-methylated cyclic hexapeptide comprises a plurality of N-methylations. According to certain embodiments, the N-methylated cyclic hexapeptide has two N-methylations. According to other embodiments, the N-methylated cyclic hexapeptide comprises 3, 4, or 5 N-methylations.

According to some embodiments, the N-methylations are in a position selected from the group consisting of (1,5), (1,6), (3,5), and (5,6), wherein the peptide comprises an amino acid in D configuration at position number 1.

According to some embodiments, the N-methylated cyclic hexapeptide comprises at least two alanine residues. According to certain embodiments, the N-methylated cyclic hexapeptide comprises two alanine residues. According to additional embodiments, the N-methylated cyclic hexapeptide comprises three alanine residues. According to other embodiments, the N-methylated cyclic hexapeptide comprises one alanine residue.

According to some embodiments, the N-methylated cyclic hexapeptide comprises an amino acid in the D configuration. According to certain embodiments, the N-methylated cyclic hexapeptide comprises an alanine residue in the D configuration. According to additional embodiments, the N-methylated cyclic hexapeptide comprises a glycine residue in the D configuration. According to additional embodiments, the N-methylated cyclic hexapeptide comprises a valine residue in the D configuration. According to additional embodiments, the N-methylated cyclic hexapeptide comprises a phenylalanine residue in the D configuration.

According to some embodiments, the N-methylated cyclic hexapeptide comprises a hydrophobic amino acid. According to certain embodiments, the hydrophobic amino acids is selected from the group consisting of valine and phenylalanine.

According to some embodiments, the N-methylated cyclic hexapeptide sequence is selected from the group consisting of:
(i) *rGDA*AA (peptide #5; SEQ ID NO: 1);
(ii) *aRGDA*A (peptide #12; SEQ ID NO: 2);
(iii) rG*DA*AA (peptide #17; SEQ ID NO: 3);
(iv) rGDA*A*A (peptide #23; SEQ ID NO: 4);
(v) *vRGDA*A (peptide #29; SEQ ID NO: 5);
(vi) *fRGDA*A (peptide #30; SEQ ID NO: 6);
(vii) *rGDA*AV (peptide #32; SEQ ID NO: 7); and
(viii) *rGDA*AF (peptide #33; SEQ ID NO: 8);
wherein * is N-methylation of the followed amino acid, R is arginine, G is glycine, D is aspartic acid, r is arginine in the D configuration, A is alanine, a is alanine in the D configuration, V is valine, v is valine in the D configuration, F is phenylalanine, and f is phenylalanine in the D configuration. Each possibility represents a separate embodiment of the invention.

According to some embodiments, the peptide comprises a head-to-tail cyclization.

Also included in the scope of the present invention are conjugates and fusion proteins comprising at least one N-methylated cyclic hexapeptide according to the invention.

According to some embodiments, the N-methylated cyclic hexapeptide is linked to at least one molecule that masks the charge of the amino acids. According to additional embodiments, the N-methylated cyclic hexapeptide is linked to at least one molecule that reduces the net charge of the hexapeptide.

According to some embodiments, the analog comprises modification selected from the group consisting of: 1-2 deletions of amino acids, 1-3 substitutions of amino acids, 1-2 additions of amino acids, addition of a linker, and combinations thereof. Each possibility represents a separate embodiment of the present invention.

According to an aspect, the present invention provides a prodrug comprising the N-methylated cyclic hexapeptide described herein and a permeability enhancing moiety.

The permeability-enhancing moiety according to the present invention is coupled to the peptide's sequence directly or through a spacer or linker. The spacer or linker may comprise a protease-specific cleavage site.

According to some embodiments, the prodrug comprises the N-methylated cyclic hexapeptide covalently linked to at least one —CO$_2$R moiety, wherein R is alkyl.

According to some embodiments, the permeability-enhancing moiety is an oxycarbonyl moiety.

According to some embodiments, the permeability-enhancing moiety is a hexyloxycarbonyl (Hoc) moiety.

Hoc in all structures designates hexyloxycarbonyl residue having the structure:

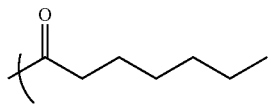

According to some embodiments, the cyclic peptide comprises two hexyloxycarbonyl (Hoc) moieties.

According to some embodiments, the guanidine group of Arg is masked with a hexyloxycarbonyl (Hoc) moiety. According to specific embodiments, the guanidine group of Arg is masked with two hexyloxycarbonyl (Hoc) moieties.

According to some embodiments, the cyclic peptide comprises a methyl ester (COOMe) residue.

According to some embodiments, the cyclic peptide comprises at least one side chain having the formula CH$_2$COOMe.

According to some embodiments the prodrug is having a net neutral charge. According to some embodiments the prodrug is devoid of positively charged atoms. According to certain embodiments, the prodrug is devoid of charged atoms. According to certain embodiments, the prodrug is devoid of charged atoms at physiological pH.

According to some embodiments, the prodrug has a formula selected from the group consisting of peptide 29P (c(*vR(Hoc)$_2$GD(OMe)A*A), SEQ ID NO: 9), peptide 12P (c(*aR(Hoc)$_2$GD(OMe)A*A), SEQ ID NO: 10), peptide 5P (c(*r(Hoc)$_2$GD(OMe)A*AA), SEQ ID NO: 11) and peptide 23P (c(r(Hoc)$_2$GD(OMe)A*A*A), SEQ ID NO: 12). Each possibility represents a separate embodiment of the invention.

According to some embodiments, the N-methylated cyclic hexapeptide binds to integrins. According to certain embodiments, the N-methylated cyclic hexapeptide binds with high affinity to the integrin αvβ3.

In another aspect, the present invention provides a pharmaceutical composition comprising as an active ingredient the N-methylated cyclic hexapeptide or the prodrug according to the invention. According to some embodiments, the pharmaceutical composition further comprises a pharmaceutically acceptable carrier, excipient or diluent.

According to some embodiments, the composition is formulated for an oral administration.

According to some embodiments, the pharmaceutical composition comprises absorption enhancers. According to some embodiments, the pharmaceutical composition further comprises lipids. According to some embodiments, the pharmaceutical composition further comprises self nano-emulsifying drug delivery systems (SNEDDS). According to certain embodiments, the pharmaceutical composition comprises Pro-NanoLiposphere (PNL).

According to some embodiments, the pharmaceutical composition comprises curcumin, resveratrol and/or piperine. According to some embodiments, the pharmaceutical composition comprises Resveratrol-PNL and/or Piperine-PNL.

According to some embodiments, the pharmaceutical composition comprises elements that reduce intra-enterocyte metabolism by CYP3A4 enzymes and/or reduce P-gp efflux activity.

According to some embodiments, the pharmaceutical composition comprises verapamil.

In another aspect, the present invention provides a pharmaceutical composition for use in treating cancer, the pharmaceutical composition comprises as an active ingredient the N-methylated cyclic hexapeptide or prodrug according to the invention.

In another aspect, the present invention provides a method of treating integrin-related condition or disease, the method comprising administering to a subject in need thereof, a therapeutically effective amount of the pharmaceutical composition described hereinabove.

In another aspect, the present invention provides a method of treating cancer, the method comprising administering to a subject in need thereof, a therapeutically effective amount of the pharmaceutical composition described hereinabove, thereby treating cancer in the subject.

According to some embodiments, the cancer is glioblastoma.

According to some embodiments, the route of administration of the composition is orally.

According to some embodiments, the N-methylated cyclic hexapeptide reduces integrin activity.

According to some embodiments, the N-methylated cyclic hexapeptide is capable of recognizing integrins.

The pharmaceutical composition according to the present invention may be administered as a standalone treatment or in addition to a treatment with any other known treatments for cancer. According to some embodiments, the other treatment is chemotherapy.

In some embodiments there is provided a process for preparing the prodrug, the process comprising:
(a) providing a peptide precursor;
(b) coupling said peptide precursor with a modified amino acid having the formula:

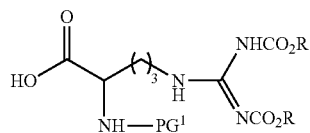

wherein
R is as defined herein;
PG' is a base-labile protecting group;
wherein the peptide precursor is selected from the group consisting of: an amino acid, a peptide and a solid phase resin;
(c) removing said base-labile protecting group PG' from the product of step (b) under basic conditions; and
(d) optionally coupling at least one additional amino acid; thereby forming the prodrug.

Other objects, features and advantages of the present invention will become clear from the following description and drawings.

BRIEF DESCRIPTION OF THE FIGURES

FIG. 21A is a stereo view of the solution state NMR conformation of 29 superimposed with the conformation of its orally available parent compound 2. For the sake of clarity, non-polar hydrogens are not shown. FIG. 21B shows binding mode of 29 to the αvβ3 integrin. Receptor amino acid side chains important for the ligand binding are represented as sticks.

DETAILED DESCRIPTION OF THE INVENTION

Figure 1:
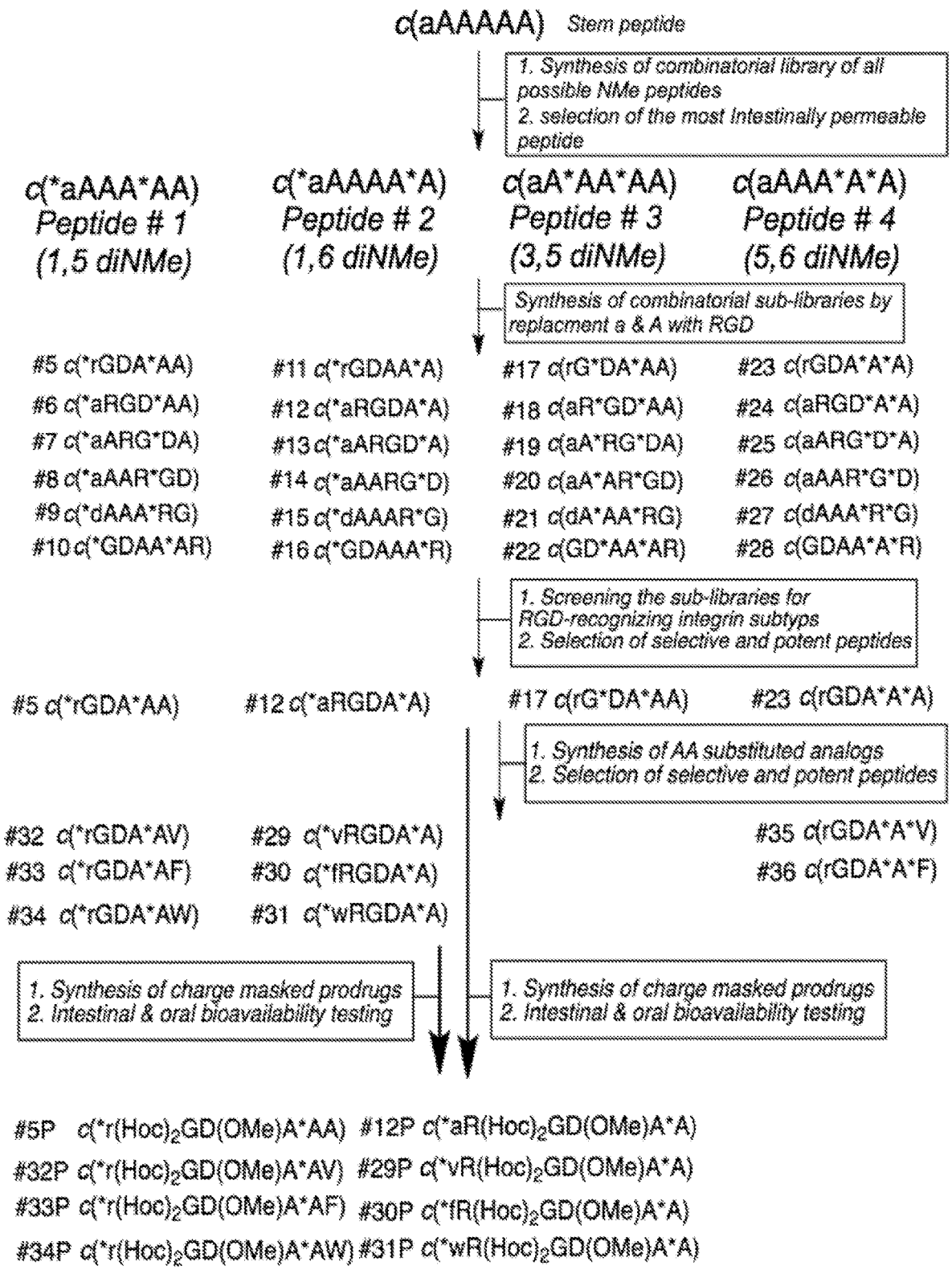
FIG. 1 is a flowchart depicting the development of orally available RGD containing N-methylated (NMe) cyclic hexapeptides. Abbreviations of amino acids are according to [9]. D-amino acids are represented as the one letter abbreviation but in small letter format. "a" is D-Ala; "r" is D-Arg; "d" is D-Asp. N-methylated amino acids are represented by a superscripted star on the left side of the one letter abbreviation. Thus, NMe Ala is *A, NMe D-Ala is *a, NMe Arg is *R, NMe D-Arg is *r, NMe Asp is *D and NMe D-Asp is *d. Hoc is hexyloxycarbonyl. OMe is O-methylated.

As a result of major advances in organic chemistry and in molecular biology, many bioactive peptides can now be prepared in quantities sufficient for pharmacological and clinical use. Thus, new methods have been established for the treatment of illnesses in which peptides have been implicated. However, the use of peptides as therapeutic and diagnostic agents is limited by the following factors: a)

tissue penetration; b) low metabolic stability towards proteolysis in the gastrointestinal tract and in serum; c) poor absorption after oral ingestion, in particular due to their relatively high molecular mass or the lack of specific transport systems or both; d) rapid excretion through the liver and kidneys; and e) undesired side effects in non-target organ systems, since peptide receptors can be widely distributed in an organism. The present invention provides bioactive peptides that: a) have improved tissue penetration when formulated as a prodrug due to their small size and optimal moieties; b) have improved metabolic stability; c) have improved absorption; and d) are selective to the specific integrins and therefore are expected to have less side effects.

The present invention provides cyclic N-methylated hexapeptides having high stability and affinity to integrin αvβ3. The present invention further provides cyclic N-methylated hexapeptides comprising the amino acids Arg, Gly, Asp, and Ala, which are selective and orally available when linked to masking moieties. The peptides are suitable for oral administration and affect integrin-related conditions and diseases.

According to an aspect, the present invention provides an N-methylated cyclic peptide comprising the sequence RGD and at least one alanine residue, wherein R is arginine residue (Arg) or a modified arginine residue, G is glycine residue (Gly) or a modified glycine residue, and D is aspartic acid (Asp) or a modified aspartic acid residue.

According to some embodiment, the peptide consists of 5 to 8 amino acids. According to specific embodiments, the peptide is a hexapeptide.

Definitions

For convenience, certain terms employed in the specification, examples and claims are described herein.

The term "peptide" as used herein is meant to encompass natural (genetically encoded), non-natural and/or chemically modified amino acid residues, each residue being characterized by having an amino and a carboxy terminus, connected one to the other by peptide or non-peptide bonds. The amino acid residues are represented throughout the specification and claims by either one or three-letter codes, as is commonly known in the art. The peptides of this invention are cyclized.

The term "hexapeptide" as used herein means a peptide with six amino acid residues.

The terms "N-methylation" or "NMe" are used herein interchangeably and refer to a form of alkylation wherein a methyl group, CH3, replaces the hydrogen atom of the NH moiety in the backbone amide NHs of residues within the peptides. The terms refer to a peptide having at least one N-methylated amino acid.

The amino acids in a sequence of peptides along the description are represented by a single letter as known in the art, wherein small letter represents the corresponding amino acid in the D configuration. An asterisk symbol followed by a letter means that the corresponding amino acid is N-methylated.

The terms "cyclo" or "cyclic" are used herein interchangeably and intend to indicate that the peptide is cyclized. Any type of cyclization may be applied, including but not limited to: end-to-tail cyclization, side chain to side chain, sidechain to terminal, disulfide bridge, or backbone cyclization. In some embodiments, the peptides comprise head-to-tail cyclization, namely having a covalent bond between the atoms of the amino terminal amino group and the carboxyl terminus of the peptide. A "c" letter followed by brackets delineating a peptide sequence means that said peptide is cyclic.

According to some embodiments, the N-methylated cyclic peptide comprising the sequence RGD, wherein R is arginine residue (Arg), G is glycine residue (Gly) or a modified glycine residue, and D is aspartic acid (Asp) residue or a modified aspartic acid residue. According to other embodiments, the N-methylated cyclic peptide comprising the sequence RGD, wherein R is arginine residue (Arg) or a modified arginine residue, G is glycine residue (Gly), and D is aspartic acid (Asp) residue or a modified aspartic acid residue. According to additional embodiments, the N-methylated cyclic peptide comprising the sequence RGD, wherein R is arginine residue (Arg) or a modified arginine residue, G is glycine residue (Gly) or a modified glycine residue, and D is aspartic acid (Asp) residue.

According to some embodiments, the N-methylated cyclic peptide comprises a plurality of N-methylations. According to certain embodiments, the N-methylated cyclic peptide has two N-methylations. According to other embodiments, the N-methylated cyclic peptide comprises 3, 4, or 5 N-methylations.

According to some embodiments, the N-methylations are in a position selected from the group consisting of (1,5), (1,6), (3,5), and (5,6), wherein the peptide comprises an amino acid in D configuration at position number 1.

According to some embodiments, the N-methylated cyclic peptide comprises at least two alanine residues. According to certain embodiments, the N-methylated cyclic peptide comprises two alanine residues. According to additional embodiments, the N-methylated cyclic peptide comprises three alanine residues. According to other embodiments, the N-methylated cyclic peptide comprises one alanine residue.

According to some embodiments, the N-methylated cyclic peptide comprises an amino acid in the D configuration. According to certain embodiments, the N-methylated cyclic peptide comprises an alanine residue in D configuration. According to additional embodiments, the N-methylated cyclic peptide comprises a glycine residue in the D configuration. According to additional embodiments, the N-methylated cyclic peptide comprises a valine residue in the D configuration. According to additional embodiments, the N-methylated cyclic peptide comprises a phenylalanine residue in the D configuration.

According to some embodiments, the N-methylated cyclic peptide comprises (3-amino acid, γ-amino acid, and/or D-amino acid. Each possibility represents a separate embodiment of the invention.

According to some embodiments, the N-methylated cyclic peptide comprises a hydrophobic amino acid. According to certain embodiments, the hydrophobic amino acids is selected from the group consisting of valine and phenylalanine.

According to some embodiments, the N-methylated cyclic peptide sequence is selected from the group consisting of:
(i) *rGDA*AA (peptide #5);
(ii) *aRGDA*A (peptide #12);
(iii) rG*DA*AA (peptide #17);
(iv) rGDA*A*A (peptide #23);
(v) *vRGDA*A (peptide #29);
(vi) *fRGDA*A (peptide #30);
(vii) *rGDA*AV (peptide #32); and
(viii) *rGDA*AF (peptide #33);

wherein * is N-methylation of the followed amino acid, R is arginine, G is glycine, D is aspartic acid, r is arginine in the D configuration, A is alanine, a is alanine in the D configuration, V is valine, v is valine in the D configuration, F is phenylalanine, and f is phenylalanine in the D configuration. Each possibility represents a separate embodiment of the invention.

According to some embodiments, the N-methylated cyclic peptide sequence is *rGDA*AA (peptide #5), wherein * is N-methylation of the followed amino acid, G is glycine, D is aspartic acid, r is arginine in the D configuration, A is alanine.

According to some embodiments, the N-methylated cyclic peptide sequence is *aRGDA*A (peptide #12), wherein * is N-methylation of the followed amino acid, R is arginine, G is glycine, D is aspartic acid, A is alanine, a is alanine in the D configuration.

According to some embodiments, the N-methylated cyclic peptide sequence is *vRGDA*A (peptide #29), wherein * is N-methylation of the followed amino acid, R is arginine, G is glycine, D is aspartic acid, A is alanine, v is valine in the D configuration.

Also included in the scope of the present invention are conjugates and fusion proteins comprising at least one N-methylated cyclic peptide according to the invention.

According to some embodiments, the N-methylated cyclic peptide is linked to at least one molecule that masks the charge of the amino acids. According to additional embodiments, the N-methylated cyclic peptide is linked to at least one molecule that reduces the net charge of the peptide.

According to some embodiments, the analog comprises modification selected from the group consisting of: 1-2 deletions of amino acids, 1-3 substitutions of amino acids, 1-2 additions of amino acids, addition of a linker, and combinations thereof. Each possibility represents a separate embodiment of the present invention.

According to some embodiments, the N-methylated cyclic peptide of the invention has high affinity to integrins. According to some embodiments, the N-methylated cyclic peptide of the invention is suitable for oral administration.

Prodrugs

According to an aspect, the present invention provides a prodrug comprising the N-methylated cyclic peptide described herein and a permeability enhancing moiety.

According to some embodiments, the peptide is an N-methylated cyclic hexapeptide or an analog thereof, comprising the sequence RGD and at least one alanine residue, wherein R is arginine residue (Arg) or a modified arginine residue, G is glycine residue (Gly) or a modified glycine residue, and D is aspartic acid (Asp) or a modified aspartic acid residue. According to specific embodiments, the N-methylated cyclic hexapeptide comprising the sequence RGD, wherein R is arginine residue (Arg), G is glycine residue (Gly), and D is aspartic acid (Asp).

According to some embodiments, the N-methylated cyclic hexapeptide comprises a plurality of N-methylations. According to certain embodiments, the N-methylated cyclic hexapeptide has two N-methylations. According to other embodiments, the N-methylated cyclic hexapeptide comprises 3, 4, or 5 N-methylations.

According to some embodiments, the N-methylated cyclic hexapeptide comprises at least two alanine residues. According to certain embodiments, the N-methylated cyclic hexapeptide comprises two alanine residues. According to additional embodiments, the N-methylated cyclic hexapeptide comprises three alanine residues.

According to some embodiments, the N-methylated cyclic hexapeptide comprises an amino acid in the D configuration. According to certain embodiments, the N-methylated cyclic hexapeptide comprises an alanine residue in the D configuration. According to additional embodiments, the N-methylated cyclic hexapeptide comprises a glycine residue in the D configuration. According to additional embodiments, the N-methylated cyclic hexapeptide comprises a valine residue in the D configuration. According to additional embodiments, the N-methylated cyclic hexapeptide comprises a phenylalanine residue in the D configuration.

According to some embodiments, the N-methylated cyclic hexapeptide sequence is selected from the group consisting of SEQ ID Nos: 1, 2, 3, 4, 5, 6, 7, and 8.

According to some embodiments, the permeability-enhancing moiety is coupled to the peptide's sequence directly or through a spacer or linker. The spacer or linker may comprise a protease-specific cleavage site.

According to some embodiments, the prodrug comprises the N-methylated cyclic peptide and at least one —CO$_2$R moiety.

According to some embodiments, the at least one —CO$_2$R moiety is covalently linked to a nitrogen atom of at least one amino acid side chain of the N-methylated cyclic hexapeptide. According to some embodiments, the at least one —CO$_2$R moiety is covalently linked to a nitrogen atom of at least one arginine side chain of the N-methylated cyclic hexapeptide. According to some embodiments, the prodrug comprises the moiety:

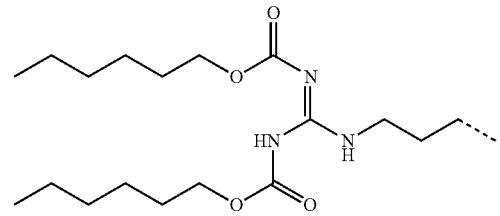

where the broken line indicates a covalent bond between the moiety and the backbone of the N-methylated cyclic hexapeptide. According to some embodiments, the broken line represents a covalent bond between the moiety and an α-carbon of the N-methylated cyclic hexapeptide.

According to some embodiments, R is a primary alkyl group. According to some embodiments, R is n-hexyl. According to other embodiments, R is n-C$_{14}$H$_{29}$ (myristyl).

According to some embodiments, the permeability-enhancing moiety is an oxycarbonyl moiety.

According to some embodiments, the permeability-enhancing moiety is a hexyloxycarbonyl (Hoc) moiety.

According to some embodiments, the guanidine group of Arg is masked with a hexyloxycarbonyl (Hoc) moiety. According to specific embodiments, the guanidine group of Arg is masked with two hexyloxycarbonyl (Hoc) moieties.

According to some embodiments, the cyclic peptide is linked to methyl ester (OMe)

According to some embodiments, the carboxylic side chain of the Asp residue is linked to OMe.

According to some embodiments, the prodrug has a formula selected from the group consisting of peptide 29P (c(*vR(Hoc)$_2$GD(OMe)A*A)), peptide 12P (c(*aR(Hoc)$_2$GD(OMe)A*A)), peptide 5P (c(*r(Hoc)$_2$GD(OMe)

A*AA), and peptide 23P (c(*r(Hoc)$_2$GD(OMe)A*A*A). Each possibility represents a separate embodiment of the invention.

According to some embodiments, the N-methylated cyclic peptide binds to integrins. According to certain embodiments, the N-methylated cyclic peptide binds with high affinity to the integrin αvβ3.

In some embodiments there is provided a process for preparing the prodrug, the process comprising:
(a) providing a peptide precursor;
(b) coupling said peptide precursor with a modified amino acid having the formula:

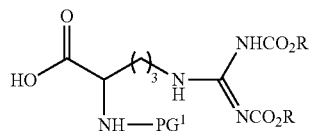

wherein
R is as defined herein;
PG$^1$ is a base-labile protecting group;
wherein the peptide precursor is selected from the group consisting of: an amino acid, a peptide and a solid phase resin;
(c) removing said base-labile protecting group PG' from the product of step (b) under basic conditions; and
(d) optionally coupling at least one additional amino acid; thereby forming the prodrug.

In some embodiments said peptide precursor comprises a solid phase resin. In some embodiments said peptide precursor is a solid phase resin having at least one amino acid residue. In some embodiments the process further comprises a step of removing the prodrug from the solid phase resin.

In some embodiments the process further comprises a step of reacting the peptide of step (a) or the prodrug of step (b) with an alcohol in the presence of an esterification reagent. In some embodiments the process further comprises the step of reacting the prodrug with an alcohol in the presence of thionyl chloride.

It is to be understood that esterification of the prodrug, or its precursor, may lead to capping and charge masking of carboxylic acid-containing side chains of the cyclic peptide. For example, esterification of an aspartic acid containing cyclic peptide with an alcohol in the presence of thienyl chloride may lead to formation of a —CH$_2$COOR$^4$ side chain, wherein R$^4$ is representing an alkyl fragment of the alcohol.

In some embodiments, said prodrugs are generally characterized by two main chemical features: (a) reduction or omission of electrically charged atoms in the peptide skeleton, e.g. through charge masking of charged amino acid residues and terminal amino and carboxylate moieties; and (b) improved lipophilicity provided through introduction of lipophilic groups. A further feature presented by peptide-based prodrugs prepared according to some embodiments of the present processes is their lability in the presence of cellular enzymes, which transform the prodrugs into charged biologically active peptide drugs.

The term "prodrug" as used herein refers to an inactive or relatively less active form of an active agent that becomes active through one or more metabolic processes in a subject.

The term "masking moiety" as used herein refers to a moiety that reduce the net electric charge of the peptide such as Hexyloxycarbonyl (Hoc).

A common feature to processes for producing the prodrugs disclosed herein, according to some embodiments, is the modification of amino acids and/or amino acid residues to their modified counterparts, which include an ester(s) and/or carbamate(s) of primary alcohols. In some embodiments and generally, amino side chains having amine moieties are transformed into carbamates having —NHCO$_2$R moieties; whereas amino side chains having carboxylate moieties are transformed into esters having —CO$_2$R moieties. In some embodiments, since the esters and amines are of primary alcohols, R is primary, i.e. the first group covalently bonded to the carbonyl's sp$^3$ oxygen is a methylene group.

The present invention is based in part on the finding that unlike tertiary carbamates, primary carbamates do not transform into their corresponding amines or ammonium ions until after penetrating the intestine membrane and reaching the circulation, the target tissue or the target cell, where specific proteases are present. Without wishing to be bound by any theory or mechanism of action, the commonly used tertiary carbamates (e.g. compound having the tert-butyloxycarbonyl-amino, N—CO$_2$CMe$_3$ moiety, N—BOC) undergo O—CMe$_3$ bond cleavage in gastrointestinal pH. In contrast, primary alkyl carbamates, of the prodrugs of the present invention, are relatively stable until after penetrating through the intestine membrane and reach the circulation, the lymphatic system, and/or the blood stream. Therefore, tertiary carbamates undergo O—CMe$_3$ bond cleavage before reaching the circulation or target tissue, to form the corresponding carbamic acids (having a —NH—CO$_2$H group), which undergo spontaneous decarboxylation to form amines. Said amines are then being protonated under gastrointestinal pH to form charged peptides which undergo degradation before reaching the cells. On the other hand, it was surprisingly found that a similar sequence of reactions, occurs with primary carbamates only in the presence of specific esterases, which target and break the O—CH$_2$ or the carbonyl-OCH$_2$ bond in the blood stream, lymphatic system, target tissue or inside the target cell.

In some embodiments, some the processes disclosed herein are distinctive in the stage in which the modification occurs. Whereas in some of the processes a modification is performed on an amino acid prior to its incorporation to the prodrug in a peptide synthesis; in some processes the modification is performed on an amino acid residue during the peptide synthesis; and in some of the processes the modification is preformed after the completion of the peptide synthesis.

The amino acids used in this invention are those which are available commercially or are available by routine synthetic methods. Certain residues may require special methods for incorporation into the peptide, and either sequential, divergent or convergent synthetic approaches to the peptide sequence are useful in this invention. Natural coded amino acids and their derivatives are represented by three-letter codes according to IUPAC conventions.

Conservative substitution of amino acids as known to those skilled in the art are within the scope of the present invention. Conservative amino acid substitutions include replacement of one amino acid with another having the same type of functional group or side chain e.g. aliphatic, aromatic, positively charged, negatively charged. These substitutions may enhance oral bioavailability, affinity to the target protein, metabolic stability, penetration into the central nervous system, targeting to specific cell populations and the like. One of skill will recognize that individual substitutions, deletions or additions to peptide sequence which alters, adds or deletes a single amino acid or a small percentage of amino acids is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), methionine (M), Valine (V); and
6) Phenylalanine (F), Tyrosine (Y), Tryptophan (W).

Also included within the scope of the invention are salts of the peptides, analogs, and chemical derivatives of the peptides of the invention.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides of the present invention may be produced by any method known in the art, including recombinant and synthetic methods. Synthetic methods include exclusive solid phase synthesis, partial solid phase synthesis, fragment condensation, or classical solution synthesis. Solid phase peptide synthesis procedures are well known to one skilled in the art and described, for example by John Morrow Stewart and Janis Dillaha Young, Solid Phase Polypeptide Syntheses (2nd Ed., Pierce Chemical Company, 1984). In some embodiments, synthetic peptides are purified by preparative high-performance liquid chromatography (Creighton T. (1983) Proteins, structures and molecular principles. WH Freeman and Co. N.Y.).

Pharmaceutical Compositions

According to an aspect, the present invention provides a pharmaceutical composition comprising as an active ingredient the N-methylated cyclic peptide or the prodrug according to the invention. According to some embodiments, the pharmaceutical composition further comprises a pharmaceutically acceptable carrier, excipient or diluent.

According to some embodiments, the composition is formulated for an oral administration. According to some embodiments, the composition is formulated for oral administration as a liquid or solid dosage form for immediate, slow, delayed or sustained-release characteristics.

According to some embodiments, the pharmaceutical composition comprises absorption enhancers. According to some embodiments, the pharmaceutical composition further comprises lipids. According to some embodiments, the pharmaceutical composition further comprises self nano-emulsifying drug delivery systems (SNEDDS). According to certain embodiments, the pharmaceutical composition comprises Pro-NanoLiposphere (PNL).

According to some embodiments, the pharmaceutical composition comprises curcumin, resveratrol and/or piperine. According to some embodiments, the pharmaceutical composition comprises Resveratrol-PNL and/or Piperine-PNL.

According to some embodiments, the pharmaceutical composition comprises elements that reduce intra-enterocyte metabolism by CYP3A4 enzymes and/or reduce P-gp efflux activity.

According to some embodiments, the pharmaceutical composition comprises verapamil.

The term SNEDDS (self nano-emulsifying drug delivery systems) as used herein refers to anhydrous homogeneous liquid mixtures, composed of oil, surfactant, drug, and/or cosolvents, which spontaneously form transparent nanoemulsion [13].

The term PNL (Pro-NanoLiposphere) as used herein refers to a delivery system based on a solution containing the drug, triglyceride, phospholipid, surfactants, and a water miscible organic solvent [30].

In another aspect, the present invention provides a pharmaceutical composition for use in treating cancer, the pharmaceutical composition comprises as an active ingredient the N-methylated cyclic peptide or prodrug according to the invention.

In another aspect, the present invention provides a method of treating integrin-related condition or disease, the method comprising administering to a subject in need thereof, a therapeutically effective amount of the pharmaceutical composition described hereinabove. According to some embodiments, the disease is angiogenesis-related disease or disorder.

In another aspect, the present invention provides a method of treating cancer, the method comprising administering to a subject in need thereof, a therapeutically effective amount of the pharmaceutical composition described hereinabove, thereby treating cancer in the subject.

According to some embodiments, the cancer is glioblastoma.

According to some embodiments, the route of administration of the composition is orally.

According to some embodiments, the N-methylated cyclic hexapeptide reduces integrin activity.

According to some embodiments, the N-methylated cyclic hexapeptide is capable of recognizing integrins.

The pharmaceutical composition according to the present invention may be administered as a standalone treatment or in addition to a treatment with any other known treatments for cancer. According to some embodiments, the other treatment is chemotherapy.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antioxidants such as ascorbic acid or sodium bisulfite; chelating agents such as ethylenediaminetetraacetic acid; and agents for the adjustment of tonicity such as sodium chloride or dextrose are also envisioned.

The compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the peptides according to the invention, preferably in a substantially purified form, together with a suitable amount of carrier so as to provide the form for proper administration to the subject.

The amount of the peptides which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the seriousness of the disease or disorder, and should be decided according to the judgment of the practitioner and each patient's circumstances.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule, age, body weight, sex, or conditions of the patient, it will be determined by the physician in the end. The dosage can be administered, for example, in weekly, biweekly, monthly or bimonthly regimens. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

According to some embodiments, the peptides can be administered in combination with at least one chemotherapeutic agent. The peptides and the chemotherapeutic agent can be administered according to an overlapping schedule. According to some embodiments, the administering of the peptides and of the at least one chemotherapeutic agent is carried out substantially simultaneously, concurrently, alternately, sequentially or successively.

Suitable dosing regimens of combination chemotherapies are known in the art and described in, for example, Saltz et al. Proc ASCO 1999; 18:233a and Douillard et al., Lancet 2000, 355, 1041-7.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

Toxicity and therapeutic efficacy of the peptides described herein can be determined by standard pharmaceutical procedures in cell cultures or experimental animals, e.g., by determining the IC50 (the concentration which provides 50% inhibition) and the LD50 (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition.

The preferred doses for administration of such pharmaceutical compositions range from about 0.1 μg/kg to about 20 mg/kg body weight. Preferably, the amount of the active ingredient is in the range of from about 10 to 5000 μg/kg.

In some embodiments, the peptides of the invention are administered at a dose ranging from about 20 ng/kg to about 100 ng/kg of the subject weight. In other embodiments, the peptide of the invention is administered at a dose ranging from about 0.1 mg/kg to about 10 mg/kg of the subject weight. In yet other embodiments, the peptide of the invention is administered at a dose ranging from 0.1, 1, 10, 20, 30, 50, 100, 200, 400, 500, 700, 900 or 1000 ng/kg of the subject weight, to about 100, 200, 400, 500, 700, 900, 1000, 1200, 1400, 1700, or 2000 ng/kg of the subject weight. Each possibility represents a separate embodiment of the invention. In yet other embodiments, the peptide of the invention is administered at a dose ranging from about 0.01, 0.05, 0.1, 0.5, 0.7, 1, or 2 mg/kg of the subject weight, to about 0.05, 0.1, 0.5, 0.7, 1, 2, 5, 10, 15, 20, 50, 100, 250, or 500 mg/kg of the subject weight. Each possibility represents a separate embodiment of the invention.

According to some embodiments, the peptide is orally administered at a dose ranging from about 0.001 mg/kg to about 500 mg/kg of the subject weight, for example from about 0.1 mg/kg to about 500 mg/kg of the subject's body weight.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Material and Methods
Chromatography

Semi-preparative reversed phase HPLC was performed using Waters instruments: Waters 2545 (Binary Gradient Module), Waters SFO (System Fluidics Organizer), Waters 2996 (Photodiode Array Detector), Waters 2767 (Sample Manager). Dr. Maisch C18-column: Reprosil 100 C18, 5 μm, 150×30 mm was used. The Semi-preparative RP-HPLC were operated with a flow rate of 40 mL/min with a linear gradient (20 min) of $H_2O$ (0.1% v/v trifluoroacetic acid (TFA)) and acetonitrile (0.1% v/v TFA). Analytical HESI-HPLC-MS (heated electrospray ionization mass spectrometry) was performed on a LCQ Fleet (Thermo Scientific) with a connected UltiMate 3000 UHPLC focused (Dionex) on C18-columns: 51: Hypersil Gold aQ 175 Å, 3 μm, 150×2.1 mm (for 8 or 20 minutes measurements); S2: Accucore C18, 80 Å, 2.6 μm, 50×2.1 mm (for 5 minute measurements) (Thermo Scientific). Linear gradients (5%-95% acetonitrile content) with $H_2O$ (0.1% v/v formic acid) and acetonitrile (0.1% v/v formic acid) as eluents were used.

NMR

All NMR resonances were assigned in DMSO-d6 at 298 K (except the temperature gradient resonances) and at proton resonance frequency of 400 MHz or 500 MHz. Chemical shifts are referenced to the DMSO 1H resonance at 2.50 ppm and the DMSO 13CMe resonance 39.51 ppm.

Synthesis of Cyclic Peptides

Loading of CTC-resin. Peptide synthesis was carried out using CTC-resin (0.9 mmol/g) following standard Fmoc-strategy. Fmoc-Xaa-OH (1.2 eq.) were attached to the CTC-resin with N,N-diisopropylethylamin (DIEA; 2.5 eq.) in anhydrous DCM (0.8 mL/g resin) at room temperature (rt) for 1 h. The remaining trityl-chloride groups were capped by addition of a solution of MeOH (1 mL/g (resin)), DIEA (5:1; v:v) for 15 min. The resin was filtered and washed 5 times with DCM and 3 times with MeOH. The loading capacity was determined by weight after drying the resin under vacuum and ranged from 0.4-0.9 mmol/g.

On-resin Fmoc-Deprotection. The Fmoc peptidyl-resin was treated with 20% piperidine in NMP (v/v) for 10 minutes and a second time for 5 minutes. The resin was washed 5 times with NMP.

Standard Amino Acid Coupling. A solution of Fmoc-Xaa-OH (2 eq.), O-(7-azabenzotriazole-1yl)-N,N,N',N'-tetramethyluronium-hexafluorophosphate (HATU) (2 eq.), 1-hydroxy-7-azabenzotriazole (HOAt; 2 eq.), and DIEA (3 eq.) in NMP (1 mL/g resin) was added to the free amino peptidyl-resin and shaken for 60 min at room temperature and washed 5 times with NMP.

On-Resin N-Methylation. The linear Fmoc-deprotected peptide was washed with DCM (3×) incubated with a solution of 2-nitrobenzenesulfonylchloride (o-Ns-Cl, 4 eq.) and 2,4,6-Collidine (10 eq.) in DCM for 20 min at room temperature. The resin was washed with DCM (3×) and THF abs. (5×). A solution containing PPh3 (Seq.) and MeOH abs. (10 eq.) in THF abs. was added to the resin. DIAD (5 eq.) in a small amount THF abs. is added stepwise to the resin and the solution was incubated for 15 min and washed with THF (5×) and NMP (5×). For o-Ns deprotection, the o-Ns-peptidyl-resin was stirred in a solution of mercaptoethanol (10 eq.) and DBU (5 eq.) in NMP (1 mL/g resin) for 5 minutes. The deprotection procedure was repeated once more and the resin was washed 5 times with NMP.

Cleavage of Linear Peptides from Resin. For complete cleavage from the resin the peptides were treated three times with a solution of DCM and hexafluoroisopropanol (HFIP; 4:1; v:v) at room temperature for half an hour and the solvent evaporated under reduced pressure.

Cyclization with Diphenylphosphoryl Azide (DPPA). To a solution of peptide in DMF (1 mM peptide concentration) and $NaHCO_3$ (5 eq.) DPPA (3 eq.) was added at room temperature (rt) and stirred over night or until no linear peptide could be observed by HPLC-MS. The solvent was evaporated to a small volume under reduced pressure and the peptides precipitated in saturated NaCl solution and washed two times in HPLC grade water.

Removal of Acid Labile Side Chain Protecting Group. Cyclized peptides were stirred in a solution of TFA, water and TIPS (95:2.5:2.5) at room temperature for one hour or until no more protected peptide could be observed by HPLC-MS and precipitated in diethylether. The precipitated peptide was collected after centrifugation and decantation. This precipitated peptide was washed with diethylether and collected two more times.

Dde-Deprotection in Solution. The orthogonal deprotection of the Dde-protecting group (1-(4,4-dimethyl-2,6-dioxocyclohex-1-ylidene)ethyl) was performed using 2 vol % solution of hydrazine hydrate in dimethylformamide (DMF) for 30 min at room temperature. The progress of the reaction was monitored by HPLC-MS. After completion of the reaction, the peptide was precipitated with sat. aq. NaCl-solution and washed two times with water.

Guanidinylation in Solution. The Dde-deprotected peptide were stirred in a solution of 1H-Pyrazole-carboxamidine-hydrochloride (2.0 eq.) and DIEA (3.0 eq.) at room temperature for 12 hours. The progress of the reaction was controlled via HPLC-MS. After completion, the solvent was removed under reduced pressure.

Reductive Deprotection. The orthogonal deprotection of the benzyl-group via hydrogenolysis was performed using a palladium catalyst on activated carbon (10% Pd/C with 50% $H_2O$ as stabilizer, 15 mg/mmol) and hydrogen atmosphere (1 atm. H2) at room temperature. The completion of the deprotection was monitored by HPLC-MS, the catalyst was removed over diatomaceous earth and the solvent was removed under pressure.

Synthesis of Hoc-Protected Arginine

Trimethylsilyl (TMS) Protection of Carboxylic acid. To dry Fmoc-protected Arginie DCM and DIEA (4.eq.) was added under argon atmosphere. With continuous stirring TMSCl (4 eq.) was added in 2-4 portions to the solution and was stirred at 40° C. for 1.5 h with a refluxing condenser. This resulted in a TMS-protected Fmoc-Arginine.

Hexyloxycarbonyl (Hoc) Protection. The solution of TMS-protected Fmoc-Arginine was cooled to 0° C. and it was added DIEA (3 eq.) followed by the stepwise addition of hexyl chloroformiate (3 eq.). The solution was stirred at 0° C. for 30 mins, then raised to room temperature and was stirred overnight. The completion was confirmed by HPLC-MS.

Removal of TMS. The reaction contents were acidified by addition of 1N HCl until the pH of the organic layer was 2 and hence the deprotection of the TMS group. The compound, Fmoc-Arg(Hoc)$_2$-OH, was extracted with DCM (3-5×), the extracts were then combined, dried with MgSO4 and DCM was removed afterwards under reduced pressure. The final product was obtained after crystallization from a solution of methanol and water (4:1; v/v) and was confirmed by HPLC-MS.

Integrin Binding Assay

The activity and selectivity of integrin ligands were determined by a solid-phase binding assay, applying a previously described protocol [11, 12], using coated extracellular matrix proteins and soluble integrins. The following compounds were used as internal standards: Cilengitide, c(f(NMe)VRGD) (αvβ3-0.54 nM, αvβ5-8 nM, α5β1-15.4 nM), linear peptide RTDLDSLRT4 (αvβ6-33 nM; αvβ8-100 nM)(SEQ ID NO:24) and tirofiban5 (αIIbβ3-1.2 nM). Flat-bottom 96-well ELISA plates (BRAND, Wertheim, Germany) were coated overnight at 4° C. with the ECM-protein (1) (100 μL per well) in carbonate buffer (15 mM $Na_2CO_3$, 35 mM $NaHCO_3$, pH 9.6). Each well was then washed with PBS-T-buffer (phosphate-buffered saline/Tween20, 137 mM NaCl, 2.7 mM KCl, 10 mM $Na_2HPO_4$, 2 mM $KH_2PO_4$, 0.01% Tween20, pH 7.4; 3×200 μL) and blocked for 1 h at room temperature (rt) with TS-B-buffer (Tris-saline/BSA buffer (bovine serum albumin); 150 μL/well; 20 mM Tris-HCl, 150 mM NaCl, 1 mM $CaCl_2$), 1 mM $MgCl_2$, 1 mM $MnCl_2$, pH 7.5, 1% BSA). In the meantime, a dilution series of the compound and internal standard is prepared in an extra plate, starting from 20 μM to 6.4 nM in 1:5 dilution steps. After washing the assay plate three times with PBS-T (200 μL), 50 μl of the dilution series were transferred to each well from B-G. Well A was filled with 100 μl TSB-solution (blank) and well H was filled with 50 μl TS-B-buffer. 50 μl of a solution of human integrin (2) in TS-B-buffer was transferred to wells H-B and incubated for 1 h at room temperature (rt). The plate was washed three times with PBS-T buffer, and then primary antibody (3) (100 μL per well) was added to the plate. After incubation for 1 h at rt, the plate was washed three times with PBS-T. Then, secondary peroxidase-labeled antibody (4) (100 μL/well) was added to the plate and incubated for 1 h at rt. After washing the plate three times with PBS-T, the plate was developed by quick addition of SeramunBlau (50 μL per well, Seramun Diagnostic GmbH, Heidesee, Germany) and incubated for 5 min at room temperature in the dark. The reaction was stopped with 3 M $H_2SO_4$ (50 μL/well), and the absorbance was measured at 405 nm with a plate reader (GENios, TECAN).

The $IC_{50}$-value of each compound was tested in duplicate and the resulting inhibition curves were analyzed using OriginPro 9.0G software. The inflection point describes the $IC_{50}$-value. All determined $IC_{50}$-values were referenced to the activity of the internal standard.

αvβ3
(1) 1.0 μg/mL human vitronectin; Millipore.
(2) 2.0 μg/mL, human αvβ3-integrin, R&D.
(3) 2.0 μg/mL, mouse anti-human CD51/61, BD Biosciences.
(4) 2.0 μg/mL, anti-mouse IgG-POD, Sigma-Aldrich.
α5β1
(1) 0.5 μg/mL; human fibronectin, Sigma-Aldrich.
(2) 2.0 μg/mL, human α5β1-integrin, R&D.
(3) 1.0 μg/mL, mouse anti-human CD49e, BD Biosciences.
(4) 2.0 μg/mL, anti-mouse IgG-POD, Sigma-Aldrich.
αvβ5
(1) 5.0 μg/mL; human vitronectin, Millipore.
(2) 3.0 μg/mL, human αvβ5-integrin, Millipore.
(3) 1:500 dilution, anti-αv mouse anti-human MAB1978, Millipore.
(4) 1.0 μg/mL, anti-mouse IgG-POD, Sigma-Aldrich.
αvβ6
(1) 0.4 μg/mL; LAP (TGF-β), R&D.
(2) 0.5 μg/mL, human αvβ6-Integrin, R&D.
(3) 1:500 dilution, anti-αv mouse anti-human MAB1978, Millipore.
(4) 2.0 μg/mL, anti-mouse IgG-POD, Sigma-Aldrich.
αvβ8
(1) 0.4 μg/mL; LAP (TGF-b), R&D.
(2) 0.5 μg/mL, human αvβ8-Integrin, R&D.
(3) 1:500 dilution, anti-αv mouse antihuman MAB1978, Millipore.
(4) 2.0 μg/mL, anti-mouse IgG-POD, Sigma-Aldrich.
αIIbβ3
(1) 10.0 μg/mL; human fibrinogen, Sigma-Aldrich.
(2) 5.0 μg/mL, human platelet integrin αIIbβ3, VWR.
(3) 2.0 μg/mL, mouse anti-human CD41b, BD Biosciences.
(4) 1.0 μg/mL, anti-mouse IgG-POD, Sigma-Aldrich.

Permeability Study

Culture of colorectal adenocarcinoma 2 (Caco-2) cells. Caco-2 cells (ATTC) were grown in 75 $cm^2$ flasks with approximately $0.5×10^6$ cells/flask (Thermo-Fischer) at 37° C. in a 5% $CO_2$ atmosphere and at relative humidity of 95%. The culture growth medium consisted of DMEM supplemented with 10% heat-inactivated FBS, 1% MEM-NEAA, 2 mM 1-glutamine, 1 mM sodium pyruvate, 50,000 units Penicillin G Sodium and 50 mg Streptomycin Sulfate (Biological Industries). The medium was replaced every other day.

Caco-2 cells growth and treatment. Cells (passage 55-60) were seeded at density of $25×10^5$ cells/$cm^2$ on untreated culture inserts of polycarbonate membrane with 0.4 μm pores and surface area of 1.1 $cm^2$. Culture inserts containing Caco-2 monolayer were placed in 12 mm transwell plates (Corning). Culture medium was replaced every other day. Transepithelial Electrical Resistance (TEER) values were measured by Millicell ERS-2 System (Millipore) a week after seeding up to experiment day (21-23 days) to ensure proliferation and differentiation of the cells. When the cells were fully differentiated and TEER values became stable (200-500 $Ω·cm^2$). The TEER values were compared to control inserts containing only the medium.

In vitro permeability studies using Caco-2 cells. The experiment was initiated by replacing the medium from both sides by apical (600 μl) and basolateral (1500 μl) buffers, both warmed to 37° C. The Cells were incubated with the buffers solutions for 30 min at 37° C. on a shaker (100 cycles/min). The apical buffer was replaced by apical buffer containing 10 μg/ml of the cyclic peptides of the invention. 50 μl samples were taken from the apical side immediately at the beginning of the experiment, resulting in 550 μl apical volume during the experiment. Samples of 200 μl at fixed time points (20, 40, 60, 80, 100, 120 and 150 min) from the basolateral side and replaced with the same volume of fresh basolateral buffer to maintain a constant volume. The experiment included two control compounds, atenolol and metoprolol, as paracellular and transcellular permeability markers.

Caco-2 permeability study data analysis. Permeability Coefficient (Papp) for each compound was calculated from the linear plot of drug accumulated versus time, using the following equation:

$$Papp = \frac{dq/dt}{C_0 \times A}$$

Where dq/dt is steady state appearance rate of the compound on the receiver side, Co is the initial concentration of the drug on the donor side, and A is the exposed tissue surface area (1.1 cm$^2$).

Enzymatic inhibition studies. For the determination of enzymatic inhibition by the self-nano emulsifying drug delivery system (SNEDDS) [13] or ketoconazole, pooled rat CYP3A4 microsomes (BD Biosciences, Woburn, MA, USA) were used. The reaction was initiated by adding ice cold microsomes (0.5 mg/mL final concentration) to a preheated phosphate buffer (0.1M, pH 7.4) containing NADPH (0.66 mg/mL) and dispersed 12P-SNEDDS (2.8 μL, equivalent to 12P 1 μM), with ketoconazole (3 μM) or 12P alone (1 μM). At predetermined times (0, 15, and 30 min), 50 μL samples were withdrawn, and the reaction was terminated by adding 100 μL of ice cold ACN and further processed as described in the Analytical Methods section below.

In Vivo Studies. Male Wistar rats (Harlan, Israel), 275-300 g in weight, were used for all surgical procedures. Animals were anesthetized for the period of surgery by intraperitoneal injection of 1 mL/kg of ketamine/xylazine solution (9:1), placed on a heated surface, and maintained at 37° C. (Harvard Apparatus Inc., Holliston, MA). An indwelling cannula was placed in the right jugular vein of each animal for systemic blood sampling, by a method described before. The cannula was tunneled beneath the skin and exteriorized at the dorsal part of the neck. After completion of the surgical procedure, the animals were transferred to cages to recover overnight (12-18 h). During this recovery period, food but not water was deprived. Throughout the experiment, free access to food was available 4 h post oral administration. Animals were randomly assigned to the different experimental groups. For bioavailability studies, dispersed 12P SNEDDS was freshly prepared 30 min before each experiment by vortex-mixing of the preconcentrate in water (1:10, v/v) preheated to 37° C. for 30 s. Dispersed 12P SNEDDS (5 mg/kg) was administered to the animals by oral gavage (n=3). Systemic blood samples (0.35 mL) were taken at 5 min predose, 20, 40, 60, 90, 180, 240, and 360 min postdose. To prevent dehydration, equal volumes of physiological solution were administered to the rats following each withdrawal of blood sample. Plasma was separated by centrifugation (5322 g, 10 min) and stored at −20° C. pending analysis. In the 12P pharmacokinetic study, the parent peptide, 12, was analytically determined.

Pharmacokinetic Analysis. The area under the plasma concentration-time curve (AUC) was calculated by using the trapezoidal rule with extrapolation to infinity by dividing the last measured concentration by the elimination rate constant (kel). The elimination rate constant values were determined by a linear regression analysis using the last points on the logarithmic plot of the plasma concentration versus the time curve. Pharmacokinetic parameters, such Tmax, Cmax, clearance (CL), volume of distribution (V), and bioavailability, were calculated using noncompartmental analysis.

Analytical Methods. Plasma or BBMV samples were spiked with metoprolol (1.5 μg/mL) as an internal standard. ACN was added to each sample (2:1) and vortex-mixed for 1 min. The samples were then centrifuged (14 635 g, 10 min), and the supernatant was transferred to fresh glass tubes and evaporated to dryness (Vacuum Evaporation System, Labconco, Kansas City, MO, USA). Then, the glass tubes were reconstituted in 80 μL of mobile phase and centrifuged a second time (14 635 g, 10 min). The amount of the compounds was determined using an HPLC-MS Waters 2695 Separation Module, equipped with a Micromass ZQ detector. The resulting solution was injected (10 μL) into the HPLC system. The system was conditioned as follows: for parent drug peptides (including 12), a Kinetex 2.6 μm HILIC 100 Å, 100 mm×2.1 mm column (Phenomenex, Torrance, CA, USA), an isocratic mobile phase, and an acetonitrile:water:ammonium acetate buffer 50 mM (70:10:20, v/v/v) was used; and for the prodrug peptides (including 12P), a Luna (Phenomenex) 3 μm C8 100 Å, 100 mm×2.0 mm column and an isocratic mobile phase of ACN:water supplemented with 0.1% formic acid (70:30, v/v) and a flow rate of 0.2 mL/min at 25° C. was used. The limit of quantification for all of the peptides and prodrugs was 25 ng/mL.

Statistical Analysis. All values are expressed as mean±standard error of the mean (SEM) if not stated otherwise. To determine statistically significant differences among the experimental groups, a t-test or one-way ANOVA, followed by Tukey's test, was used. A p-value of less than 0.05 was termed significant.

Example 1: Screening of Peptide Libraries with Spatial Diversity for Highly Active and Selective RGD Containing N-Methylated Cyclic Hexapeptides The method as well as number and sequence of each peptide are depicted in the flowchart shown in FIG. 1.

Step 1. synthesis of combinatorial library of all possible N-methylated analogs of the stem peptide cyclo(D-Ala-Alas) (c(aAAAAA); SEQ ID NO: 19) and selection of the cyclic peptide with highest intestinal permeability.

Figure 2:
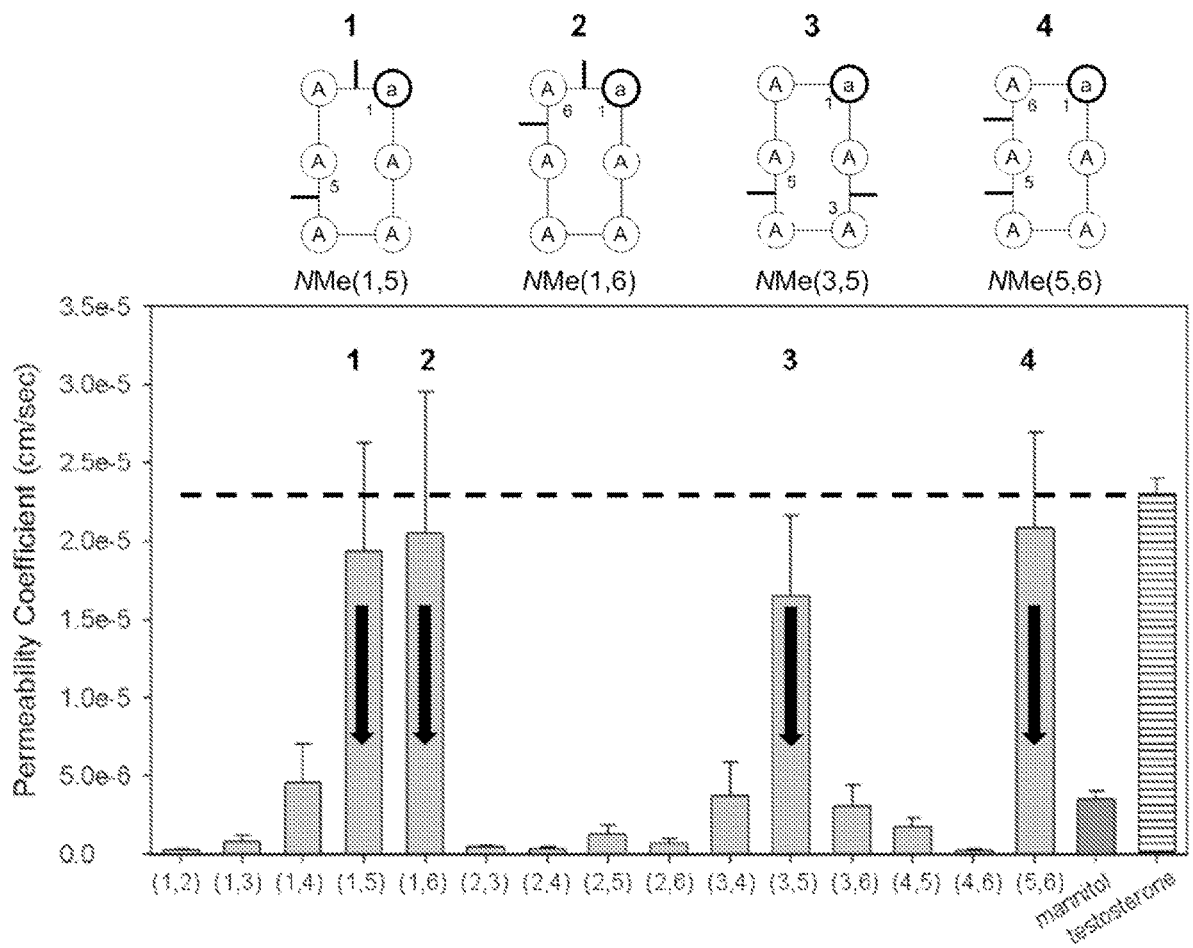
FIG. 2 shows structure-permeability relationship (SPR) of some of the members of the N-methylated cyclic Ala hexapeptides. The structures of the four highly Caco-2 permeable di-N-Methylated cyclic hexa-alanine peptide scaffolds (peptides #1, 2, 3, 4) are shown on the right.

The structure-permeability relationship (SPR) of a combinatorial library of 54 out of 63 possible all Ala cyclic hexapeptides c(aAAAAA)(SEQ ID NO: 19) with different N-methylation pattern was evaluated. The peptides with highest permeability were chosen as templates for designing RGD based peptides. It was found that these peptides strongly vary in permeability, some of them exhibiting an extremely high Caco-2 permeability or even higher comparable to the Caco-2 standard testosterone [10] (peptides 1-4, FIG. 2). It turned out that the permeability of cyclic hexapeptides is strongly dependent on their molecular structure [15,16] and clearly provide evidence that participation of a transporter is responsible for the high permeability of some of these peptides. We have shown that the Caco-2 permeability does not correlate with one single parameter such as i) the number of N-methylated amino acids, ii) the number of externally oriented NH groups [10] and iii) the lipophilicity. The peptides with the highest permeability turned out to be a subgroup of peptides with two N-methylation in distinct positions: the 1,5-; the 1,6-; the 3,5- and the 5,6-dimethylated peptide (Peptides 1-4, FIGS. 1 and 2) [9,10]. Another highly permeable peptide with a four N-methylation pattern (NMe 1,4,5,6) was not used as a scaffold since it is chemically less stable and synthetically more difficult to prepare.

Step 2. Synthesis of sub-libraries of each of the selected cyclic peptide that includes the RGD sequence in all possible positions.

The most permeable scaffolds (peptides #1 to #4, FIGS. 1 and 2) were used for the construction of second generation combinatorial sub-libraries in which Ala side chains were replaced by side chains of amino acids derived from the active regions of peptides or proteins. The three consecutive C$^\alpha$ methyl groups were systematically replaced (or omitted for G) by the RGD side chains. This manipulation allows the presentation of the RGD side chains in very different spatial orientations that are impossible to predict from the knowledge of several X-ray structures of integrin head groups with bound peptidic ligands [17-20].

Step 3. Selection of the best ligands for RGD-recognizing integrin subtypes.

Twenty-four RGD cyclic peptides (#5 to #28 in FIG. 1) were screened for their binding to various RGD binding integrins. Few compounds were selected, showing low nanomolar affinity for binding to the integrin subtype αvβ3 and only one to two orders of magnitude lower affinity for α5β1. This is remarkable as linear RGD containing peptides usually bind with some affinity also to some of the other RGD binding integrins (αvβ5, αvβ6, αvβ8 and αIIbβ3) [21]. One exception is the family of the (3,5)-NMe peptides (Peptide #17-22) that show low affinity for all integrin subtypes. The parent (3,5)-NMe all Ala peptide (peptide #3 in FIG. 1) exhibited two conformations in the NMR spectrum (in DMSO solution), in contrast to the 1,5- and 1,6-dimethylated parent peptides (peptides #1 and #2 in FIG. 1) that are conformational homogeneous on the NMR time scale. Obviously the two conformations of peptide #3 are cis/trans isomers around one or more peptide bonds.

tripeptide sequence. Indeed, the introduction of a single carboxyl group (aspartic acid instead of Ala) or a single guanidinium group (Arg instead of Ala) in any position of peptide #1 (FIG. 1, altogether 2×6 peptides) reduced permeability completely. To enable intestinal and oral bioavailability of the RGD containing peptides selected in steps 3 and 4 it is essential to mask the charges of both Arg and Asp. For this purpose, the prodrug approach was applied, in which the charged residues are masked by lipophilic pro-moieties that are cleaved by esterases. The charge on the Asp residue masked with methyl ester pro-moiety, and the charge of the guanidium group of Arg masked with the dihexyloxy-carbonyl pro-moiety. Specifically, guanidine group of the Arg residue of the prodrug described in the following examples was masked with two hexyloxycarbonyl (Hoc) moieties and the carboxylic side chain of Asp was transformed into the neutrally charged methyl ester (OMe). Both lipophilic alkyl pro-moieties contain an ester bond. Thus, the prodrugs are readily converted to their original active peptide by ubiquitous esterases, that are present throughout the body.

TABLE 1

$IC_{50}$-values of peptide ligands for RGD-recognizing integrin subtypes αvβ3, αvβ5, αvβ6, α5β1.

| scaffold | peptide name or # | sequence | αvβ3, $IC_{50}$ [nM] | αvβ5, $IC_{50}$ [nM] | αvβ6, $IC_{50}$ [nM] | α5β1, $IC_{50}$ [nM] |
|---|---|---|---|---|---|---|
| | cilengitide | c(f*VRGD) | 0.61 ± 0.06 | 8.4 ± 2.1 | 2050 ± 640 | 15 ± 3 |
| NMe(1,5) | 5 | c(*rGDA*AA) | 13 ± 2 | 170 ± 30 | 25 ± 2.5 | 37 ± 4 |
| NMe(1,6) | 12 | c(*aRGDA*A) | 4.8 ± 1.8 | 1500 ± n.d. | 770 ± n.d. | 200 ± 60 |
| NMe(3,5) | 17 | c(rG*DA*AA) | 2350 ± 210 | >5000 | >10000 | >10000 |
| NMe(5,6) | 23 | c(rGDA*A*A) | 73 ± 15 | n.d. | 130 ± 11 | 76 ± 6 |
| NMe(1,6) | 29 | c(*vRGDA*A) | 0.6 ± 0.2 | 430 ± n.d. | 290 ± n.d. | 35 ± 5 |
| NMe(1,6) | 30 | c(*fRGDA*A) | 0.6 ± 0.2 | 145 ± n.d. | 120 ± n.d. | 21 ± 2 |
| NMe(1,5) | 33 | c(*rGDA*AF) | 4.4 ± 1.1 | n.d. | 25 ± 3 | 43 ± 4 |
| NMe(1,5) | 32 | c(*rGDA*AV) | 5.6 ± 1.8 | n.d. | 3.8 ± 0.6 | 20 ± 2 |

*cilengitide is SEQ ID NO: 20, peptide #5 is SEQ ID NO: 1, peptide #12 is SEQ ID NO: 2, peptide #17 is SEQ ID NO: 3, peptide #23 is SEQ ID NO: 4, peptide #29 is SEQ ID NO: 5, peptide #30 is SEQ ID NO: 6, peptide #32 is SEQ ID NO: 7, and peptide #33 is SEQ ID NO: 8.

Step 4. Selection of the best ligands by substitution of Ala to another amino acid for optimization of affinity and selectivity The next step was the optimization of the most active peptides by replacement of Ala residues flanking to the of RGD motif. It is known from many Structure Activity Relationship (SAR) studies that aromatic residues flanking the RGD sequence enhance affinity and selectivity towards members of the RGD recognizing integrin subfamily, see e.g. [22]. For example, substitution of the D-Ala residue in peptide 12 (SEQ ID NO: 2) by D-Phe and D-Val residues resulted in ligands (peptides 29 and 30, SEQ ID NO: 5 and 6, respectively) with subnanomolar affinity for αvβ3 with an almost two orders of magnitude lower affinity for α5β1 (Table 1). The affinity and selectivity of the new compounds are comparable or even better than Cilengitide.

Figure 3B:
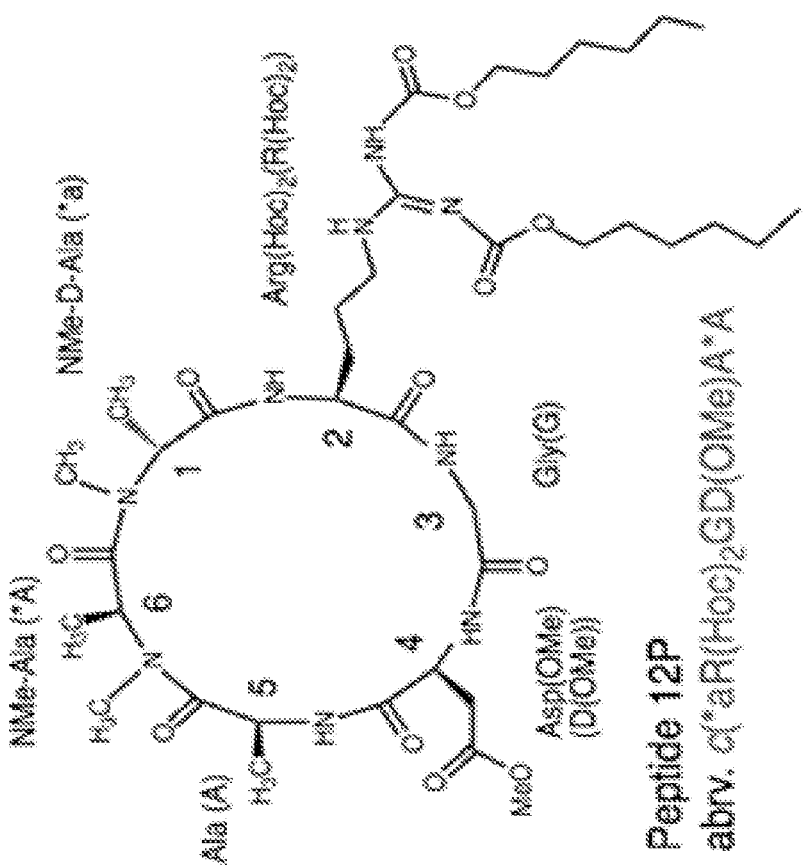
FIG. 3A-3B show the structures of peptide 12 (c(*aRGDA*A)) (FIG. 3A) and its prodrug peptide 12P (c(*aR(Hoc)₂GD(OMe)A*A)) (FIG. 3B).
Figure 3A:
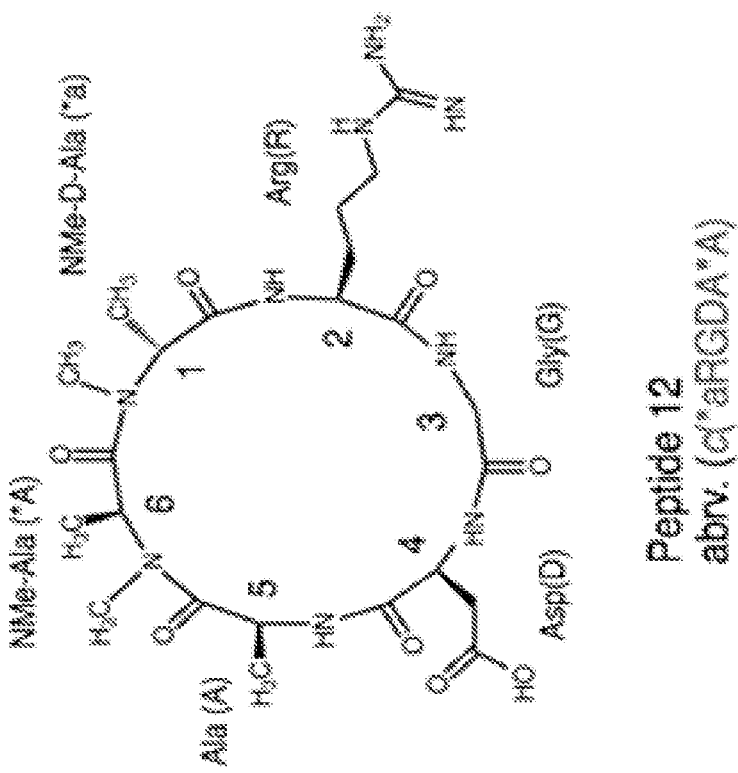

Step 5. Protection of the charged functional groups by the prodrug concept to regain intestinal and oral permeability of the active peptide Peptides #5, 12, 17, 23, 29 and 30 (SEQ ID Nos: 1, 2, 3, 4, 5, and 6, respectively) were tested for intestinal permeability in the Caco-2 model. It turned out that all peptides had significant lower permeability than their parent all Alanine-peptides (peptides #1-#4, FIG. 1). This loss of permeability may be attributed to the interdiction of the charged guanidinium and carboxylate groups of the RGD Example 2: Intestinal Permeability, Metabolic Stability and Oral Bioavailability Studies For the proof of concept of the prodrug method peptide 12 (SEQ ID NO: 2) and its prodrug peptide 12P (SEQ ID NO: 10) were used (FIG. 3).

In-vitro permeability studies utilized with the Caco-2 model are an essential component of designing the DLP of peptides, as they allow good prediction for in-vivo oral absorption of compounds [23]. The Caco-2 model is a widely used tool in the academia and pharmaceutical industry to evaluate and predict compounds' permeability mechanism. The Caco-2 system consists of human colon cancer cells that multiply and grow to create a monolayer that emulate the human small intestinal mucosa [24].

Transport studies were performed through the Caco-2 monolayer mounted in an Ussing-type chamber set-up with continuous trans-epithelial electrical resistance (TEER) measurements to assure TEER between 800 and 1200 Sr $cm^2$. HBSS supplemented with 10 mM MES and adjusted to pH 6.5 were used as transport medium in the donor compartment and pH 7.4 in the acceptor compartment. The donor solution contained the test compound. The effective permeability coefficients (Papp) were calculated from concentration-time profiles of each of the tested compounds in the acceptor chamber [25]. In every assay, the compounds were compared to the standards atenolol and metoprolol which represent para-cellular and trans-cellular permeability mechanisms respectably [26].

Permeability mechanism of compounds is studied by evaluating the Papp of a compound from the apical to the basolateral (A-to-B) membrane and its Papp from the basolateral to the apical membrane (B-to-A). The A-to-B assay simulates passive and transporter-mediated permeability. The B-to-A assay is essential complementary experiment indicative of the activity of P-gp. The ratio of the A-to-B and B-to A Papps (efflux ratio) is calculated to determine the permeability mechanism. A significant difference between the permeability coefficients in the two directions (efflux ratio of 1.5-2 or above), is a strong indication of active transport or efflux system involvement [27].

Figure 4:
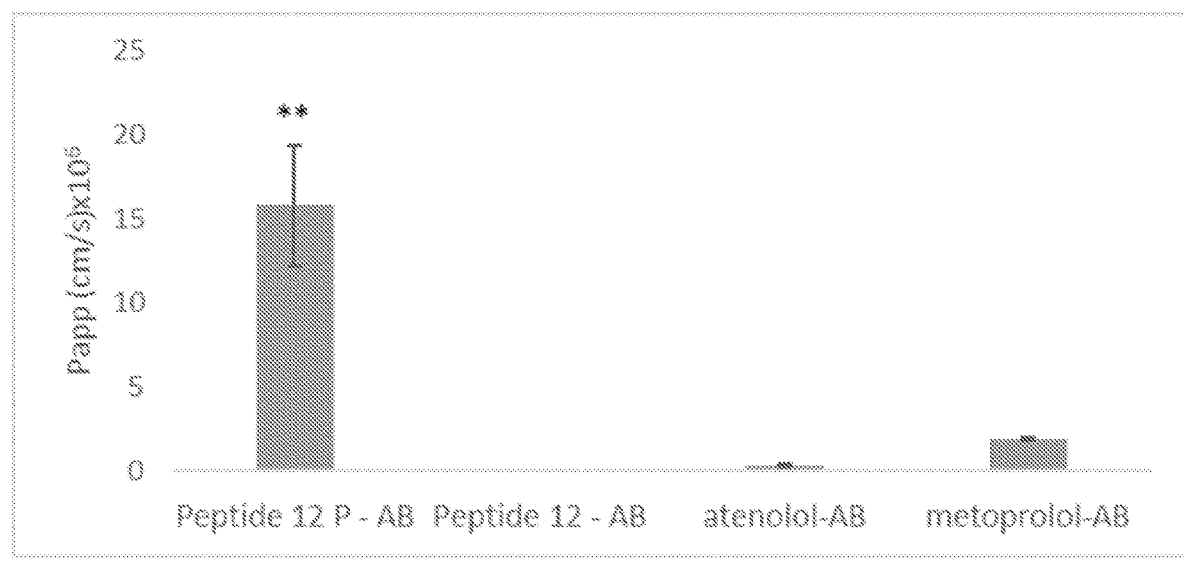
FIG. 4 shows the Caco-2 apparent permeability coefficient (Papp) of peptide 12 and peptide 12P. (average±SEM, n=3). Unpaired t-test, **p<0.005.

Peptide 12 (c(*aRGDA*A, SEQ ID NO: 2), was selected from the RGD library (Peptides #5-28 (FIG. 1)) because of its high affinity and selectivity to the integrin receptors. FIG. 4 presents the results of Caco-2 A-to-B assay of peptide 12 and its prodrug peptide 12P (c(*aR(Hoc)$_2$GD(OMe)A*A), SEQ ID NO: 10). The results show that charge masked prodrug have significantly increased permeability rate with Papp of 15.79 of the prodrug vs. 0.0617 of the drug.

Figure 5:
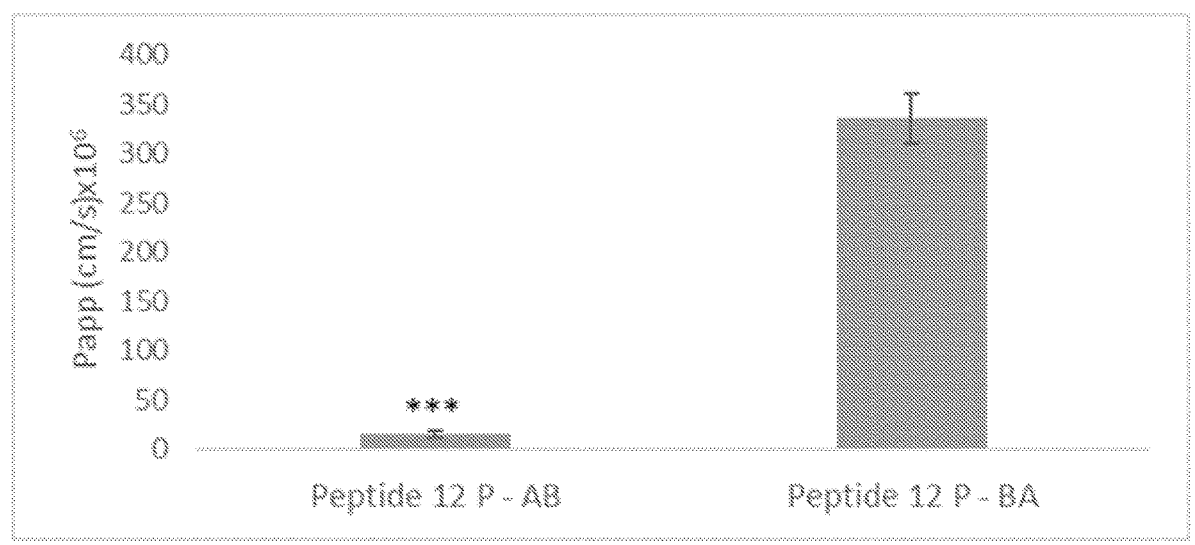
FIG. 5 shows the Caco-2 A-to-B and the B-to-A permeability of peptide 12P (average±SEM, n=3). Unpaired t-test, ***p<0.0005.
Figure 6:
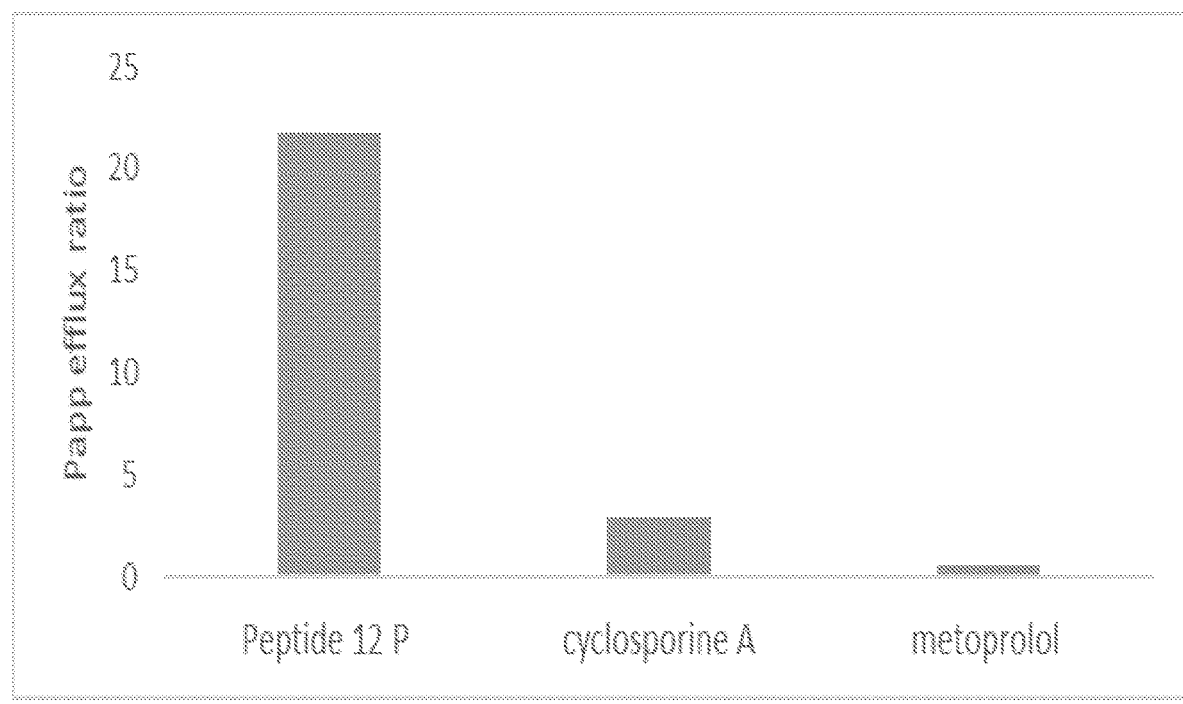
FIG. 6 shows the Caco-2 Papp efflux ratios (Papp BA/Papp AB) of Peptide 12P, cyclosporine A and metoprolol.

Furthermore, the B-to-A study, revealed higher Papp of peptide 12P than its A-to-B Papp (335.8 vs. 15.7, FIG. 5). The efflux ratio of peptide 12P is about 20. The efflux ratio of cyclosporine, a known P-gp substrate is 3. (FIG. 6). This ratio indicates significant involvement of efflux system in the permeability mechanism of 12P. Practically, any ratio higher than 2 is a valid indication of the involvement of the efflux activity.

It is important to note that the involvement of efflux system is actual indication that the prodrug is permeate through the enterocytes membrane and afterwards removed from these cells by the efflux system.

Figure 7:
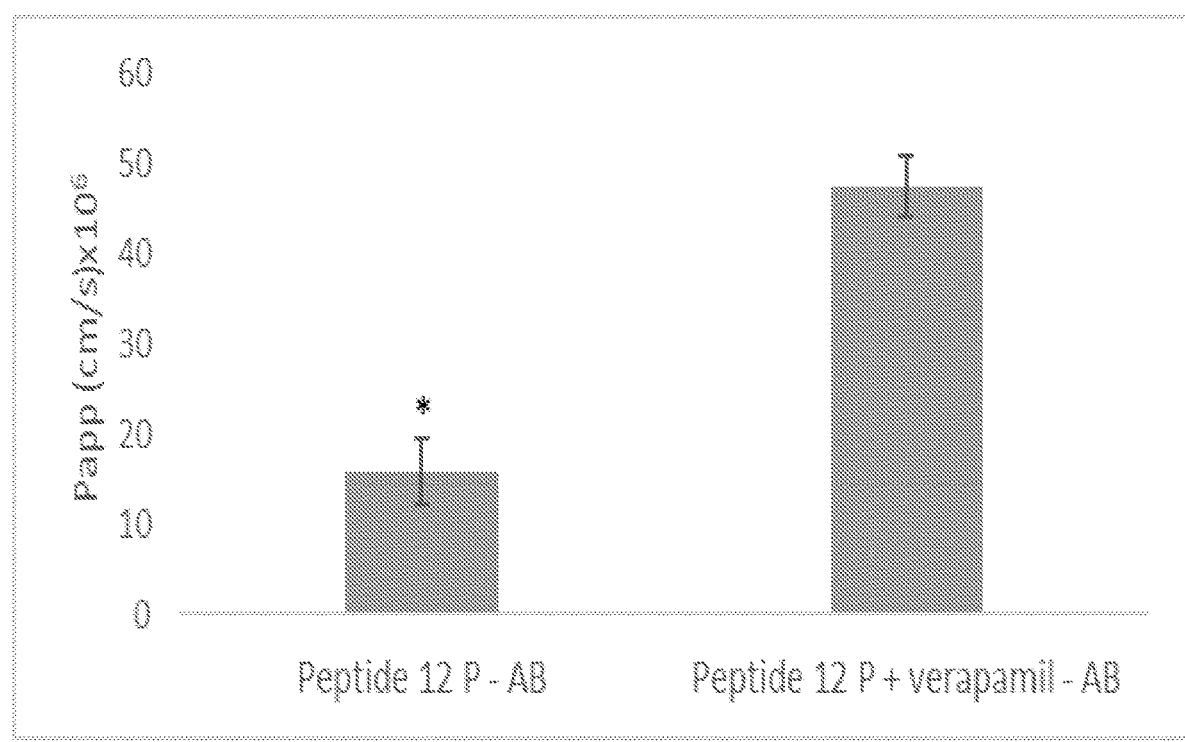
FIG. 7 shows the Caco-2 Papp of Peptide 12P A-to-B in the presence of verapamil (100 μM) (average±SEM, n=3). Unpaired t-test, *p<0.05.
Figure 8:
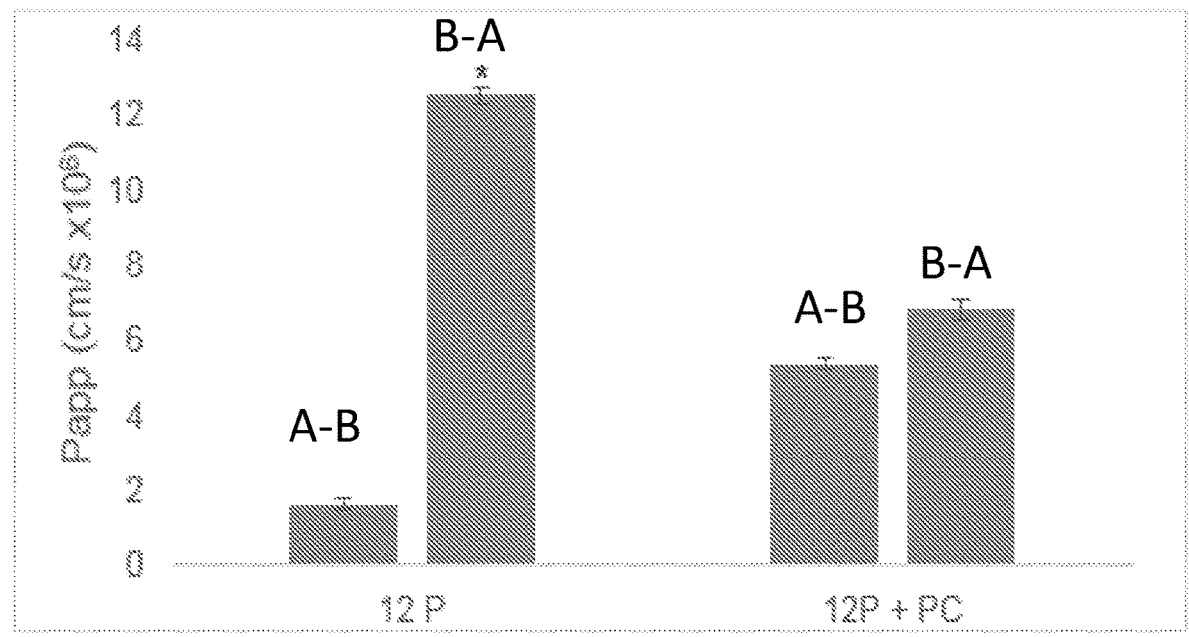
FIG. 8 shows the Caco-2 Papp, A-B and B-A as indicated, of peptide 12 P alone or with PC (n=3 for each group). (*) A significant difference was found between $P_{app}$ AB and BA of peptide 12 P alone (P<0.05).

To further study the efflux system involved in the permeability mechanism of peptide 12P, a Caco-2 study in the presence of verapamil (100 mM), a known P-gp inhibitor was performed. The results (FIG. 7) show a 3-fold increase in Papp of peptide 12P, in the presence of verapamil, from 15.7 to 47.4. Prodrug peptide 12P was additionally tested in the presence of palmitoyl carnitine chloride (PC), which enhances the permeability of hydrophilic compounds by effecting the TJs of the epithelial barrier. FIG. 8 shows that the presence of PC affects the Papp values compared to verapamil, which is related to the inhibition of the efflux system. There is a significant difference between the Papp of peptide 12P alone (1.64±0.15 vs 12.52±0.20 cm/s×10$^6$), whereas in the presence of PC, the AB and BA Papp values are similar (5.37±0.16 vs 6.80±0.28 cm/s×10$^6$). These results further strengthen the hypothesis that peptide 12P permeates through the intestine monolayer with the involvement of the efflux systems.

Example 3: Metabolic Stability Studies

Generally, the purpose of metabolic stability studies is to evaluate the compounds rate of elimination in the presence of hostile environments: a rat plasma or extractions of the gut wall. In these environments, compounds are prone to enzymatic degradation, as there are high concentrations of peptidases, esterases, lipases and other peptides that metabolize xenobiotics to building units for synthesizing essential structures in the body [28, 29].

Specifically, in our case, the purposes of the metabolic stability studies are (1) to prove that the prodrug (peptide 12P, SEQ ID NO: 10) is digested by esterases to furnish the drug (peptide 12, SEQ ID NO: 2) and (2) to demonstrate that peptides 12 and 12P are stable to digestion in the intestine.

Figure 9A:
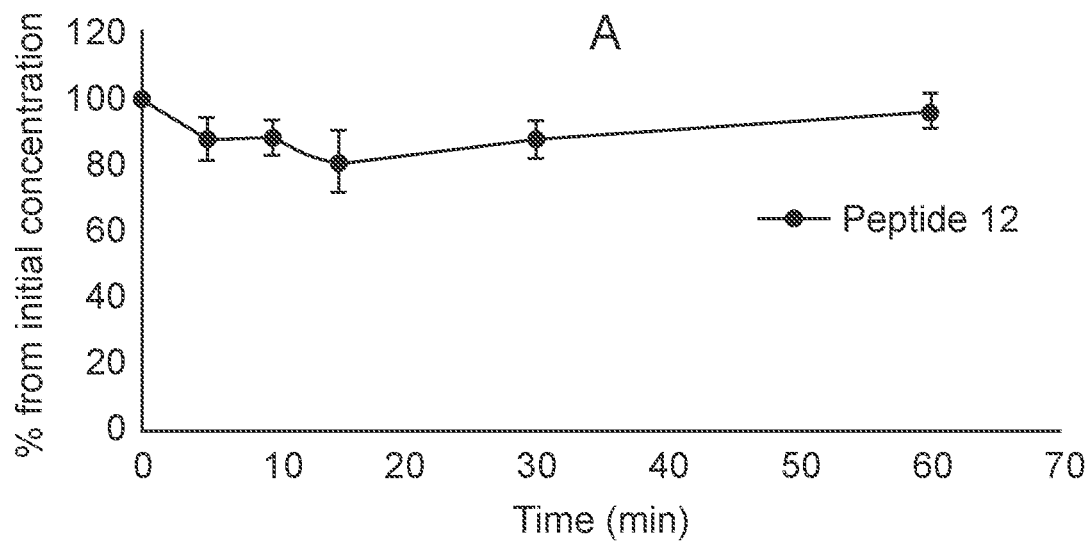
FIG. 9A-9B show the metabolic stability of Peptide 12 (FIG. 9A) and Peptide 12 P (FIG. 9B) in rat plasma (average±SEM).
Figure 9B:
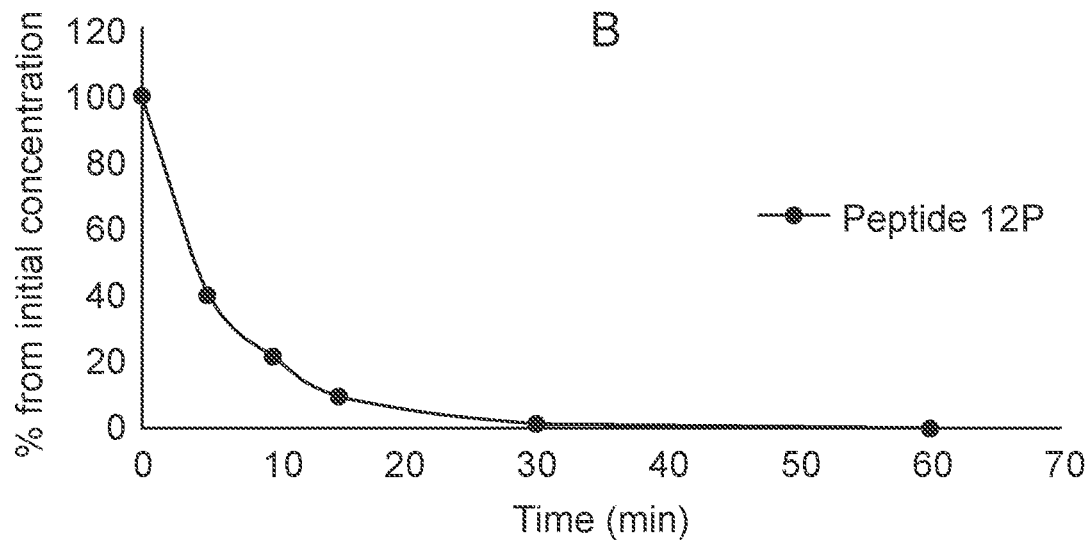

The enzymatic reactions were performed as follows: 2 mM stock solutions of the tested compounds were diluted with serum or purified brush border membrane vesicles (BBMVs) solution to a final concentration of 0.5 mM. During incubation at 37° C. samples were taken for a period of 90 minutes. The enzymatic reaction was stopped by adding 1:1 v/v of ice cold acetonitrile and centrifuge (4000 g, 10 min) before analysis. Preparation of BBMVs: The BBMVs was prepared from combined duodenum, jejunum, and upper ileum (male Wistar rats) by a Ca$^{++}$ precipitation method. Purification of the BBMVs was assayed using GGT, LAP and alkaline phosphatase as membrane enzyme markers Peptides 12 and 12p were subjected to rat plasma and followed their degradation. Rat plasma is known to be rich with esterases. FIG. 9 demonstrates the degradation of peptides 12 and 12P in rat plasma due to esterases activity. Peptide 12 remained stable during the incubation time (FIG. 9A), because it lacks ester bonds. Peptide 12P on the other hand is degraded (FIG. 9B) to yield peptide 12 because it contains ester bonds. This experiment proves that peptide 12P is a prodrug of peptide 12.

Next, peptides 12 and 12P were subjected to extractions of the gut wall (brush border membrane vesicles, BBMV) and rate of degradation was examined. The BBMV assay determines the peptides stability in the presence of digestive enzymes in the brush border membrane of the intestine especially peptidases.

Figure 10:
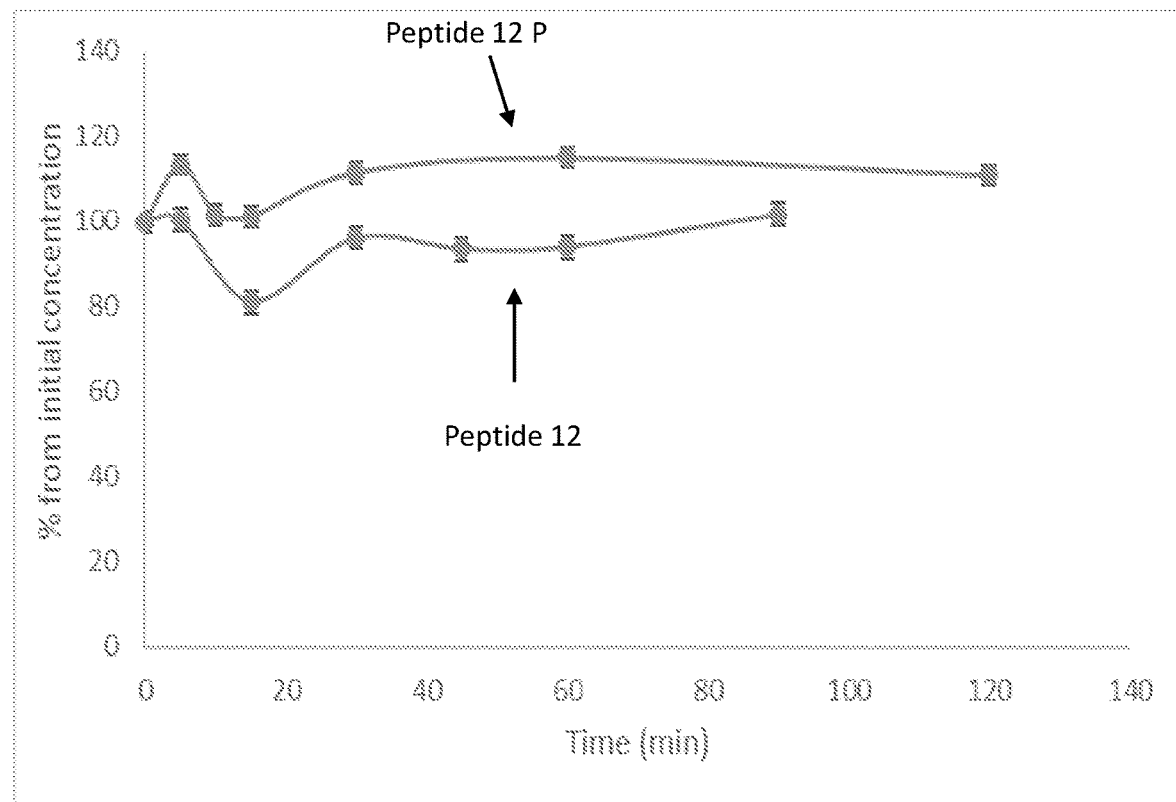
FIG. 10 shows the metabolic stability of peptide 12 and peptide 12P in rat BBMVs (average±SEM).

As can be seen in FIG. 10, both peptides are stable to enzymes in the BBMV which indicates oral bioavailability and therefore fulfill the DLP paradigm.

Figure 11:
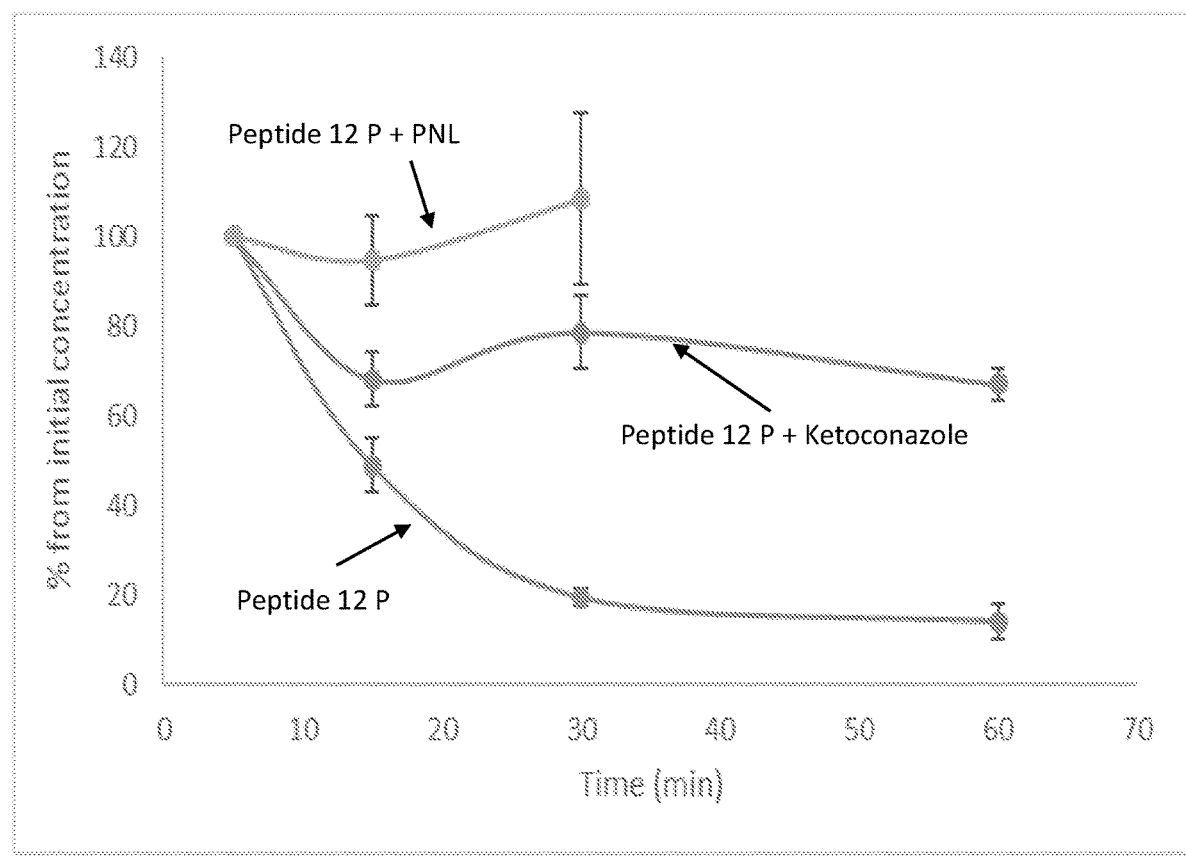
FIG. 11 shows the metabolic stability of peptide 12P in the presence of human liver microsomes (average±SEM) and with Cyp inhibitor (0.1 μM ketoconazole) and PNL formulation.
Figure 12:
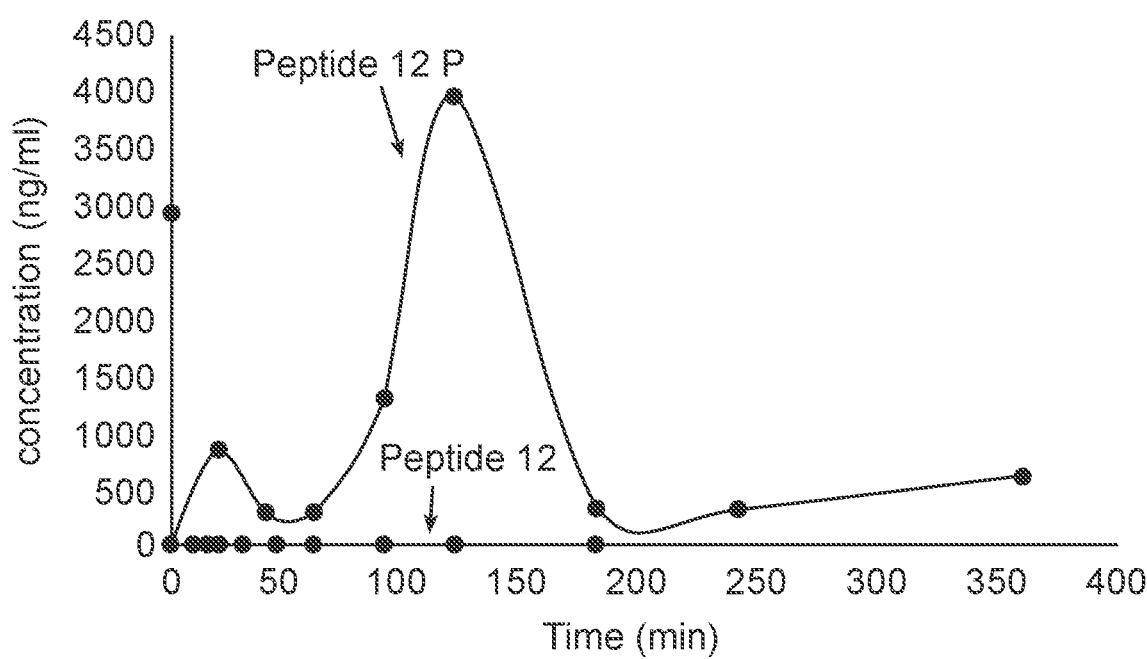
FIG. 12 shows plasma concentrations plotted against time scale after 5 mg/kg oral administration of Peptide 12P (n=3) and Peptide 12 (n=4).

Peptide 12 P was subjected to additional in vitro assay to evaluate the involvement of liver metabolism using the Pooled Human Liver Microsome assay. Liver microsomes are subcellular particles derived from the endoplasmic reticulum of hepatic cells. These microsomes are a rich source of drug metabolizing enzymes, including cytochrome P-450. Microsome pools from various sources are useful in the study of xenobiotic metabolism and drug interactions. FIG. 11 presents the degradation of peptide 12 P by Pooled Human Liver Microsomes. The presence of ketokonazole inhibits the metabolism by the liver enzymes in some degree. However, Incubating peptide 12P with self-assembling pro-nano liposphere (PNL) [30], led to much better inhibition of cytochromes P-450. This result is another proof that peptide 12P is a substrate for P-gp efflux system and cytochromes P-450, and while overcoming the permeability challenges, peptide 12P formulation protected against efflux systems and enzymatic metabolism in the intestine and liver.

Figure 13:
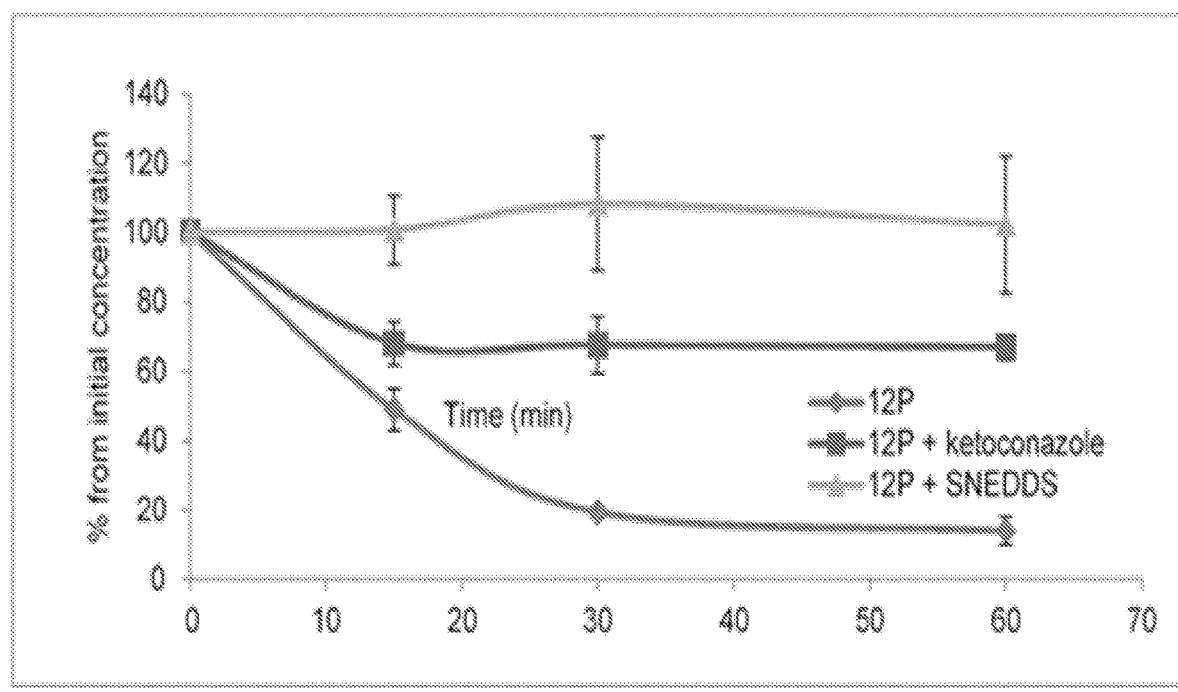
FIG. 13 shows 12P concentrations following 30 min incubation of dispersed 12P SNEDDS vs. 12P with ketoconazole and 12P alone in isolated rat CYP3A4 microsomes. (n=3 for each group). Significant difference (p<0.01) was found between 12P and dispersed 12P with SNEDDS and between 12P and 12P with ketoconazole (P<0.05).
Figure 14:
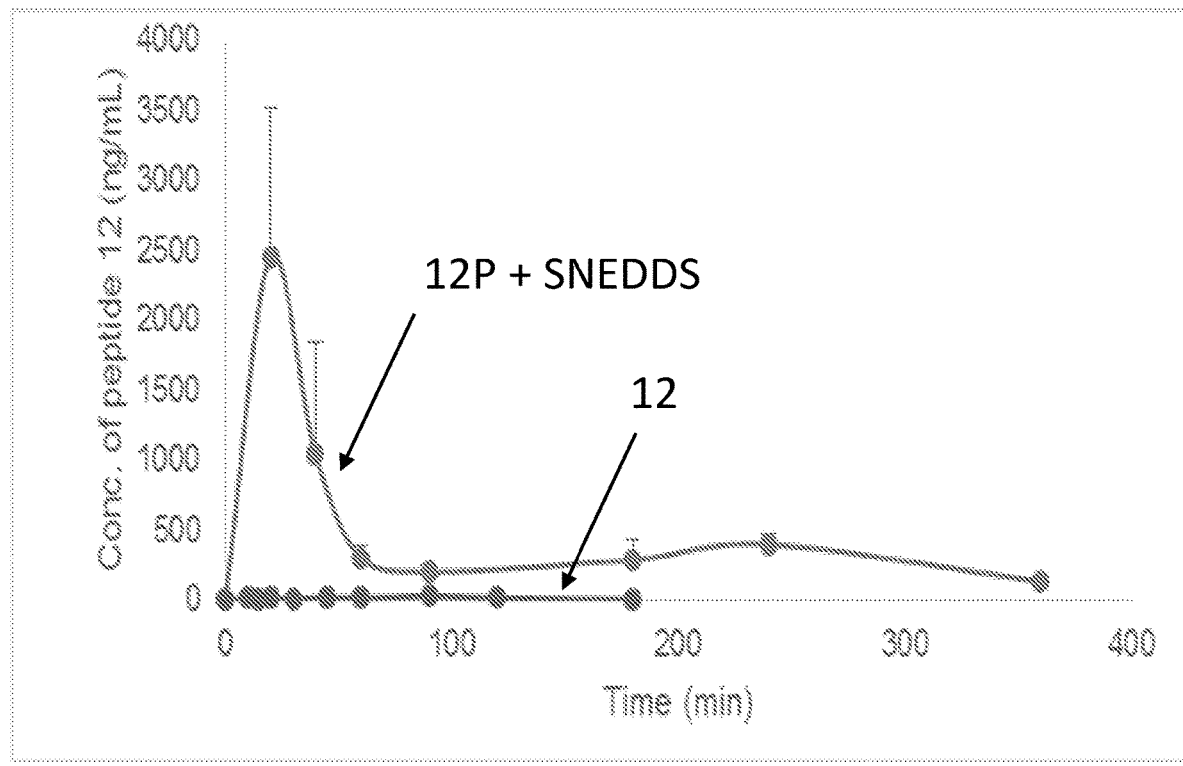
FIG. 14 shows profiles of plasma concentration of peptide 12 vs. time in rats after oral administration of 5 mg/kg peptide 12P+SNEDDS and peptide 12. (n=3 for each group).
Figure 15:
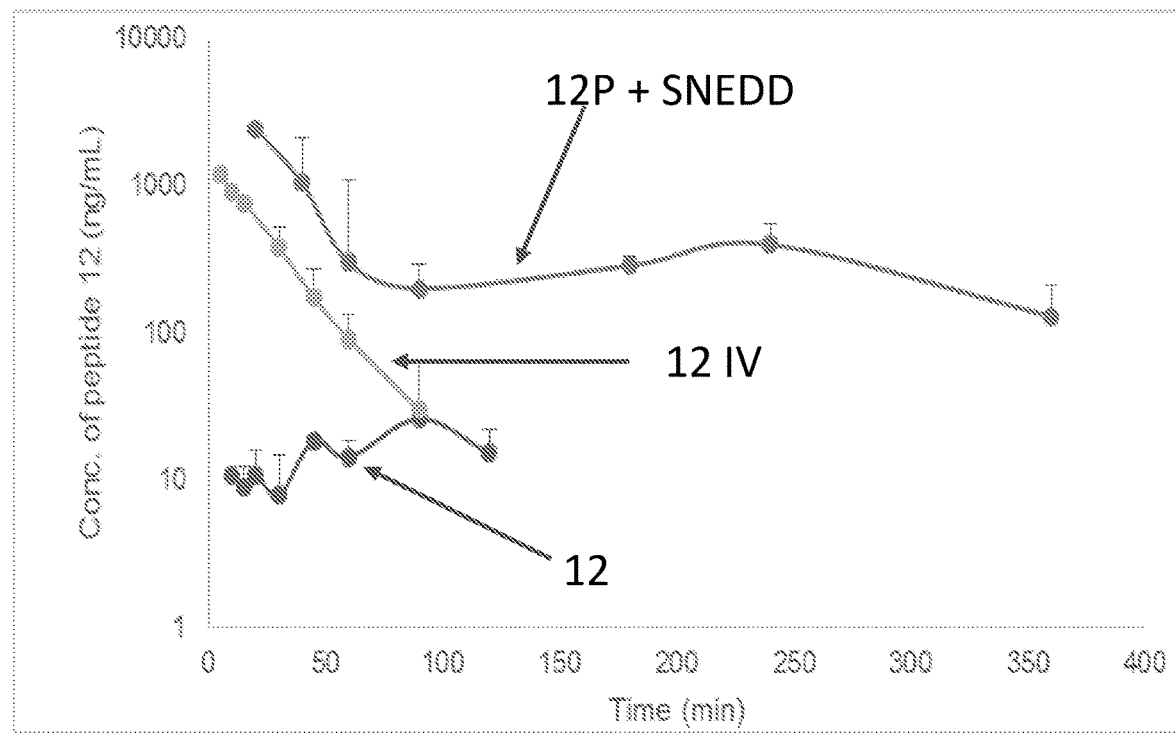
FIG. 15 shows semi-logarithmic plot of plasma concentration of peptide 12 vs. time profiles in rats following oral administration of 5 mg/kg of peptides 12P and 12 and following 0.5 mg/kg bolus administration of peptide 12 (marked as 12 IV), (n=3 for each group).

The mechanism of absorption was further tested in isolated rat CYP3A4 microsomes. The question of how the efflux is affected by ketoconazole, a specific CYP3A4 inhibitor, and by SNEDDS was also investigated. They were found to reduce CYP3A4 metabolism and reduce P-gp efflux (FIG. 13). The concentrations that remained following 60 min of incubation of dispersed peptide 12P were compared. The groups included peptide 12P with SNEDDS, 12P with ketoconazole, and 12P alone (102.2±19.7%, 67.0±3.61%, and 14.0±4.06% respectively). A significant difference (p<0.01) was found between peptide 12P and the dispersed peptide 12P with SNEDDS and between peptides 12P and 12P with ketoconazole (p<0.05). The plasma concentration-time profiles for peptide 12 and the dispersed peptide 12P SNEDDS following oral administration of 5 mg/kg of peptides 12 or 12P to rats are shown in FIGS. 14 and 15. The corresponding AUC and $C_{max}$ parameters obtained in these in vivo experiments are listed in Table 2 and were significantly greater for the dispersed peptide 12P SNEDDS in comparison to peptide 12. The relative bioavailability of peptide 12P was about 70-fold greater than that of peptide 12 after oral administration (FIG. 15).

TABLE 2

AUC, $C_{max}$, $k_{el}$ values, and $T_{max}$ values (Median (range)) of Peptide 12 obtained following oral administration of peptide 12 and dispersed 12P SNEDDS.

| Peptide | 12 | 12P |
|---|---|---|
| $C_{max}$ (ng/mL) | 119 ± 86 | 1993 ± 967 |
| $T_{max}$ (min) | 45 (20-90) | 20 (20-60) |
| AUC (min*µg/mL) | 1.91 ± 0.37 | 216.9 ± 75.6 |
| $K_{el}$ (min$^{-1}$) | 0.04 ± 0.005 | 0.009 ± 0.0001 |
| F (%) | 0.58 ± 0.11 | 43.8 ± 14.9 |

Example 4: Pharmacokinetic Study

The pharmacokinetic in-vivo study allows a further evaluation of the prodrug concept in the whole animal. The PK studies were performed in conscious Wistar male rats. An indwelling cannula was implanted in the jugular vein 24 hours before the PK experiment to allow full recovery of the animals from the surgical procedure. Animals (n=4) received either an IV bolus dose or oral dose of the investigated compound. Blood samples (with heparin, 15 U/ml) were collected at several time points for up to 6 hours post administration and was assayed by HPLC-MS method. Non-compartmental pharmacokinetic analysis was performed using WinNonlin software.

This study showed significant increase in the area under the curve (AUC) of peptide 12 after peptide 12P administration. In other words, the PK study shows that after oral administration of peptide 12P (the prodrug), peptide 12 (the drug) appears in the systemic blood circulation. This proves that (a) peptide 12P is orally available; (b) it is stable in the intestine; and (c) it is metabolized in the blood to regenerate peptide 12. To ensure good bioavailability of the drug, the prodrug was formulated in a nanoparticles formulation that is known to inhibit the P-gp efflux system. It should be mentioned that peptide 12 was also formulated in the same nanoparticle. In this case the formulation did not enhance oral bioavailability since this peptide is actually intestinally non-permeable (FIG. 4). These results are an in-vivo proof of concept for the prodrug approach.

Other peptides and their prodrug analogs were subjected to the Caco-2 assay and showed the same behavior as peptide 12.

Figure 16B:
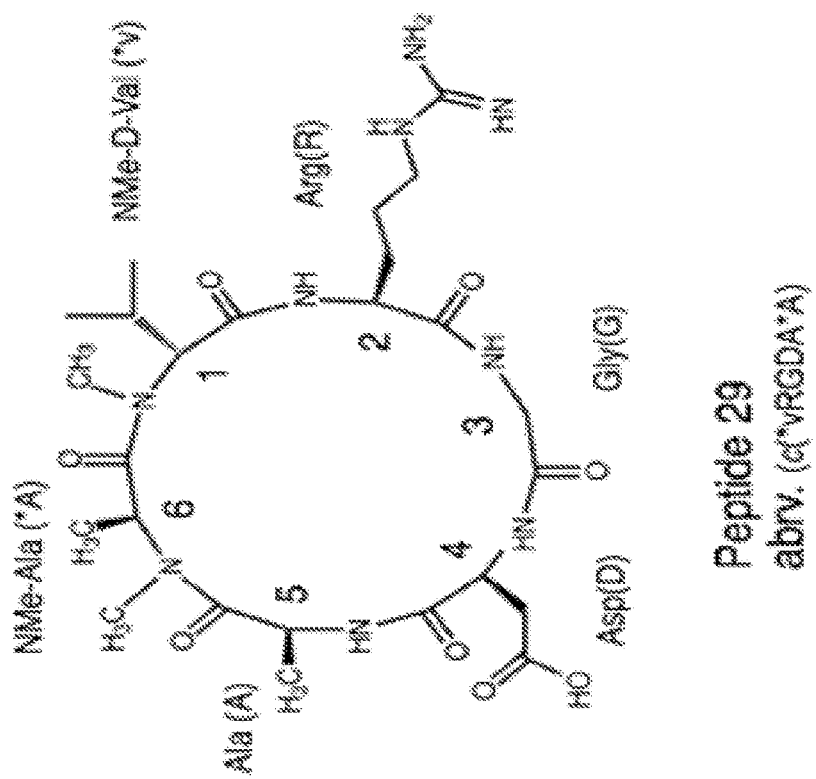
FIG. 16A-16B show the structures of peptide 29 (c(*vRGDA*A)) (FIG. 16A) and peptide 29P (c(*vR(Hoc)₂GD(OMe)A*A)) (FIG. 16B).
Figure 16A:
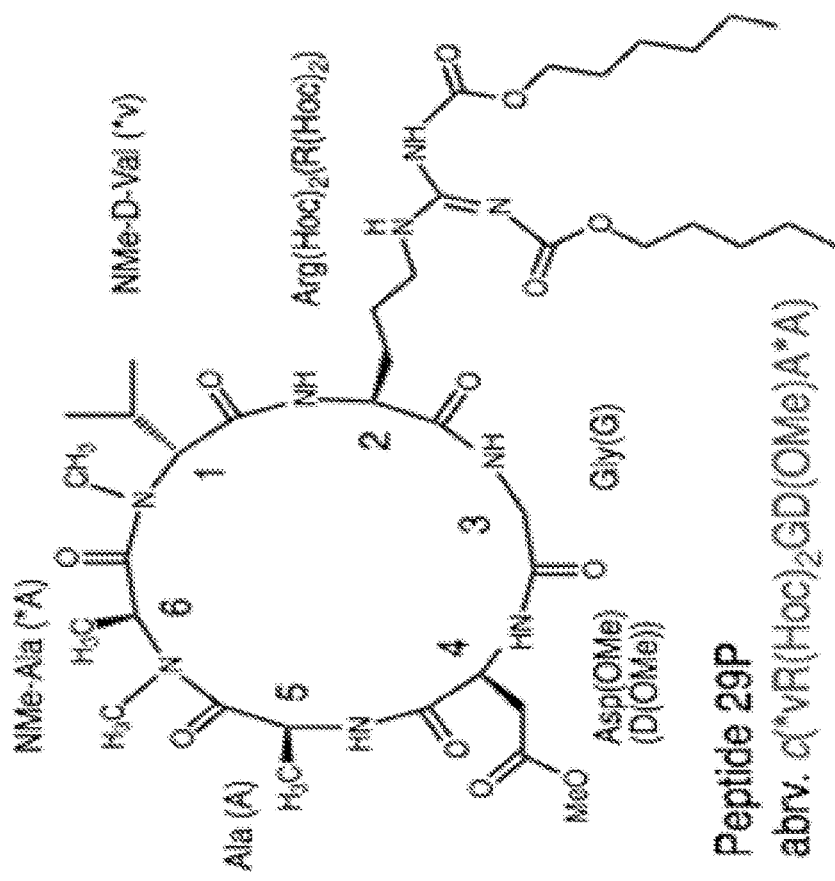

Peptide 29 (c(*vRGDA*A), SEQ ID NO: 5) and its prodrug 29P (c(*vR(Hoc)$_2$GD(OMe)A*A), SEQ ID NO: 9) were selected from the RGD library (Peptides #5-28, FIG. 1) for further proof of concept because of its high affinity and selectivity to the integrin receptors. The structures of both peptides are shown in FIG. 16.

Figure 17:
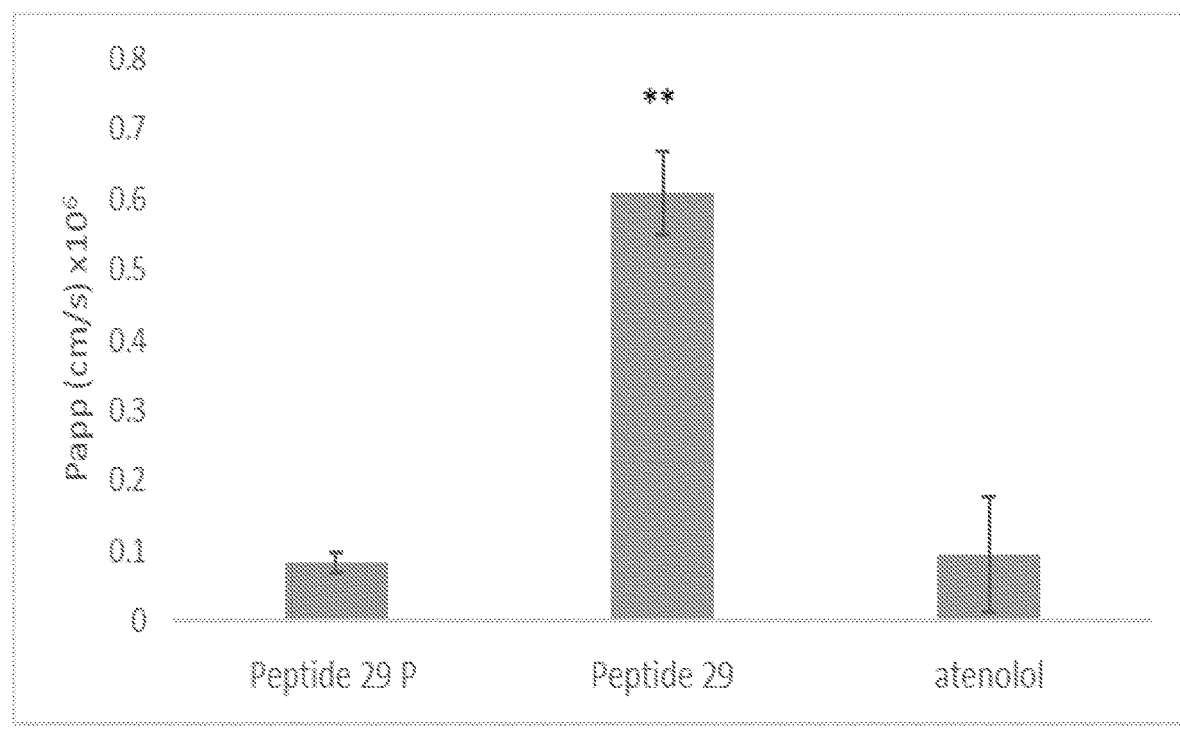
FIG. 17 shows the Caco-2 A-to-B Papp of Peptide 29P, Peptide 29 and atenolol. (average±SEM, n=3). Unpaired t-test, **p<0.005.

The permeability of both peptides (peptide 29 and 29P) is low. The Papp of Peptide 29P is lower in the A-to-B assay, than the Papp of Peptide 29 (0.08 vs. 0.6 respectively), as shown in FIG. 17.

Figure 18:
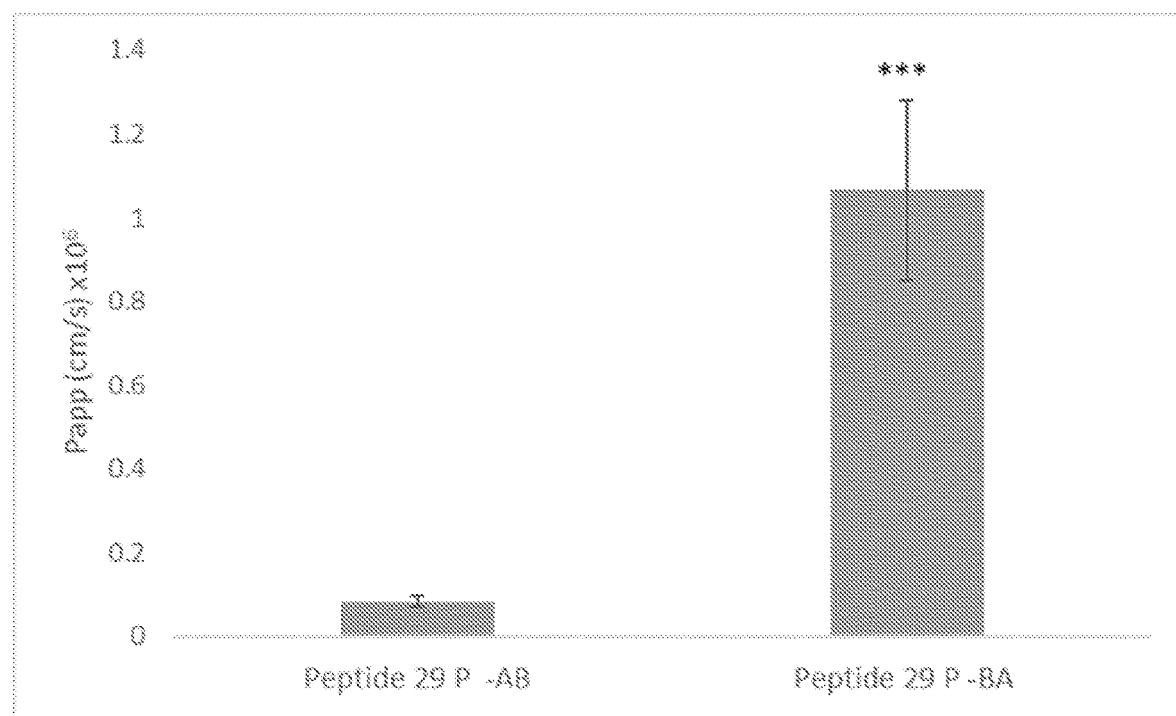
FIG. 18 shows the Caco-2 Papp of Peptide 29P: A-to-B vs. B-to-A Papp (average±SEM, n=3). Unpaired t-test, ***p<0.0005.

This unanticipated result is clarified when comparing the B-to-A Papp of Peptide 29P to its A-to-B Papp (FIG. 18). The B-to-A Papp of the prodrug is significantly higher than the A-to-B Papp (0.08 vs. 1.06), suggesting that the low A-to-B Papp was resulted from extensive activity of the efflux system.

Figure 19:
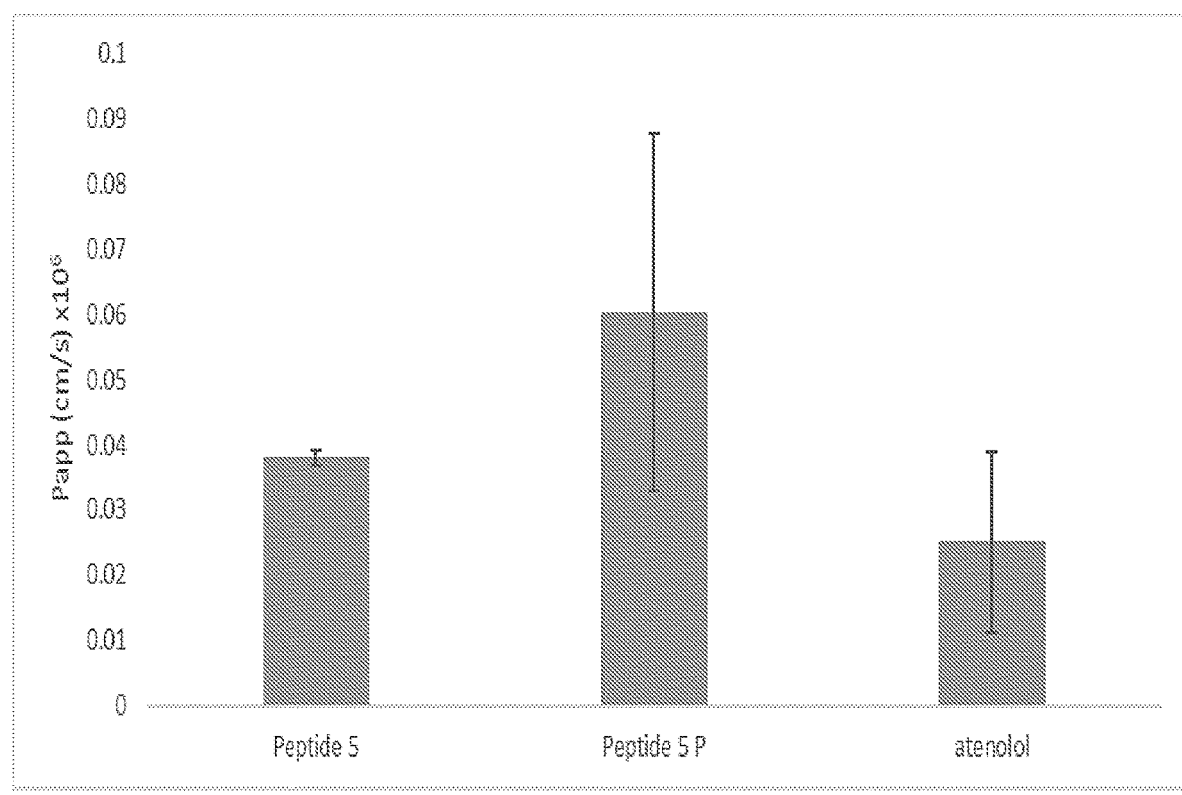
FIG. 19 shows the Caco-2 Papp of peptide 5 and peptide 5P compared to atenolol (average±SEM, n=3).

Peptide 5 (c(*rGDA*AA, SEQ ID NO: 1) and its prodrug, peptide 5P (c(*r(Hoc)$_2$GD(OMe)A*AA), SEQ ID NO: 11) were also evaluated. In these peptides, the N-methylation pattern is 1,5 rather than 1,6 (the pattern in peptide 29 and its prodrugs). Also, in these peptides (5 and 5P) the D-amino acid is Arginine. In the Caco-2 model, both the drug (peptide 5) and the prodrug (peptide 5P) exhibit relatively low Papps (0.03 and 0.06) which is very similar to the atenolol Papp (0.025, FIG. 19).

Figure 20:
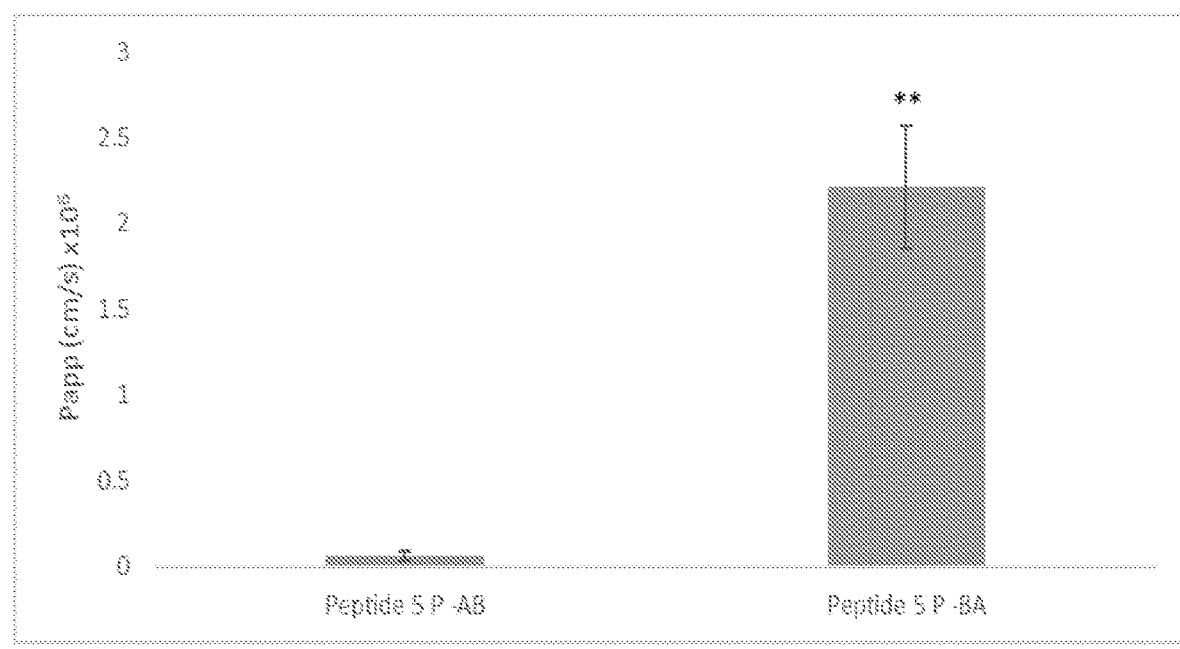
FIG. 20 shows the permeability of peptide 5P A-to-B vs. B-to-A (average±SEM, n=3). Unpaired t-test, **p<0.005.

The B-to-A permeability of peptide 5P resulted in much higher Papp than its A-to-B Papp (2.12 vs 0.06, FIG. 20), suggesting again the involvement of efflux system, which attributes to peptide 5P's low A-to-B permeability of the prodrug.

Peptides 17, 23, and 30 (SEQ ID Nos: 3, 4, and 6, respectively) and their corresponding prodrugs 17P (c(r(Hoc)$_2$G*D(OMe)A*AA), SEQ ID NO: 13), 23P (c(r(Hoc)$_2$GD(OMe)A*A*A), SEQ ID NO: 12), and 30P (c(*fR(Hoc)$_2$GD(OMe)A*A), SEQ ID NO: 14 showed the same pattern of intestinal permeability as peptides 12 and 12P, 29 and 29P and 5 and 5P. Table 3 Summarizes Papp efflux A-B and B-A of the examined RGD peptides.

TABLE 3

$P_{app}$ values (n = 3 for each group) of RGD peptides and their prodrug derivatives for AB and BA permeability and the efflux ratio in Caco-2 cell model.

| scaffold | peptide | Sequence | $P_{app}$ AB [cm/s ×10$^6$] | $P_{app}$ BA [cm/s ×10$^6$] | efflux ratio |
|---|---|---|---|---|---|
| NMe(1,5) | 5 | c(*rGDA*AA) | 0.38 ± 0.01 | 0.42 ± 0.11 | 1.1 |
| NMe(1,5) | 5P | c(*r(Hoc)$_2$GD(OMe)A*AA) | 0.6 ± 0.27 | 22.12 ± 3.58 | 36.73 |
| NMe(1,6) | 12 | c(*aRGDA*A) | 0.04 ± 0.02 | 0.12 ± 0.01 | 2.80 |
| NMe(1,6) | 12P | c(*aR(Hoc)$_2$GD(OMe)A*A) | 0.79 ± 0.18 | 16.8 ± 1.3 | 12.76 |
| NMe(5,6) | 23 | c(rGDA*A*A) | 0.61 ± 0.09 | 1.34 ± 0.03 | 2.19 |
| NMe(5,6) | 23P | c(r(Hoc)$_2$GD(OMe)A*A*A) | 1.77 ± 0.55 | 74.77 ± 20.36 | 42.24 |
| NMe(1,6) | 29 | c(*vRGDA*A) | 0.07 ± 0.01 | 0.15 ± 0.01 | 2.14 |
| NMe(1,6) | 29P | c(*vR(Hoc)$_2$GD(OMe)A*A) | 0.82 ± 0.13 | 10.66 ± 2.14 | 13 |
| | atenolol [a] | | 0.31 ± 0.08 | | |
| | metoprolol [b] | | 1.89 ± 0.11 | | |

[a] atenolol is a marker for paracellular permeability,
[b] metoprolol is a marker for transcellular permeability.

Previous work has shown that Cilengitide has the potential to have anti-angiogenic effects. Unfortunately however, clinical trials using this drug in the treatment of glioblastoma were disappointing and production of this drug has been discontinued. We have published that actually low doses of Cilengitide can have vascular promotion effects, i.e. increasing tumour angiogenesis above and beyond that of the untreated tumor [31]. Indeed, we have evidence that in combination with the appropriate chemotherapeutics vascular promotion induced by treatment with low dose Cilengitide is sufficient to halt tumor growth in pre-clinical mouse models of cancer [25]. This provides an exciting opportunity to exploit vascular promotion in combination with chemotherapy or indeed other therapies where increasing delivery to the tumor might be of benefit. The prodrug approach presented here is a potential to exceed the Cilengtide efficacy.

Example 5: Molecular Docking Methods

The crystal structures of αvβ3 (PDB code: 1L5G) [32] in complex with Cilengetide was prepared for docking calculations using the Protein Preparation Wizard tool of the Schrödinger 2016 molecular modeling package [33]. First, the Mn2+ ion at the MIDAS was replaced with Mg2+. Next, all the bond orders were assigned, the disulfide bonds were created and all the hydrogen atoms were added; the prediction of the side chains hetero groups ionization and tautomeric states was performed using Epik 3.7 [34,35]. Finally, an optimization of the hydrogen-bonding network and of the hydrogen atoms positions was performed using the ProtAssing and impref utilities, respectively. All water molecules were deleted prior to docking calculations. Docking studies were carried out with the grid-based program Glide v. 7.2 [36,37]. For the grid generation, a virtual box of 20 Å×20 Å×20 Å surrounding the ligand RGD binding cavity was created. The standard precision mode for peptide ligands (SP-peptide) and the OPLS3 force field [38] were chosen to run calculations and to score the predicted binding poses. The lowest energy solution (docking scores: −7.433) that could properly recapitulate the typical RGD interaction pattern was selected for the binding mode description. All of the pictures were rendered with PyMOL.

Figure 21A:
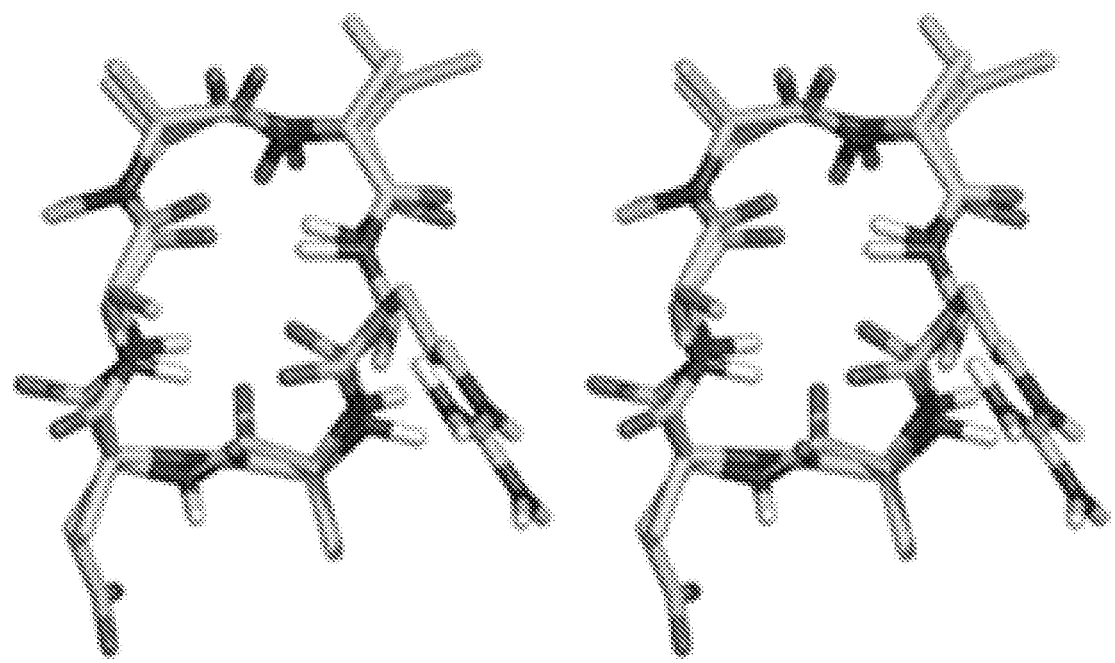
FIG. 21A-21B Show NMR analysis of peptide 29 and its prodrug.
Figure 21B:
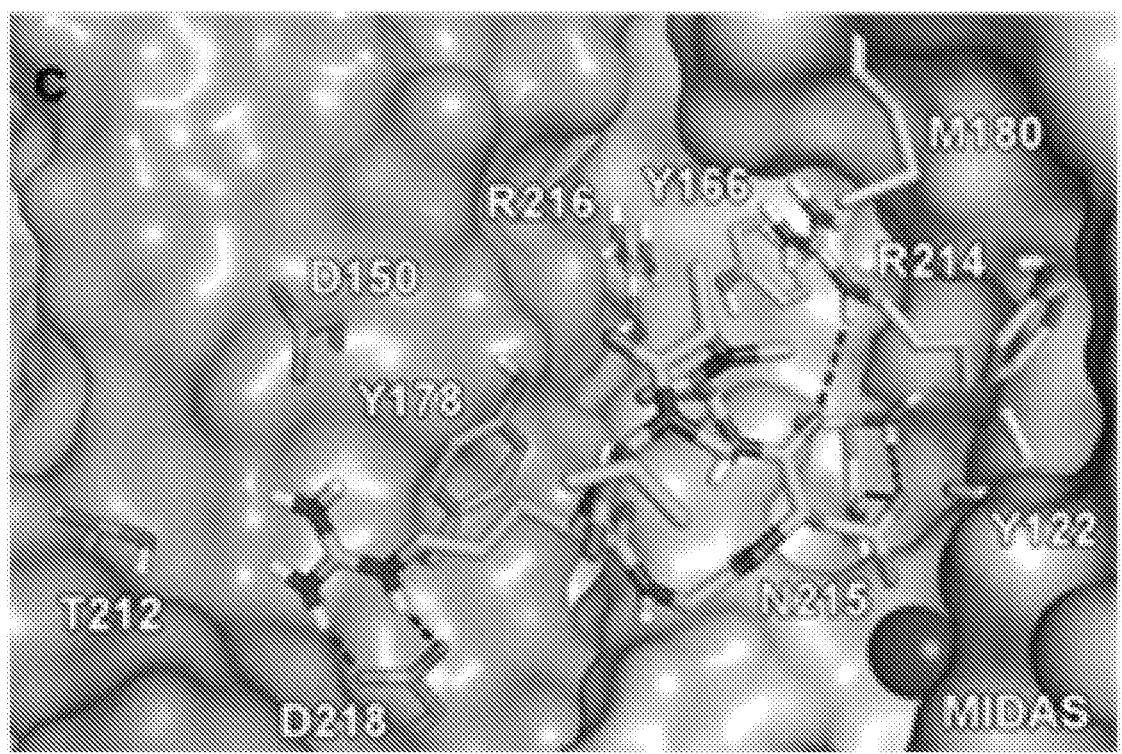

To describe at an atomic level the binding mode of the cyclic hexapeptides to integrin receptors, the solution state structure of peptide 29 was calculated by NMR studies (FIG. 21A) and was used for performing docking calculations of peptide 29 at the αvβ3 RGD binding site. According to the docking results, peptide 29 binds to αvβ3 (FIG. 21B) very similarly to the reference ligand Cilengitide. In detail, the Asp$^3$ carboxylate group coordinates the metal ion at the MIDAS and forms two H-bonds (β3)-Asn215, while the NMe-d-Arg$^1$ guanidinium group establishes a tight salt bridge with the (αv)-Asp218 side chain and a cation-π with the (αv)-Tyr178 phenolic ring. The peptide 29/αvβ3 complex is further stabilized by an additional H-bond between the Asp$^4$ backbone CO and the (β3)-Arg214 side chain and by lipophilic contacts between NMe-Ala$^6$ and (β3)-Met180. The predicted binding mode is thus overall consistent with the subnanomolar IC$_{50}$ observed for peptide 29 at the αvβ3 receptor.

Example 6: Comparing Peptide 29 and 29P Derivatives to Control Molecules

Figure 22:
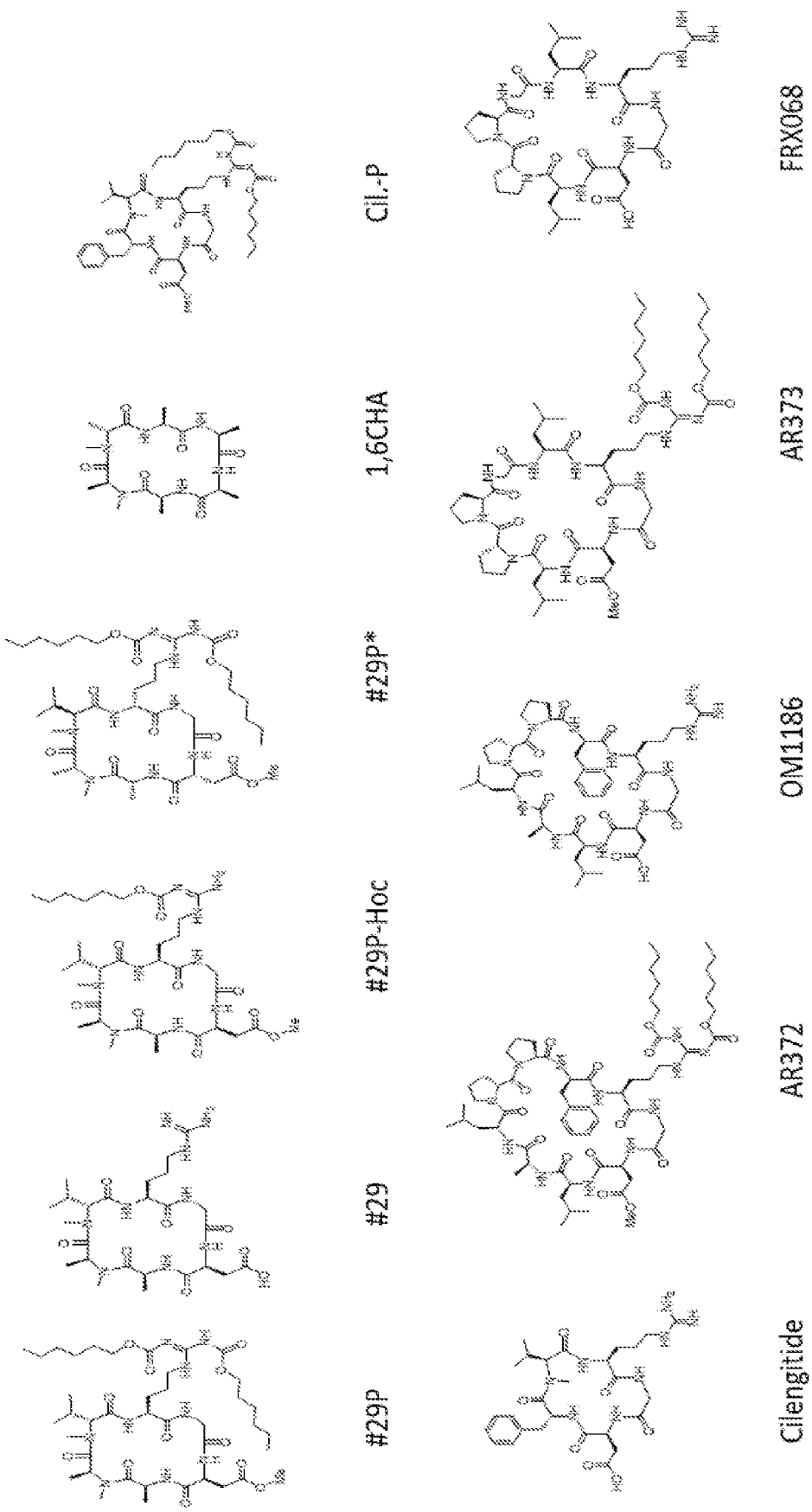
FIG. 22 shows the structure of peptide 29, peptide 29P and their derivatives as well as examined control molecules.

The RGD cyclohexapaptides library was further investigated for its physicochemical properties in vitro, using Log D, caco-2 and PAMPA models. The investigated peptide derivatives are depicted in FIG. 22.

Log D. Determination of distribution coefficients were performed as follows:

Incubations were carried out in Eppendorf-type polypropylene microtubes in triplicates. 5 μL aliquot of compound DMSO stock (10 mM) was dissolved in the previously mutually saturated mixture containing 500 μL of PBS (pH 7.4) and 500 μL of octanol followed by mixing in a rotator for 1 hour at 30 rpm. Phase separation was assured by centrifugation for 2 min at 6000 rpm. The octanol phase was diluted 100-fold with 40% acetonitrile, and aqueous phase was analyzed without dilution. The samples (both phases) were analyzed using HPLC system coupled with tandem mass spectrometer. Mebendazole was used as a reference compound (experimental log D, pH 7.4 range is 2.9-3.15). The log D values depicted in Table 3 show that the addition of lipophilic residues to the peptides, elevate the log D value, indicating higher distribution in the lipophilic phase and environment. This is evident for peptide 29 (#29, SEQ ID NO: 5), peptide 29P having a single Hoc (#29P-Hoc, FIG. 22), and peptide 29P having 2 Hoc molecules (#29P, SEQ ID NO: 9). The results show that with no lipophilic residues (#29), the log D is <−1. Adding one Hoc and OMe group (#29P-Hoc) elevate the log D value to 1.85, and the completely protected peptide (#29P) has the highest value of 4.86. Similar results are seen when comparing the log D values of other peptides and their prodrug derivatives in Table 4.

TABLE 4

Log D values for the cyclic peptides, in comparison to mebendazole

| Compound ID | LogD, pH 7.4 | |
| --- | --- | --- |
| Mebendazole | 3.02 | 3.04 |
|  | 3.05 |  |
|  | 3.03 |  |
| #29P | 5.07 | 4.86 |
|  | 4.80 |  |
|  | 4.72 |  |
| #29 | −5.01 | <−1 |
|  | −1.75 | (−2.84) |
|  | −1.80 |  |
| #29P-Hoc | 1.91 | 1.85 |
|  | 1.87 |  |
|  | 1.78 |  |
| #29P* | 4.95 | >4.5 |
|  | 4.97 | (4.95) |
|  | 4.94 |  |
| 1,6CHA | −0.50 | −0.97 |
|  | −1.14 |  |
|  | −1.26 |  |
| Cilengitide | −1.52 | <−1 |
|  | −1.75 | (−1.68) |
|  | −1.79 |  |
| AR372 | 5.02 | >4.5 |
|  | 4.72 | (4.85) |
|  | 4.80 |  |
| OM1186 | −0.22 | −0.19 |
|  | −0.21 |  |
|  | −0.14 |  |
| AR373 | 5.17 | >4.5 |
|  | 5.22 | (5.21) |
|  | 5.25 |  |
| FRX068 | −1.33 | <−1 |
|  | −1.55 | (−1.49) |
|  | −1.58 |  |
| Cil.-P | 3.76 | 3.95 |
|  | 4.00 |  |
|  | 4.10 |  |

PAMPA. The Parallel Artificial Membrane Permeability Assay (PAMPA) is used as an in vitro model of passive, transcellular permeation. PAMPA eliminates the added complexities of active transport, allowing ranking compounds just based on a simple membrane permeability property. This assay also allows evaluation of permeability over a large pH range, which is valuable for a preliminary understanding of how orally delivered compounds might be absorbed across the entire gastrointestinal tract. The PAMPA assay has been widely used in the pharmaceutical industry as a high throughput, quick and inexpensive permeability assay to roughly evaluate oral absorption potential [39]. Depending upon the types of lipids used and other experimental conditions, PAMPA may be designed to model absorption in gastrointestinal tract (PAMPA-GIT), blood-brain barrier penetration (PAMPA-BBB) or skin penetration (Skin PAMPA). All steps of the PAMPA were carried out according to pION Inc. PAMPA Explorer™ Manual. The main principle of the assay is the incubation of compound in donor chamber (a well in Donor Plate) with aqueous buffer, which is separated from acceptor chamber (a well in Acceptor Plate) with another buffer by a phospholipid or hydrocarbon membrane fixed on a filter support. After the test, concentrations in the corresponding donor and acceptor wells are measured and permeability is calculated. GIT model was simulated using GIT-0 phospholipid mix. Verapamil and quinidine (high permeability) and ranitidine (low permeability) were used as reference compounds. All compounds were tested in triplicates. Prisma HT buffer (pH 7.4) containing 50 µM test compounds and 0.5% DMSO were added into the Donor Plate wells. Acceptor Sink buffer was added into each well of the acceptor plate. Incubation was done at room temperature for 4 hours without stirring. After incubation, aliquots from both plates were transferred to optic UV-Vis plates and optic plates were read on microplate reader in absorbance mode in the range of 102-500 nm with 4 nm step. Compounds with low UV-Vis signal were detected by LC-MS/MS method. Then the apparent permeability coefficient was calculated. Results are shown in Table 5.

TABLE 5

PAMPA permeability coefficients of the peptide library*, in comparison to quinidine, verapamil and ranitidine.

| Compound ID | Permeability, $Log_{10}[10^{-6}$ cm/s] | | | | | Mass retention, % |
|---|---|---|---|---|---|---|
| | 1 | 2 | 3 | Mean | SD | |
| Quinidine | −4.6 | −4.5 | −4.5 | −4.5* | 0.06 | 56 |
| Verapamil | −4.1 | −4.0 | −4.3 | −4.2* | 0.16 | 44 |
| Ranitidine | <−7 | <−7 | <−7 | <−7* | — | 21 |
| #29P | −4.9 | −4.3 | −3.9 | −4.4 | 0.48 | 35 |
| #29 | <−7 | <−7 | <−7 | <−7 | — | 15 |
| #29P-Hoc | <−7 | <−7 | <−7 | <−7 | — | 10 |
| #29P* | −4.3 | −4.3 | −4.3 | −4.3 | 0.00 | 20 |
| 1,6CHA | −7 | <−7 | <−7 | <−7 | — | 27 |
| Cil.-P | Outlier −8.1 | −6.6 | −6.5 | −6.5 | 0.92 | 36 |
| Cilengitide | <−7 | <−7 | <−7 | <−7 | — | 1 |
| AR372 | −6.2 | −5.7 | −5.7 | −5.9 | 0.27 | 80 |
| OM1186 | <−7 | <−7 | <−7 | <−7 | — | 13 |
| AR373 | −5.6 | −5.1 | −4.8 | −5.2 | 0.43 | 22 |
| FRX068 | <−7 | <−7 | <−7 | <−7 | — | 2 |

*The compounds' structure is shown in FIG. 22. #29P is SEQ ID NO: 9, #29 is SEQ ID NO: 5, #29P-Hoc is SEQ ID NO: 21, #29P* is enantiomer of 29P (SEQ ID NO: 9), Cil.-P is pro drug of Cilengitide (c(f*VR(Hoc)$_2$GD); SEQ ID NO: 23), and 1,6CHA is SEQ ID NO: 22 (*aAAAA*A).

Peptides 29P (#29P) and #29P* (enantiomers) showed high permeability (>-5) in the PAMPA-GIT model system. Permeability of the two test compounds (AR372 (SEQ ID NO: 15) and AR373 (SEQ ID NO: 16) was in the range of >-5 to >-6. These results strengthen the hypothesis that LPCM enhances the permeability of RGD cyclohexapeptides through lipophilic membranes. Evidently, #29 (the unprotected derivative) show low permeability (<−7) and interestingly, the semi-protected #29P-Hoc also exhibits low permeability in PAMPA, suggesting that fully protected peptide is more permeable.

Cilengitide is a cyclopentapeptide with one N-methylated group (other peptides tested are cyclohexapeptides, with two N-methylated groups). It shows low permeability in PAMPA, however, LPCM protection (Cil.-P in FIG. 22; SEQ ID NO: 23) does not enhance the permeability, and this suggests that there are also structural considerations that influence the permeability, other than the lipophilicity of the peptide (log D of Cil.-P is 3.95, vs. <−1 in Cilengitide).

Caco-2. Caco-2 cells were cultured in 75 cm2 flasks to 80-90% confluence according to the ATCC and Millipore recommendations [40] in humidified atmosphere at 37° C. and 5% $CO_2$. Cells were detached with Trypsin/EDTA solution and resuspended in the cell culture medium to a final concentration of $2 \times 10^5$ cells/ml. 500 µl of the cell suspension was added to each well of HTS 24-Multiwell Insert System and 1000 µl of prewarmed complete medium was added to each well of the feeder-plate. Caco-2 cells were incubated in Multiwell Insert System for 21 days before the transport experiments. The medium in filter plate and feeder tray was refreshed every other day. After 21 days of the cell growth, the integrity of the monolayer was verified by measuring the transepithelial electrical resistance (TEER) for every well using the Millicell-ERS system ohm meter. The final TEER values were within the range 150-600Ω× cm2 as required for the assay conditions. 24-well insert plate was removed from its feeder plate and placed in a new sterile 24-well transport analysis plate. The inserts were washed with PBS after medium aspiration. Propranolol, Atenolol, Quinidine and Digoxin were used as reference compounds. To determine the rate of compounds transport in apical (A)-to-basolateral (B) direction, 300 µl of the test compound dissolved in transport buffer at 10 µM (HBSS, 25 mM HEPES, pH=7.4) was added into the filter wells; 10004 of buffer (HBSS, 25 mM HEPES, pH=7.4) was added to transport analysis plate wells. To determine transport rates in the basolateral (B)-to-apical (A) direction, 1000 µL, of the test compound solutions was added into the wells of the transport analysis plate, the wells in filter plate were filled with 300 µL, of buffer (apical compartment). The final concentrations of the test compounds were 10 µM. The effect of the inhibitor on the P-gp-mediated transport of the tested compounds was assessed by determining the bidirectional transport in the presence or absence of verapamil. The Caco-2 cells were preincubated for 30 min at 37° C. with 100 µM of verapamil in both apical and basolateral compartments. After removal of the preincubation medium the test compounds (final concentration 10 µM) with verapamil (100 µM) in transport buffer were added in donor wells, while the receiver wells were filled with the appropriate volume of transport buffer with 100 µM of verapamil. The plates were incubated for 90 min at 37° C. under continuous shaking at 50 rpm. 75 µl aliquots were taken from the donor and receiver compartments for LC-MS/MS analysis. All samples were mixed with 2 volumes of acetonitrile followed by protein sedimentation by centrifuging at 10000 rpm for 10 minutes. Supernatants were analyzed using the HPLC system coupled with tandem mass spectrometer. Results are shown in Tables 6 and 7 (compounds' structure is shown in FIG. 22).

NO: 16) are prodrugs for OM1186 (cyclo(Leu-Pro-Pro-Phe-Arg-Gly-Asp-Leu-Ala)(SEQ ID NO:17) and FRX068 (cyclo(Leu-Pro-Pro-Gly-Leu-Arg-Gly-Asp)(SEQ ID NO: 18), respectively. The caco-2 and PAMPA results of these peptides are compatible with the RGD library. In the presence of verapamil, the efflux ratio is lower significantly in these peptides.

Prodrug modification for Cilengitide did not enhance the permeability in Caco-2 and does not show efflux activity, which was typical for other RGD prodrug derivatives. The

TABLE 6

A-B and B-A permeability data.

| Test compound | $P_{app}$ (AB), $10^{-6}$ cm/s | | | | | $P_{app}$ (BA), $10^{-6}$ cm/s | | | | | Net efflux* |
|---|---|---|---|---|---|---|---|---|---|---|---|
| | 1 | 2 | 3 | Mean | SD | 1 | 2 | 3 | Mean | SD | |
| Atenolol | 1.0 | 0.8 | 0.4 | 0.8 | 0.3 | | | | | | |
| Propranolol | 14.9 | 24.1 | 15.3 | 18.1 | 5.2 | 13.6 | 15.3 | 17.0 | 15.3 | 1.7 | 0.8 |
| Digoxin | 0.4 | 0.3 | 0.5 | 0.4 | 0.1 | 9.4 | 12.0 | 14.7 | 12.0 | 2.6 | 28.6 |
| Quinidine | 6.2 | 4.4 | 3.9 | 4.8 | 1.2 | 18.8 | 25.0 | 27.1 | 23.6 | 4.3 | 4.9 |
| #29P | 0.1 | 0.1 | 0.1 | 0.1 | 0.1 | 15.7 | 17.9 | 16.4 | 16.7 | 1.1 | 144.4 |
| #29 | 1.0 | 0.2 | 0.9 | 0.7 | 0.4 | 0.3 | 0.4 | 0.2 | 0.3 | 0.1 | 0.4 |
| #29P-Hoc | 0.3 | 0.3 | 0.2 | 0.3 | 0.0 | 0.2 | 0.2 | 0.3 | 0.3 | 0.1 | 1.0 |
| 1,6CHA | 0.0 | 0.1 | 0.1 | 0.1 | 0.1 | 0.1 | 0.1 | 0.2 | 0.1 | 0.1 | 1.1 |
| #29P* | 0.4 | 0.4 | 0.2 | 0.3 | 0.1 | 17.7 | 20.8 | 21.4 | 20.0 | 2.0 | 62.9 |
| Cil.-P | 0.6 | 0.2 | 0.2 | 0.3 | 0.2 | 0.4 | 0.3 | 0.3 | 0.3 | 0.0 | 1.1 |
| Cilengitide | 0.4 | 0.6 | 0.6 | 0.6 | 0.1 | 0.6 | 0.8 | 0.5 | 0.6 | 0.1 | 1.1 |
| AR372 | <0.01** | <0.01** | <0.01** | <0.01 | — | 0.5 | 0.5 | 0.3 | 0.4 | 0.1 | 40 |
| OM1186 | <0.6** | <0.3** | — | <0.3 | — | 0.1 | 0.2 | 0.3 | 0.2 | 0.1 | 0.6 |
| AR373 | <0.1** | — | <0.1** | <0.1 | — | 8.6 | 12.1 | 10.9 | 10.6 | 1.8 | 152.7 |
| FRX068 | 0.3 | 0.2 | 0.2 | 0.3 | 0.1 | 0.3 | 0.3 | 0.3 | 0.3 | 0.0 | 1.1 |

*Efflux ratio is expressed as the quotient of $P_{app}$ (BA) to $P_{app}$ (AB)
**The obtained experimental value for receiver compartment is less than LOD (3 × [signal-to-noise] value) for a compound

TABLE 7

Data of A-B and B-A permeability in the presence of Verapamil

| Test compound | $P_{app}$ (AB), $10^{-6}$ cm/s | | | | | $P_{app}$ (BA), $10^{-6}$ cm/s | | | | | Net efflux* |
|---|---|---|---|---|---|---|---|---|---|---|---|
| | 1 | 2 | 3 | Mean | SD | 1 | 2 | 3 | Mean | SD | |
| Digoxin | 2.4 | 2.8 | 3.2 | 2.8 | 0.4 | 5.0 | 4.4 | 3.6 | 4.3 | 0.7 | 1.5 |
| Quinidine | 24.8 | 20.9 | 22.5 | 22.7 | 2.0 | 13.8 | 17.1 | 19.7 | 16.9 | 3.0 | 0.7 |
| #29P | 1.6 | 1.9 | 2.0 | 1.8 | 0.2 | 11.7 | 13.1 | 14.1 | 13.0 | 1.2 | 7.1 |
| #29 | <0.8** | — | — | <0.8 | — | 0.4 | 0.2 | 0.3 | 0.3 | 0.1 | 0.1 |
| #29P-Hoc | 0.3 | 0.3 | 0.2 | 0.3 | 0.1 | 0.1 | 0.1 | 0.1 | 0.1 | 0.0 | 0.5 |
| 1,6CHA | 1.6 | 0.3 | 0.1 | 0.7 | 0.8 | 0.1 | 0.1 | 0.1 | 0.1 | 0.0 | 0.2 |
| #29P* | 1.8 | 1.3 | 1.1 | 1.4 | 0.4 | 12.7 | 14.4 | 14.4 | 13.9 | 1.0 | 9.8 |
| Cil.-P | 1.0 | 0.7 | 0.5 | 0.7 | 0.2 | 0.3 | 0.2 | 0.1 | 0.2 | 0.1 | 0.2 |
| Cilengitide | 0.2 | 0.2 | 0.2 | 0.2 | 0.0 | 0.3 | 0.3 | 0.4 | 0.4 | 0.0 | 1.6 |
| AR372 | 0.7 | 0.3 | 0.3 | 0.4 | 0.2 | 0.2 | 0.2 | 0.2 | 0.2 | 0.0 | 0.5 |
| OM1186 | 0.2 | 0.0 | 0.5 | 0.2 | 0.3 | 0.2 | 0.2 | 0.2 | 0.2 | 0.0 | 0.7 |
| AR373 | 0.8 | 0.6 | 0.4 | 0.6 | 0.2 | 4.2 | 4.5 | 5.3 | 4.7 | 0.6 | 7.7 |
| FRX068 | 0.6 | 0.1 | 0.2 | 0.3 | 0.2 | 0.4 | 0.4 | 0.2 | 0.3 | 0.1 | 1.1 |

*Efflux ratio is expressed as the quotient of $P_{app}$ (BA) to $P_{app}$ (AB)
**The obtained experimental value for receiver compartment is less than LOD (3 × [signal-to-noise] value) for a compound

29P and #29P* (enantiomer) showed high permeability, while 429P-Hoc showed lower permeability in PAMPA. This is compatible with the caco-2 results—the LPCM method enhances the permeability through the lipophilic membrane, and low permeability in caco-2 (AB) is due to efflux activity. In past caco-2 results, only two Hoc groups protection or only OMe protection (in peptide 12 (SEQ ID NO: 2)) also was not enough to significantly enhance permeability. It seems that all three protection groups better enhance the permeability. AR372 (cyclo(Leu-Pro-Pro-Phe-Arg(Hoc)2-Gly-Asp-Leu-Ala)(SEQ ID NO: 15) and AR373 (cyclo(Leu-Pro-Pro-Gly-Leu-Arg(Hoc)2-Gly-Asp)(SEQ ID LPCM does not seem to work here, since it does not elevate the permeability in caco-2 or PAMPA and does not show efflux activity.

Example 7: In Vivo Study

To estimate the efficacy of the peptides in inhibition of human cancer, the peptides are studied in tumor mice models. Mice are challenged with human cancer cells and treated with increasing concentrations of the prodrugs described herein above. The peptides are administered orally and compared to controls.

REFERENCES

1. Jay S. Desgrosellier and David A. Cheresh. Integrins in cancer: biological implications and therapeutic opportunities Nat Rev Cancer. 2010 January; 10(1): 9-22.
2. Aumailley M, Gurrath M, Müller G, Calvete J, Timpl R, Kessler H. Arg-Gly-Asp constrained within cyclic pentapeptides. Strong and selective inhibitors of cell adhesion to vitronectin and laminin fragment P1. FEBS Lett. 1991; 291:50-4.
3. Haubner R, Finsinger D, Kessler H. Stereoisomeric Peptide Libraries and Peptidomimetics for Designing Selective Inhibitors of the αvβ3 Integrin for a New Cancer Therapy. Angew. Chemie. Hüthig & Wepf Verlag; 1997; 36:1374-89.
4. Dechantsreiter M A, Planker E, Matha B, Lohof E, Holzemann G, Jonczyk A, et al. N-Methylated Cyclic RGD Peptides as Highly Active and Selective αvβ3 Integrin Antagonists. J. Med. Chem. 1999; 42:3033-40.
5. Mas-Moruno C, Rechenmacher F, Kessler H. Cilengitide: the first anti-angiogenic small molecule drug candidate design, synthesis and clinical evaluation. Anticancer. Agents Med. Chem. 2010; 10:753-68.
6. Reardon D A, Neyns B, Weller M, Tonn J C, Nabors L B, Stupp R. Cilengitide: an RGD pentapeptide αvβ3 and αvβ5 integrin inhibitor in development for glioblastoma and other malignancies. Futur. Oncol. 2011; 7:339-54.
7. Bock J E, Gavenonis J, Kritzer J A. Getting in shape: controlling peptide bioactivity and bioavailability using conformational constraints. ACS Chem. Biol. 2013; 8:488-99.
8. Wang C K, Craik D J. Cyclic peptide oral bioavailability: Lessons from the past. Biopolymers. 2016; 106:901-9.
9. Nomenclature and Symbolism for Amino. Acids and Peptides Recommendations 1983. IUPAC-IUB Jt. Comm.
10. Ovadia O, Greenberg, S, Chatterjee J, Laufer B, Opperer F et al. The Effect of Multiple N-Methylation on Intestinal Permeability of Cyclic Hexapeptides. Mol. Pharmaceutics 2011, 8, 479-487.
11. A. O. Frank, E. Otto, C. Mas-Moruno, H. B. Schiller, L. Marinelli, et al. Conformational control of integrin-subtype selectivity in isoDGR peptide motifs: a biological switch. Angew. Chem. Int. Ed. 2010, 49, 9278-9281.
12. T. G. Kapp, M. Fottner, O. V. Maltsev, H. Kessler, Small Cause, Great Impact: Modification of the Guanidine Group in the RGD Motif Controls Integrin Subtype Selectivity. Angew. Chem. 2016, 128, 1564.
13. Cherniakov, Domb A J, Hoffman A. Self-nano-emulsifying drug delivery systems: an update of the biopharmaceutical aspects. Expert Opin Drug Deliv. 2015 July; 12(7):1121-33.
14. Beck J G, Chatterjee J, Laufer B, Kiran M U, Frank A O, Neubauer S, et al. Intestinal Permeability of Cyclic Peptides: Common Key Backbone Motifs Identified. J. Am. Chem. Soc. 2012; 134:12125-33.
15. Marelli U K, Bezencon J, Puig E, Ernst B, Kessler H. Enantiomeric Cyclic Peptides with Different Caco-2 Permeability Suggest Carrier-Mediated Transport. Chemistry. 2015 May 26; 21(22):8023-7.
16. Xiong J-P. Crystal Structure of the Extracellular Segment of Integrin alpha Vbeta 3 in Complex with an Arg-Gly-Asp Ligand. Science. 2002; 296:151-5.
17. Takagi J, Strokovich K, Springer T A, Walz T. Structure of integrin alpha5beta1 in complex with fibronectin. EMBO J. 2003; 22:4607-15.
18. Dong X, Zhao B, Jacob R E, Zhu J, Koksal A C, Lu C, et al. Force interacts with macromolecular structure in activation of TGF-β. Nature, 2017; 542:55-9.
19. Springer T A, Zhu J, Xiao T. Structural basis for distinctive recognition of fibrinogen gammaC peptide by the platelet integrin alphaIIbbeta3. J. Cell Biol. 2008; 182:791-800.
20. Kapp T G, Rechenmacher F, Neubauer S, Maltsev O V, Cavalcanti-Adam E A, Zarka R, et al. A Comprehensive Evaluation of the Activity and Selectivity Profile of Ligands for RGD-binding Integrins Sci Rep. 2017 Jan. 11; 7:39805.
21. Bochen A, Kiran Marelli U, Otto E, Pallarola D, Mas-Moruno C, Saverio Di Leva F, et al. Biselectivity of isoDGR Peptides for Fibronectin Binding Integrin Subtypes a5131 and αvβ6: Conformational Control through Flanking Amino Acids. J. Med. Chem., 2013, 56 (4), pp 1509-1519.
22. van Ryn J, Goss A, Hauel N, Wienen W, Priepke H, Nar H, et al. The discovery of dabigatran etexilate. Front Pharmacol. 2013 Feb. 12; 4:12.
23. Artursson P, Karlsson J. Correlation between oral drug absorption in humans and apparent drug permeability coefficients in human intestinal epithelial (Caco-2) cells. Biochem. Biophys. Res. Commun. 1991; 175:880-5.
24. Kumar K K V, Karnati S, Reddy M B, Chandramouli R. Caco-2 cell lines in drug discovery—an updated perspective. J. basic Clin. Pharm. 2010; 1:63-9.
25. Hubatsch I, Ragnarsson E G E, Artursson P. Determination of drug permeability and prediction of drug absorption in Caco-2 monolayers. Nat. Protoc. 2007; 2:2111-9.
26. Artursson P. Epithelial transport of drugs in cell culture. I: A model for studying the passive diffusion of drugs over intestinal absorptive (Caco-2) cells. J. Pharm. Sci. 1990; 79:476-82.
27. Hunter J, Hirst B H, Simmons N L. Drug absorption limited by P-glycoprotein-mediated secretory drug transport in human intestinal epithelial Caco-2 cell layers. Pharm Res. 1993. p. 743-9.
28. Picariello G, Addeo F. Use of brush border membrane vesicles to simulate the human intestinal digestion. Food Res. Int. 2016; 88:327-35.
29. Powell MF. Chapter 30. Peptide Stability in Drug Development: in vitro Peptide Degradation in Plasma and Serum. Annual Reports in Medicinal Chemistry Volume 28, 1993, Pages 285-294.
30. Cherniakov I, Izgelov D, Domb A. J., Hoffman A. The effect of Pro NanoLipospheres (PNL) formulation containing natural absorption enhancers on the oral bioavailability of delta-9-tetrahydrocannabinol (THC) and cannabidiol (CBD) in a rat model. European Journal of Pharmaceutical Sciences, 109 (2017) 21-30.
31. P. P. Wong, N. Bodrug, K. M. Hodivala-Dilke, Exploring novel methods for modulating tumor blood vessels in cancer treatment Curr. Biol. 2016, 26, 1161-1166.
32. J. P. Xiong, T. Stehle, R. G. Zhang. A. Joachimiak, M. Frech, S. L. Goodman, M. A. Crystal structure of the complete integrin aVr33 ectodomain plus an α/β transmembrane fragment Arnaout, Science 2002, 296, 151-155.
33. G. M. Sastry, M. Adzhigirey, T. Day, R. Annabhimoju, W. Sherman, J. Protein and ligand preparation: parameters, protocols, and influence on virtual screening enrichments. Comput. Aid. Mol. Des. 2013, 27, 221-234.
34. J. R. Greenwood, D. Calkins, A. P. Sullivan, J. C. Shelley, J. Comput. Towards the comprehensive, rapid, and accurate prediction of the favorable tautomeric states of drug-like molecules in aqueous solution Aided Mol. Des. 2010, 24, 591-604.
35. J. C. Shelley, A. Cholleti, L. Frye, J. R. Greenwood, M. R. Timlin, M. Uchimaya, J. Epik: a software program for pK(a) prediction and protonation state generation for drug-like moleculesComput. Aided Mol. Des. 2007, 21, 681-691.
36. R. A. Friesner, J. L. Banks, R. B. Murphy, T. A. Halgren, J. J. Klicic, et al. Glide: a new approach for rapid, accurate docking and scoring. 1. Method and assessment of docking accuracy J. Med. Chem. 2004, 47, 1739-1749.
37. T. A. Halgren, R. B. Murphy, R. A. Friesner, H. S. Beard, L. L. Frye, et al. Glide: a new approach for rapid, accurate docking and scoring. 2. Enrichment factors in database screening. J. Med. Chem. 2004, 47, 1750-1759.
38. E. Harder, W. Damm, J. Maple, C. Wu, M. Reboul, et al. OPLS3: A Force Field Providing Broad Coverage of Drug-like Small Molecules and Proteins J. Chem. Theory Comput. 2016, 12, 281-296.
39. M. Kansy, F. Senner, K. Gubernator. Physicochemical high throughput screening: parallel artificial membrane permeation assay in the description of passive absorption processes. J. Med. Chem. 1998, 41, 1007-1010
40. Arena A., Phillips J. Optimization of Caco-2 Cell Growth and Differentiation for Drug Transport Assay Studies Using a 96 well Multi Screen Caco-2 Assay System. Millipore Protocol Note PC1060EN00P; 2003.
41. M. Weinmtiller, F. Rechenmacher, U. Kiran Marelli, F. Reichart, T. G. Kapp, A. F. B. Rader, F. S. Di Leva, L. Marinelli, E. Novellino, J. M. Muñoz-Félix, K. Hodivala-Dilke, A. Schumacher, J. Fanous, C. Gilon, A. Hoffman, H. Kessler, Overcoming the lack of oral availability of cyclic hexapeptides: Design of a new selective and orally available ligand for the integrin $\alpha v \beta$, Angew. Chem. Int. Ed. 2017, 56, 16405-16409. doi10.1002/anie.201709709; Angew. Chem. 2017, 129, 16624-16629.
42. A. Schumacher-Klinger, J. Fanous, S. Merzbach, M. Weinmueller, F. Reichart, A. Rader, A. Domaglaska, C. Gilon, H. Kessler, A. Hoffman, Enhancing oral bioavailability of cyclic RGD hexa-peptides by the Lipophilic Prodrug Charge Masking approach: Redirection of peptide intestinal permeability from paracellular to transcellular pathway, Molecular Pharmaceutics 2018, 15. 3468-3477.

The invention claimed is:

1. A cyclic hexapeptide having a sequence selected from the group consisting of:

(i)
   *aRGDA*A;                           (SEQ ID NO: 2)

(ii)
   *vRGDA*A;                           (SEQ ID NO: 5)
   and (iii)
   *fRGDA*A;                           (SEQ ID NO: 6)

wherein * is N-methylation of the followed amino acid, R is arginine, G is glycine, D is aspartic acid, A is alanine, a is alanine in the D configuration, v is valine in the D configuration, and f is phenylalanine in the D configuration.

2. The cyclic hexapeptide of claim 1, wherein the hexapeptide has a binding affinity to the integrin αvβ3, wherein the binding affinity has an $IC_{50}$ of less than 100 nM.

3. The cyclic peptide of claim 1, wherein the cyclization is a head-to-tail cyclization.

4. A conjugate or a fusion protein comprising the cyclic hexapeptide of claim 1.

5. A prodrug comprising the cyclic hexapeptide of claim 1, wherein the charged side chains of the arginine and aspartic acid residues are masked, and the prodrug has a net neutral charge.

6. The prodrug of claim 5, wherein one or more of the charged nitrogen atoms of the chain of the arginine residue are transformed into carbamates having —$NHCO_2R^1$ moiety, and the charged side chain of the aspartic acid residue is transformed into an ester having a —$CO_2R^2$ moiety, wherein $R^1$ and $R^2$ are independently selected from $C_{1-14}$ alkyl.

7. The prodrug of claim 5, wherein the arginine residue is linked to a hexyloxycarbonyl (Hoc) moiety.

8. The prodrug of claim 5, wherein the aspartic acid residue is linked to a methyl ester (OMe) moiety.

9. The prodrug of claim 5, wherein the cyclic peptide comprises two hexyloxycarbonyl (Hoc) moieties.

10. The prodrug of claim 5, wherein the prodrug has a formula selected from the group consisting of SEQ ID NO: 9, SEQ ID NO: 10, and SEQ ID NO: 12.

11. A pharmaceutical composition comprising as an active ingredient the prodrug according to claim 5, and a pharmaceutically acceptable carrier, excipient, or diluent.

12. The pharmaceutical composition of claim 11, wherein the composition is formulated for an oral administration.

* * * * *